(12) United States Patent
Boyle

(10) Patent No.: US 6,656,351 B2
(45) Date of Patent: Dec. 2, 2003

(54) EMBOLIC PROTECTION DEVICES ONE WAY POROUS MEMBRANE

(75) Inventor: William J. Boyle, Fallbrook, CA (US)

(73) Assignee: Advanced Cardiovascular Systems, Inc., Santa Clara, CA (US)

(*) Notice: Subject to any disclaimer, the term of this patent is extended or adjusted under 35 U.S.C. 154(b) by 0 days.

(21) Appl. No.: 09/945,151

(22) Filed: Aug. 31, 2001

(65) Prior Publication Data
US 2003/0042186 A1 Mar. 6, 2003

(51) Int. Cl.[7] .......................... A61M 29/00; B01D 35/14
(52) U.S. Cl. .................... 210/136; 210/251; 210/359; 606/200; 606/194
(58) Field of Search ..................... 606/200, 194; 604/106; 210/97, 136, 251, 359; 137/511

(56) References Cited

U.S. PATENT DOCUMENTS

| | | | |
|---|---|---|---|
| 6,383,206 B1 * | 5/2002 | Gillick et al. ............... | 606/200 |
| 2002/0049468 A1 * | 4/2002 | Streeter et al. ............. | 606/200 |
| 2002/0161389 A1 * | 10/2002 | Boyle et al. ................ | 606/200 |

* cited by examiner

*Primary Examiner*—Joseph Drodge
*Assistant Examiner*—Terry K. Cecil

(57) ABSTRACT

An embolic protection device for use in a blood vessel when an interventional procedure is being performed in a stenosed or occluded region to capture any embolic material which may be created and released into the bloodstream during the procedure. The device includes a filtering assembly having a self-expanding strut assembly and a filter element attached thereto. The filtering assembly is capable of allowing controlled backwards flow of blood through the filter assembly, or blocking the backwards flow entirely, during aspiration of embolic material trapped within the filter assembly.

34 Claims, 28 Drawing Sheets

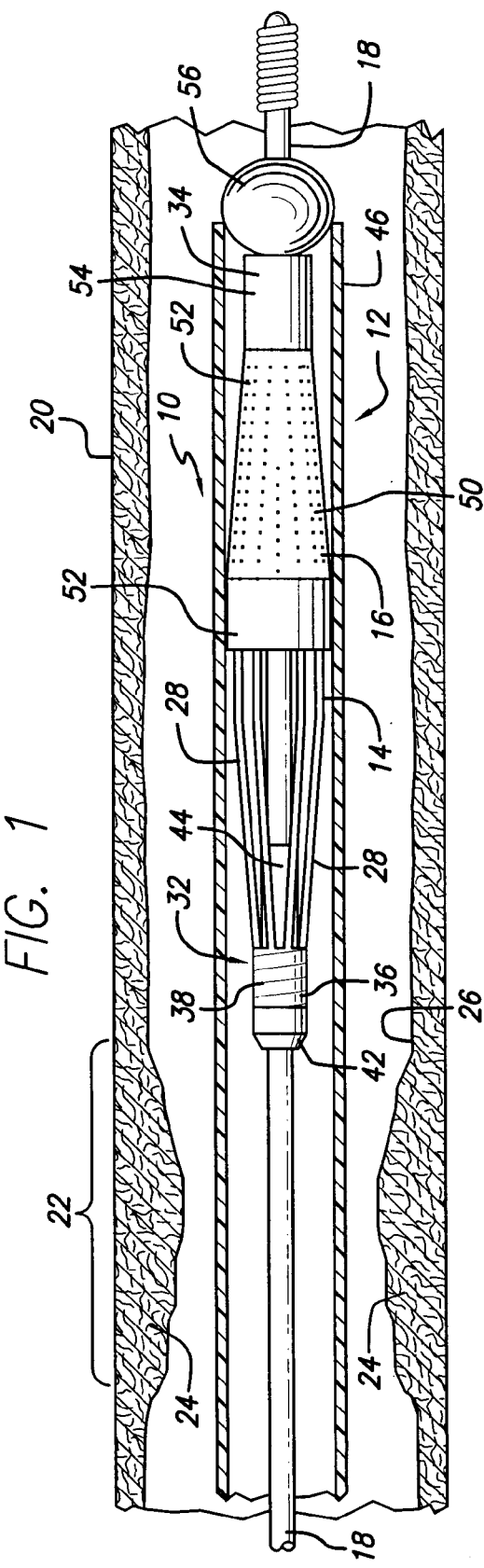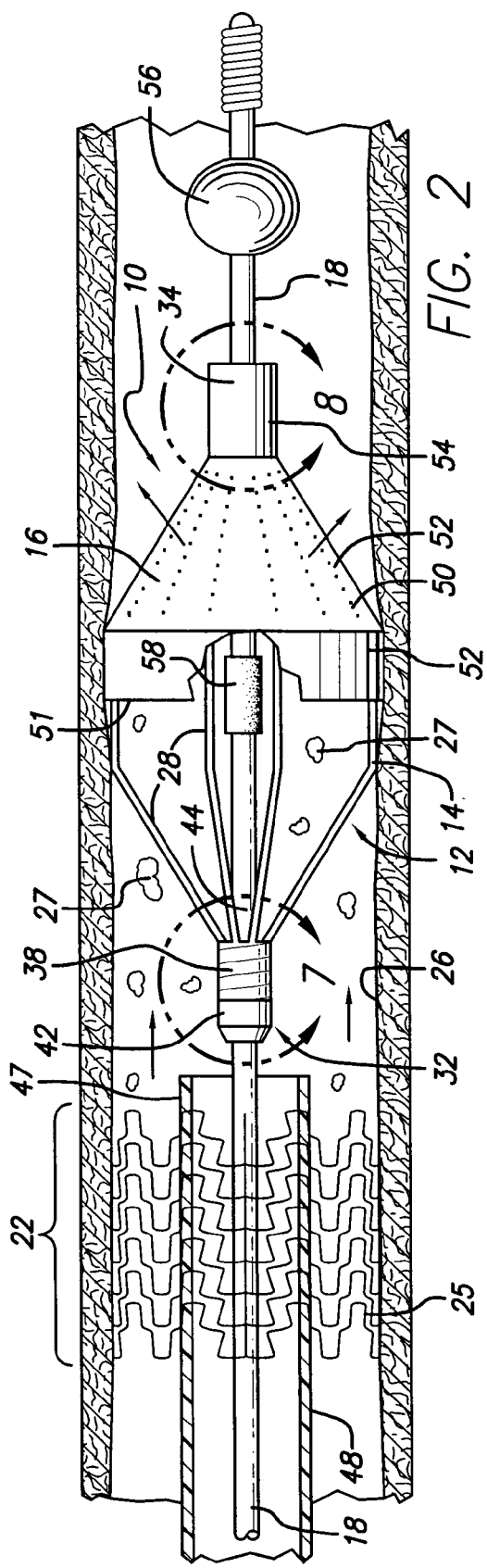

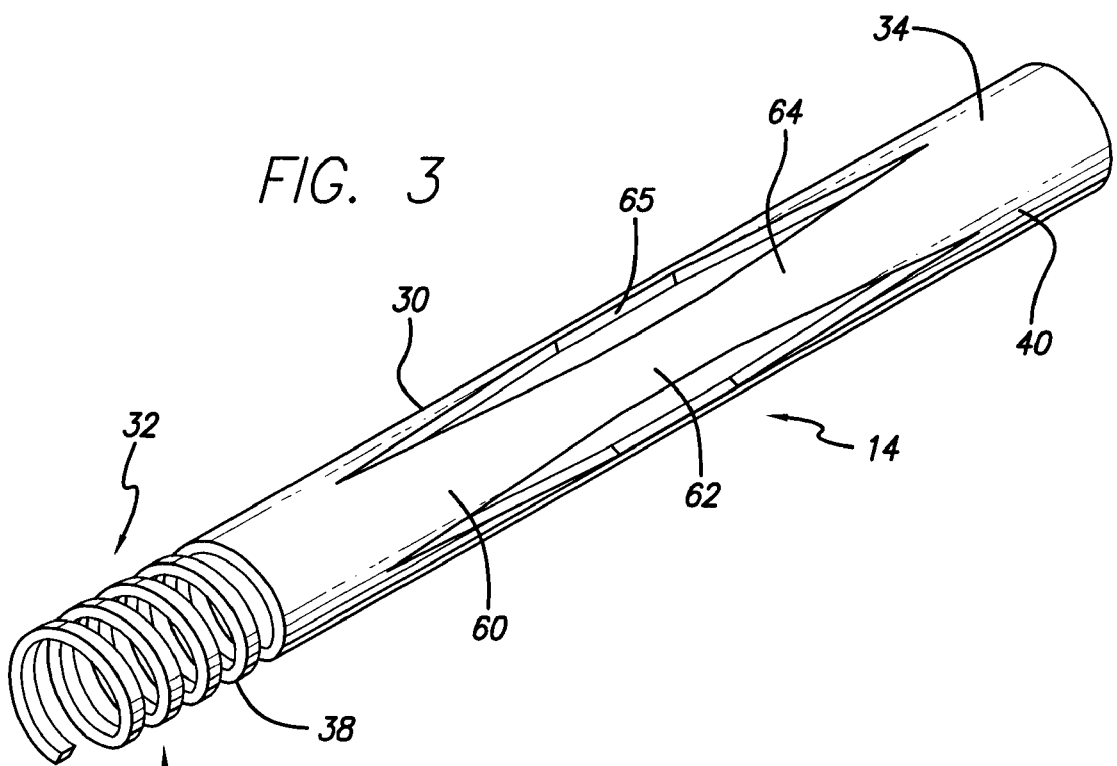
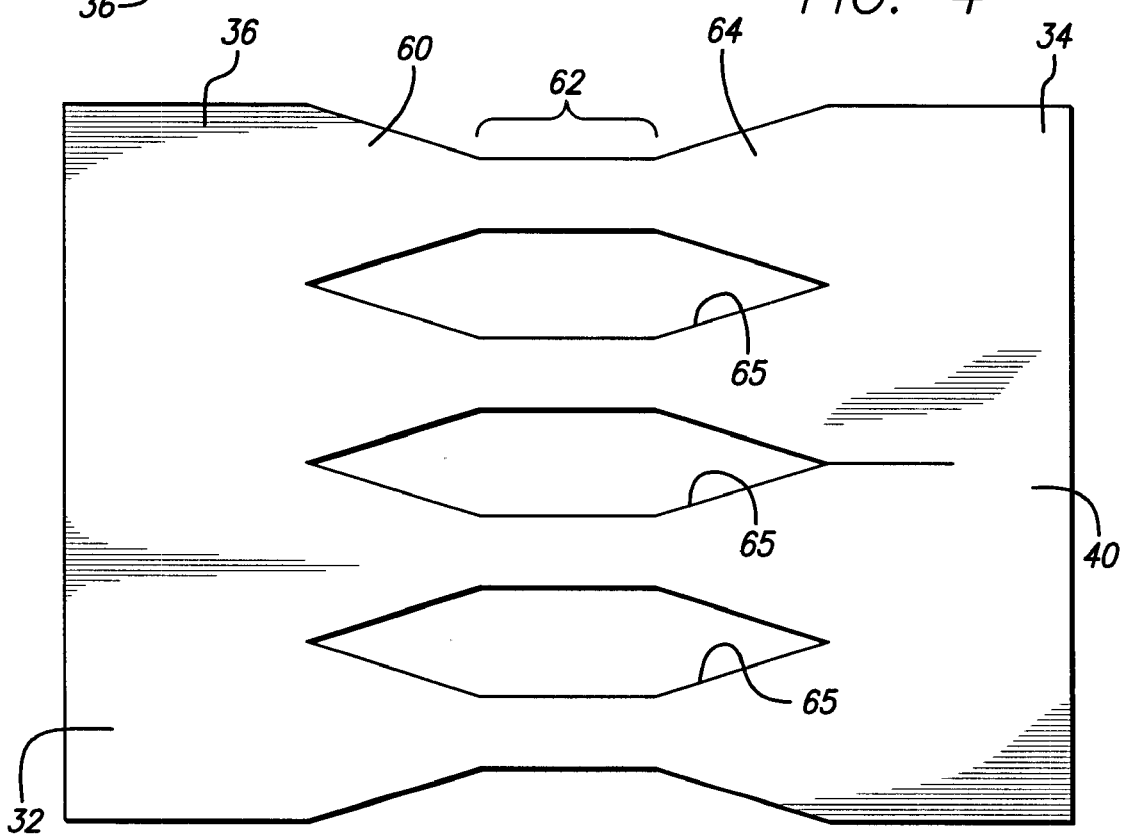

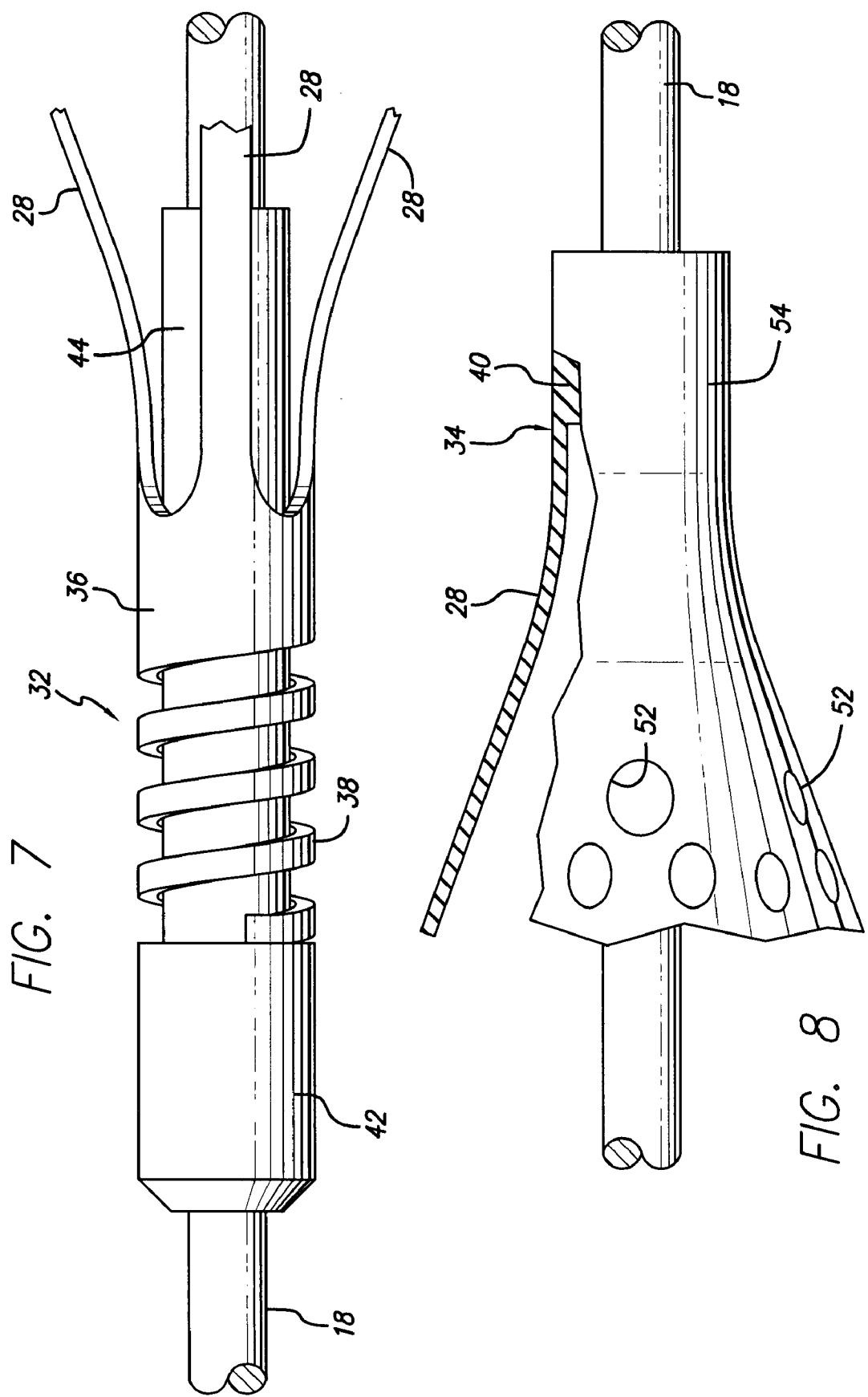

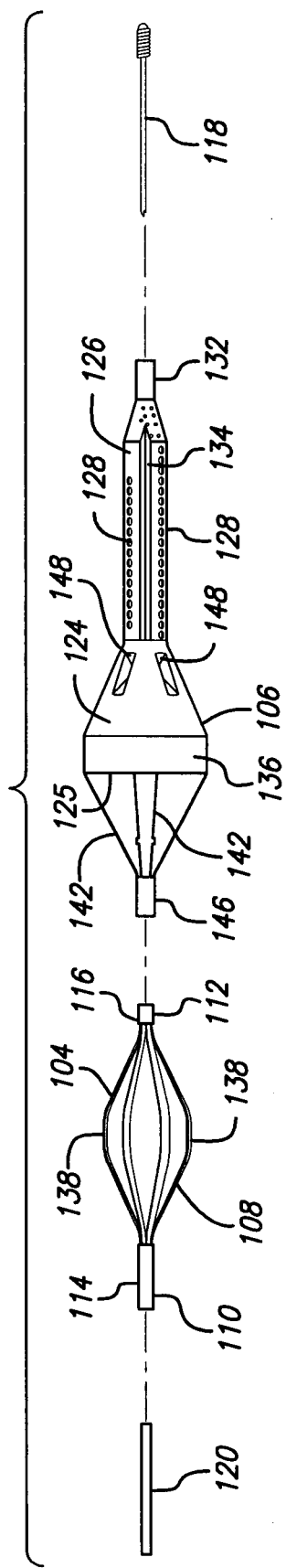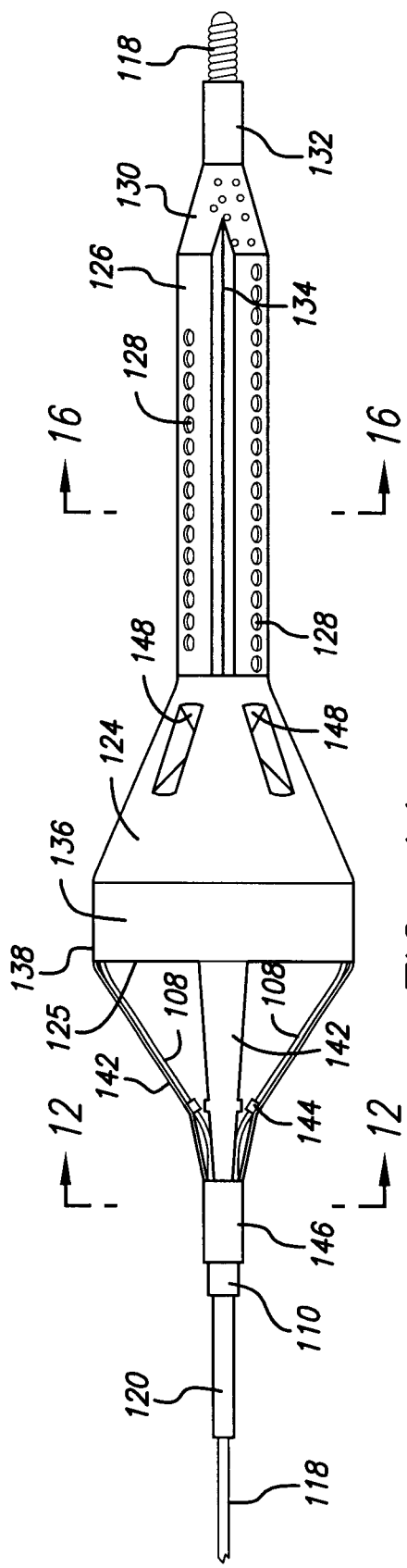

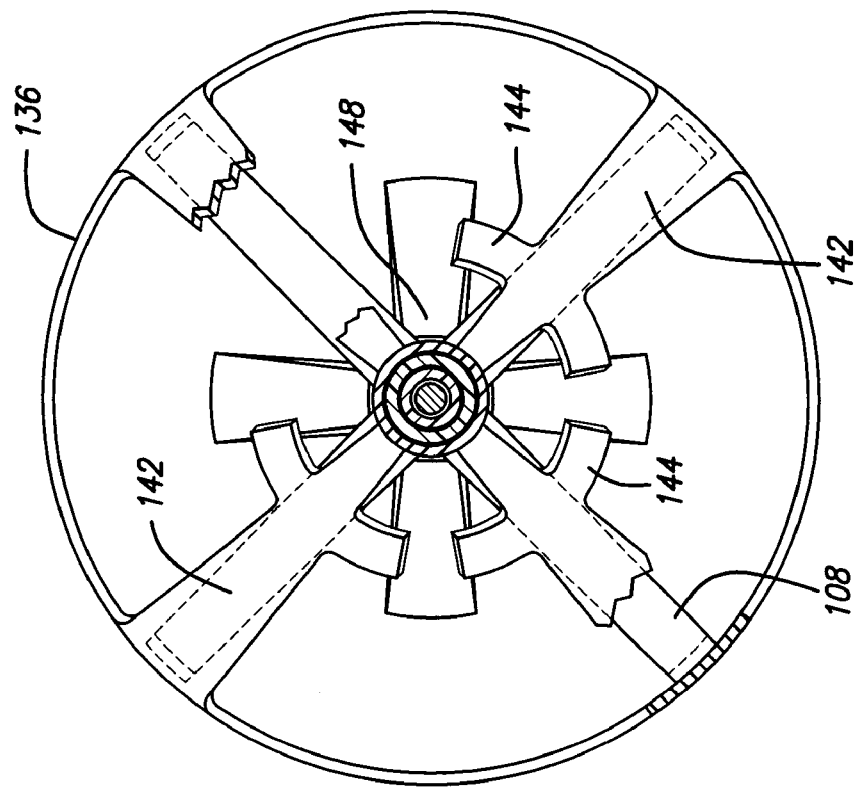
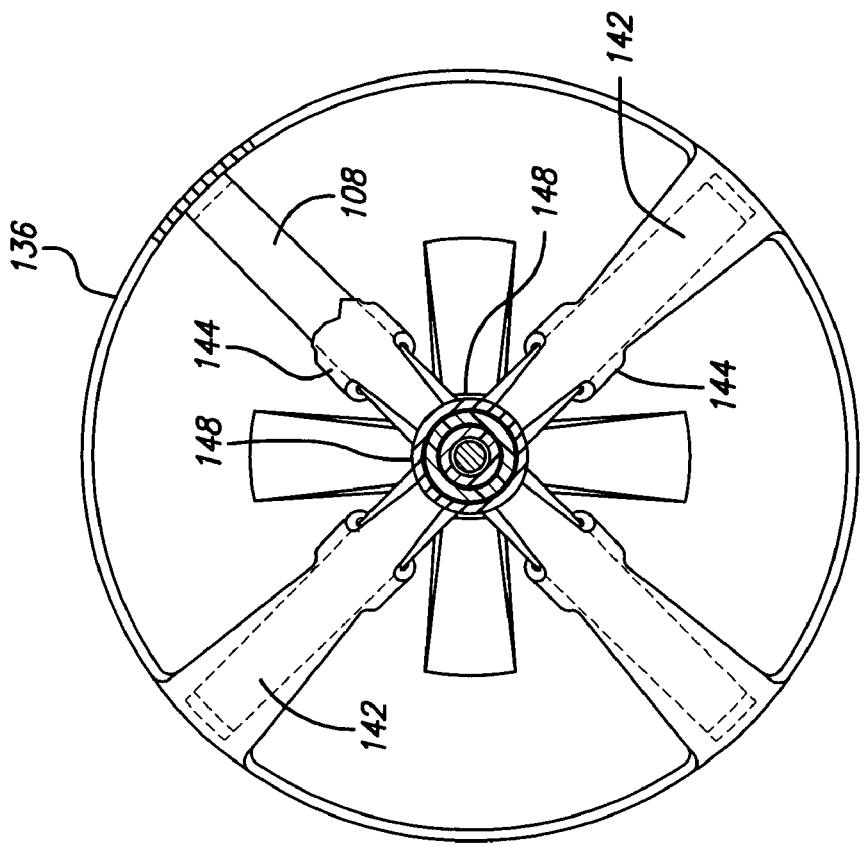

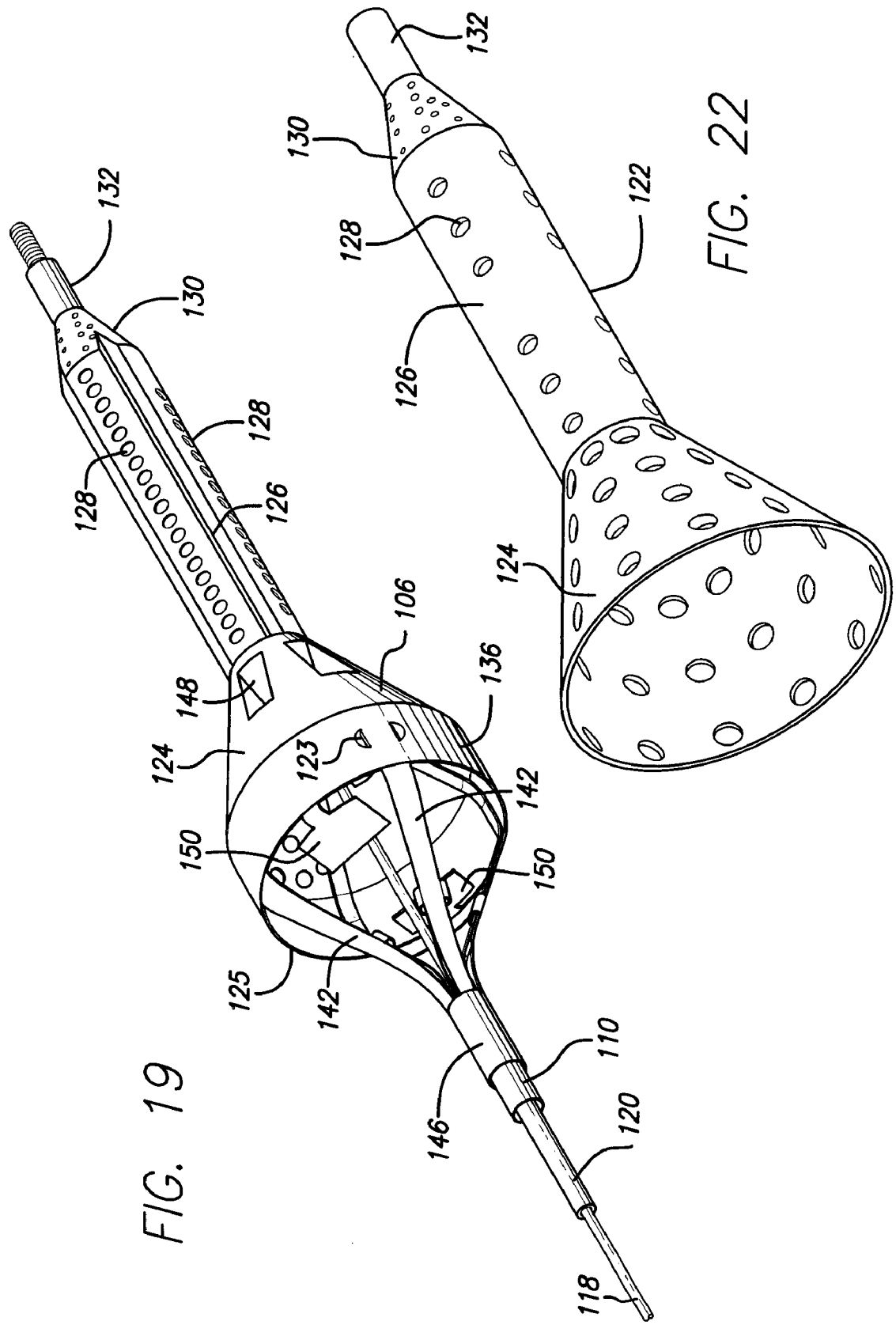

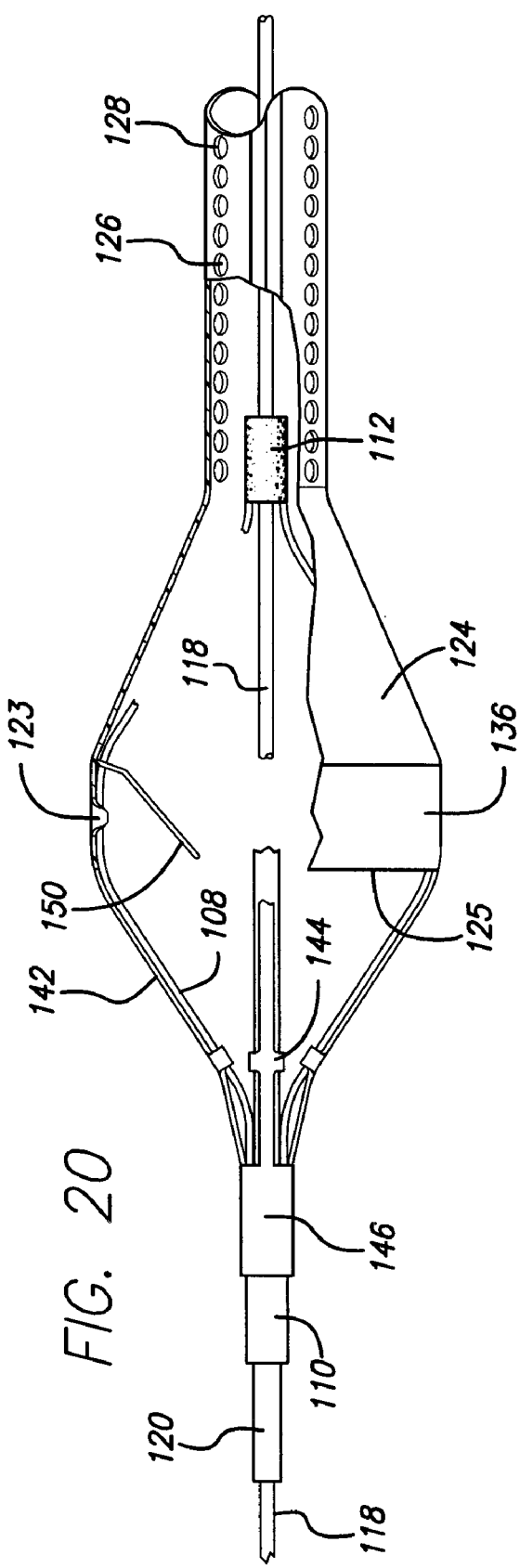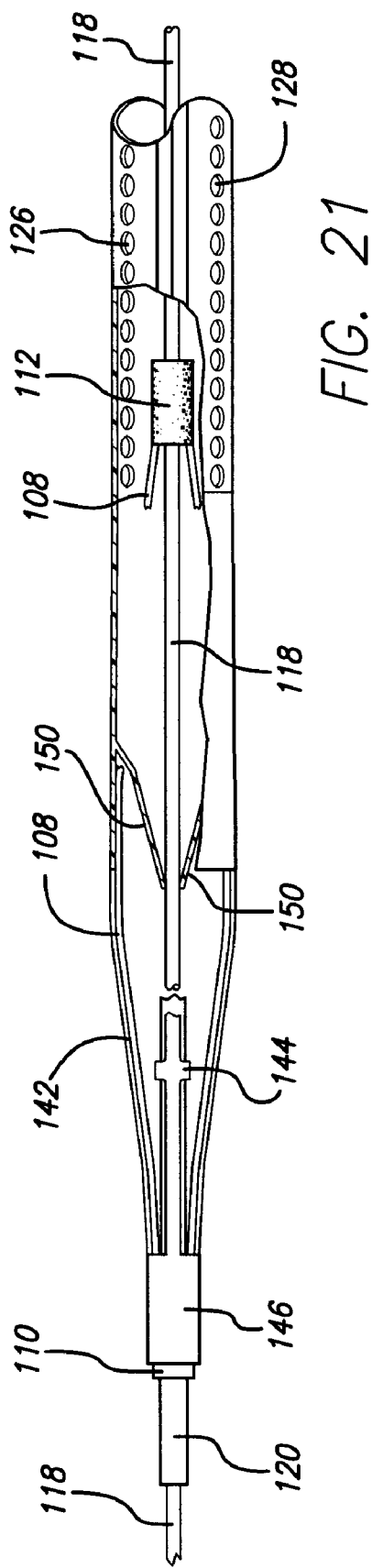

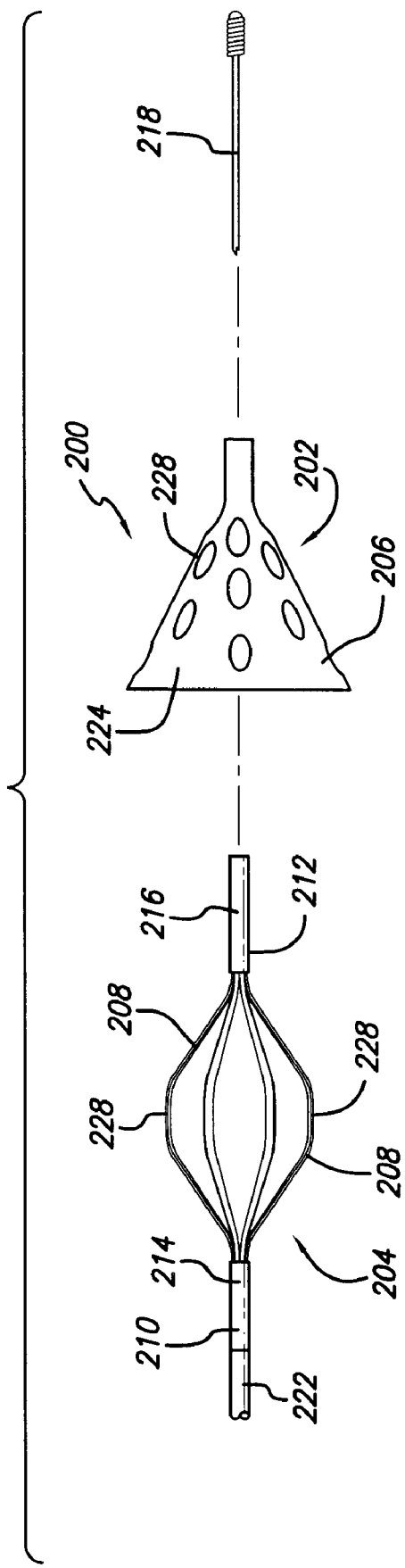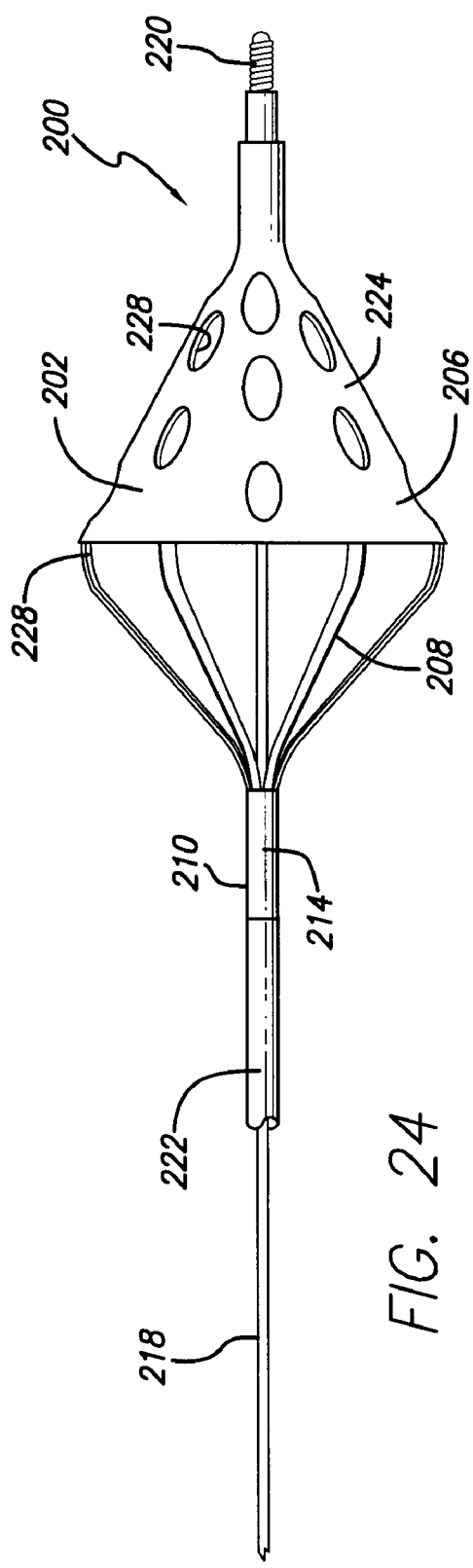

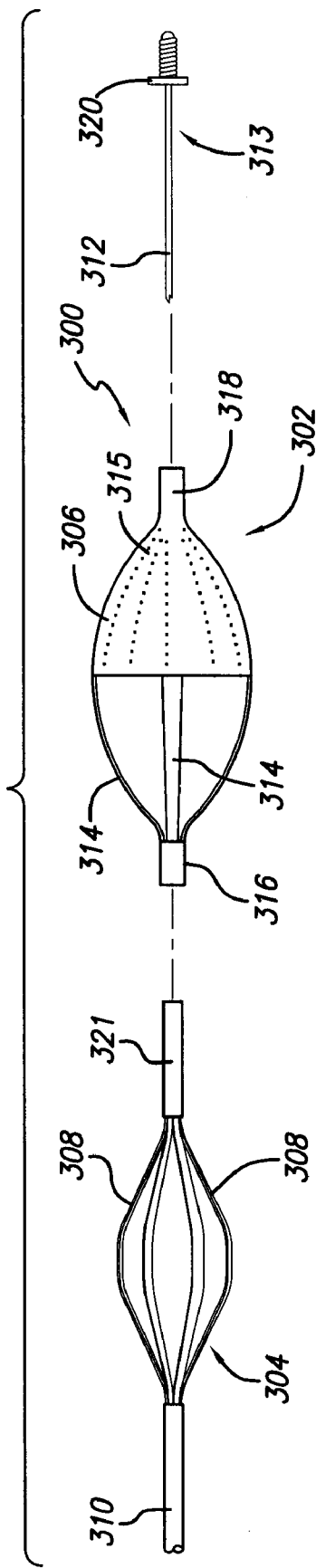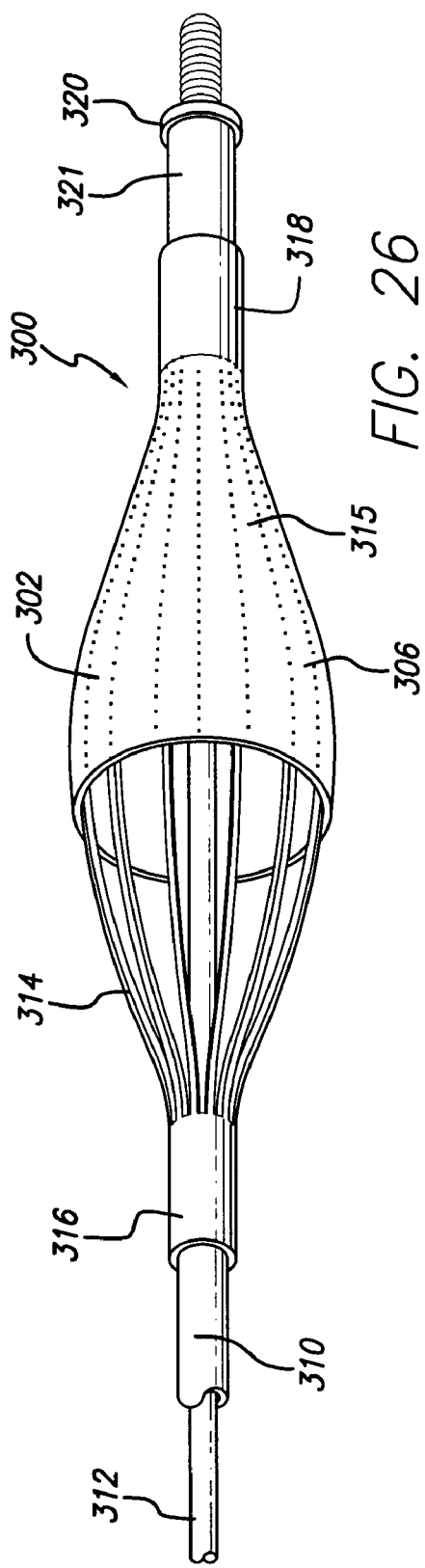
FIG. 25
FIG. 26

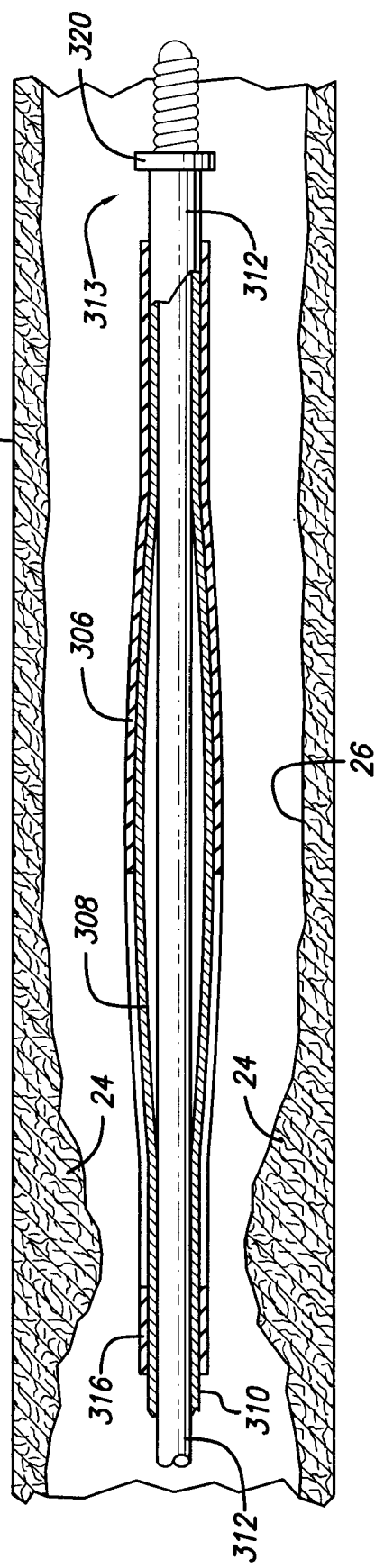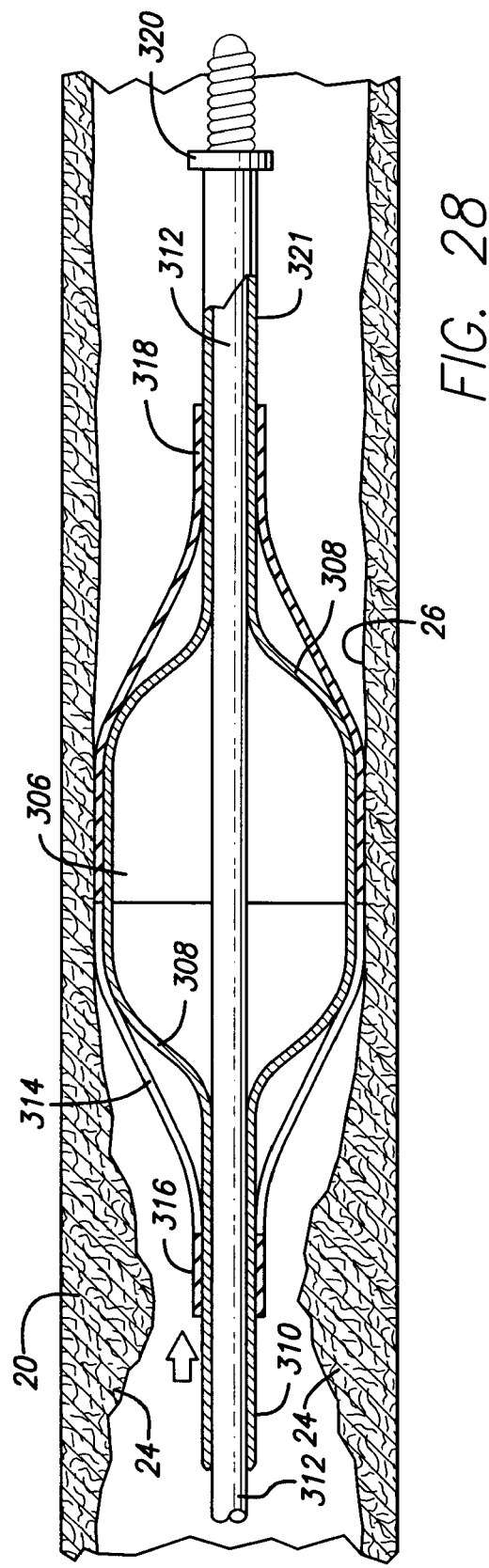

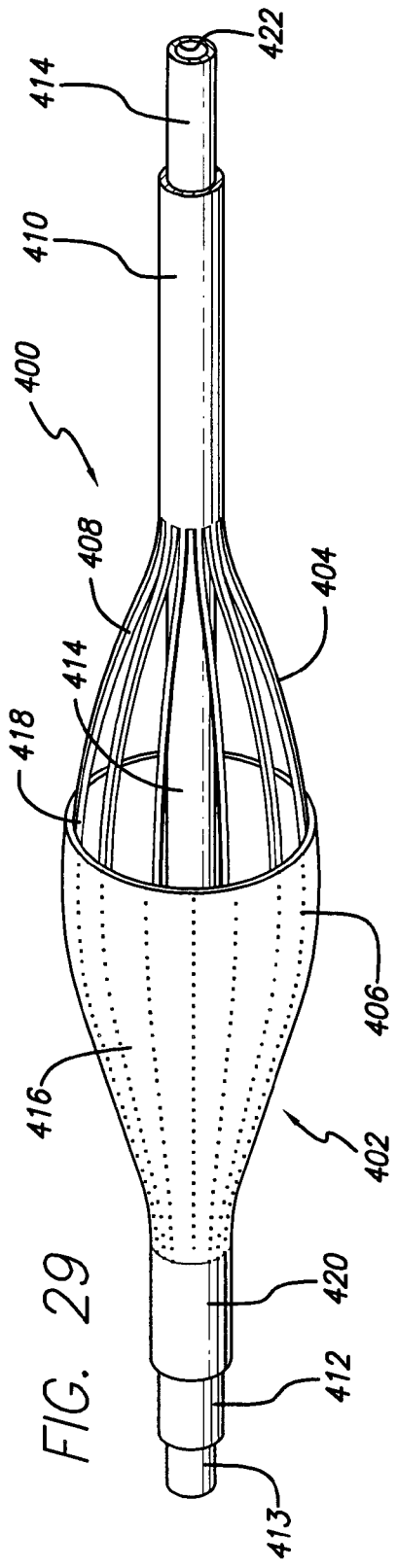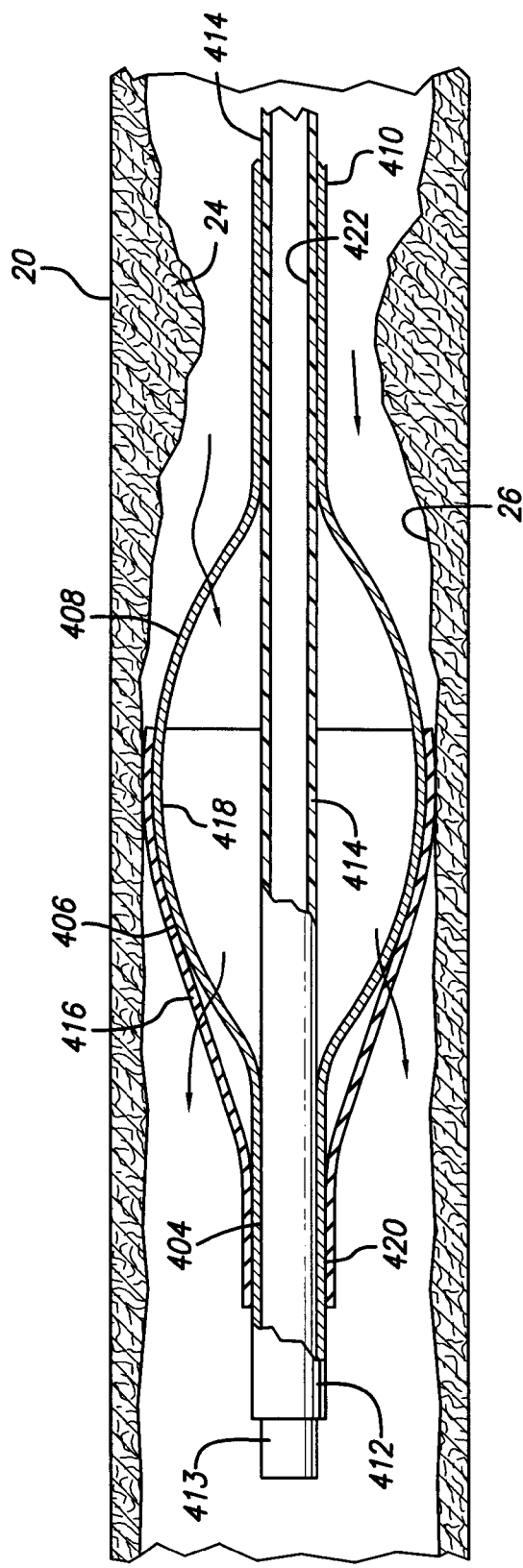

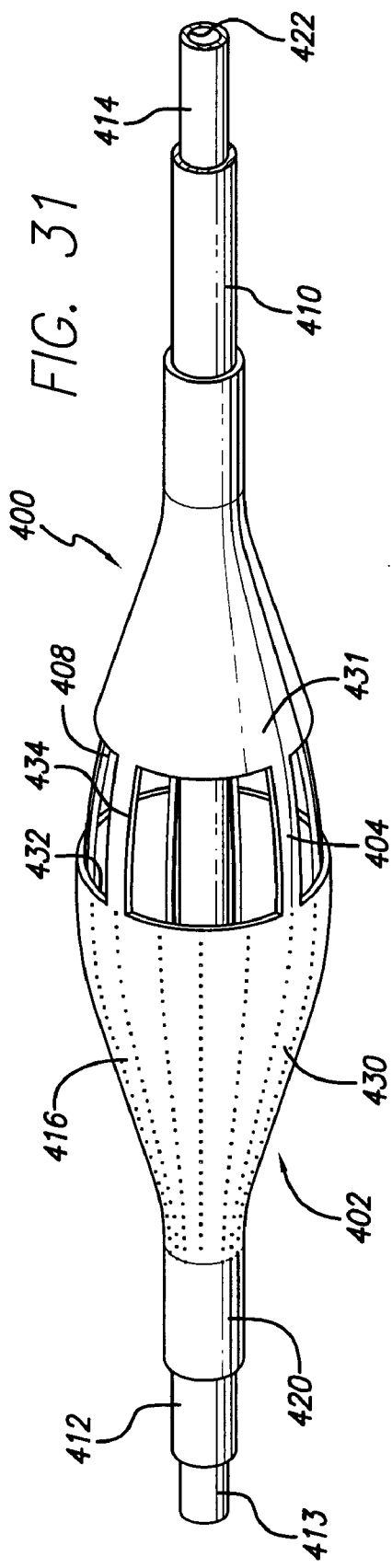
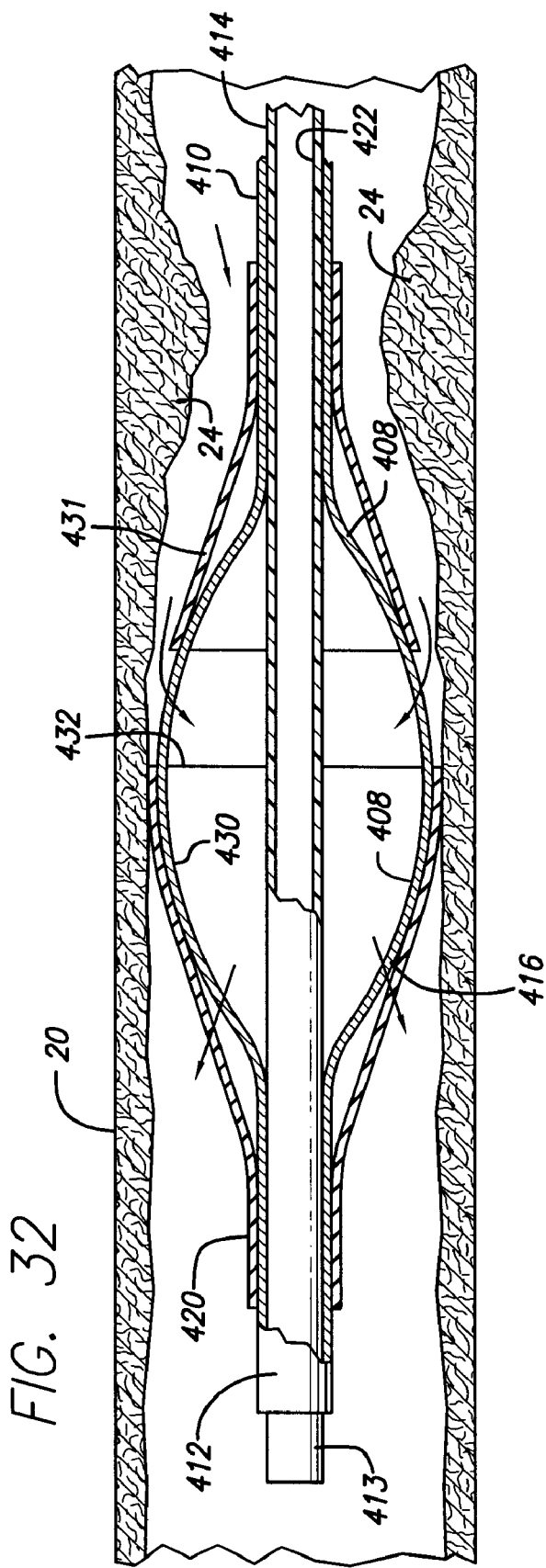

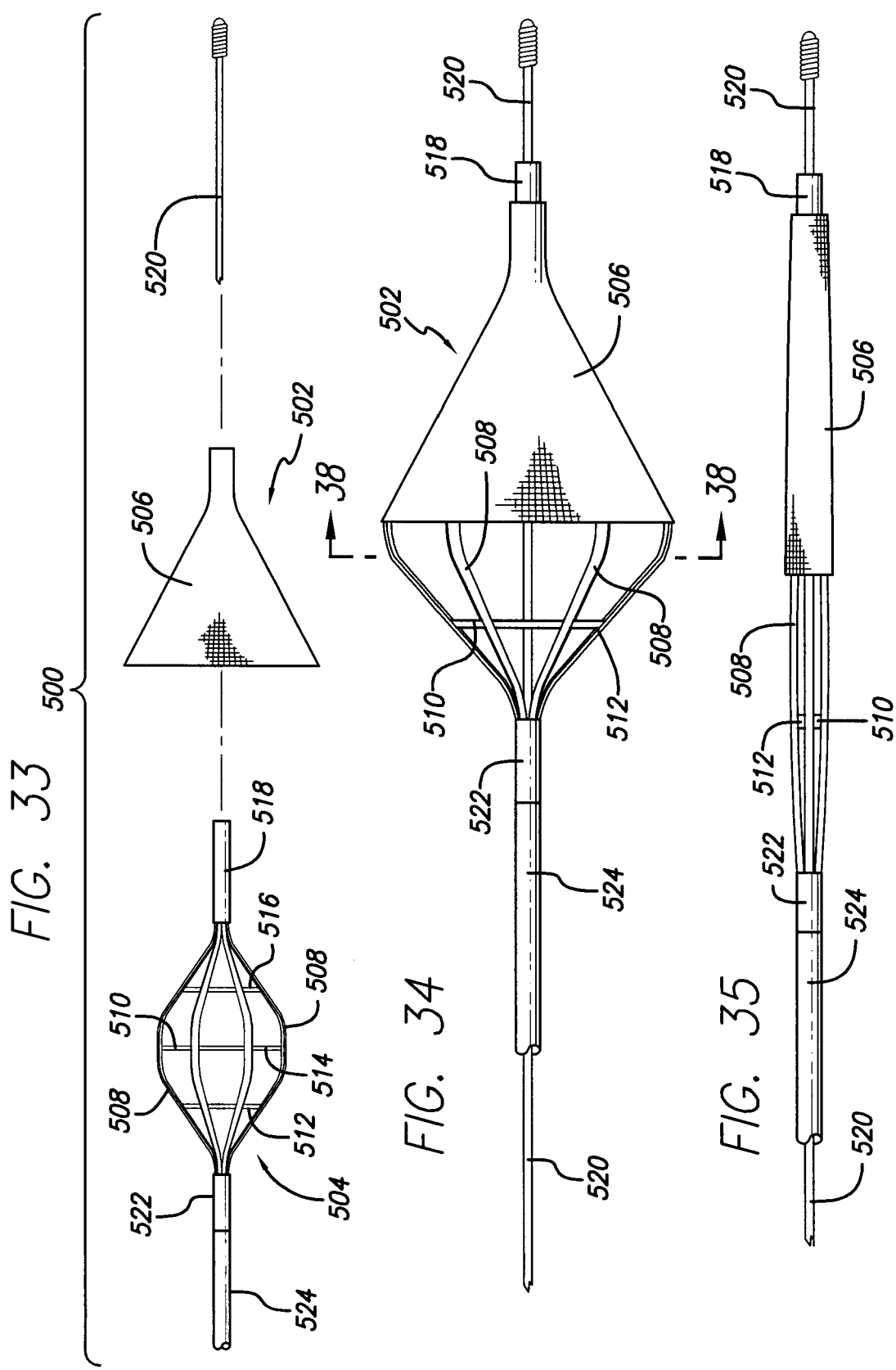

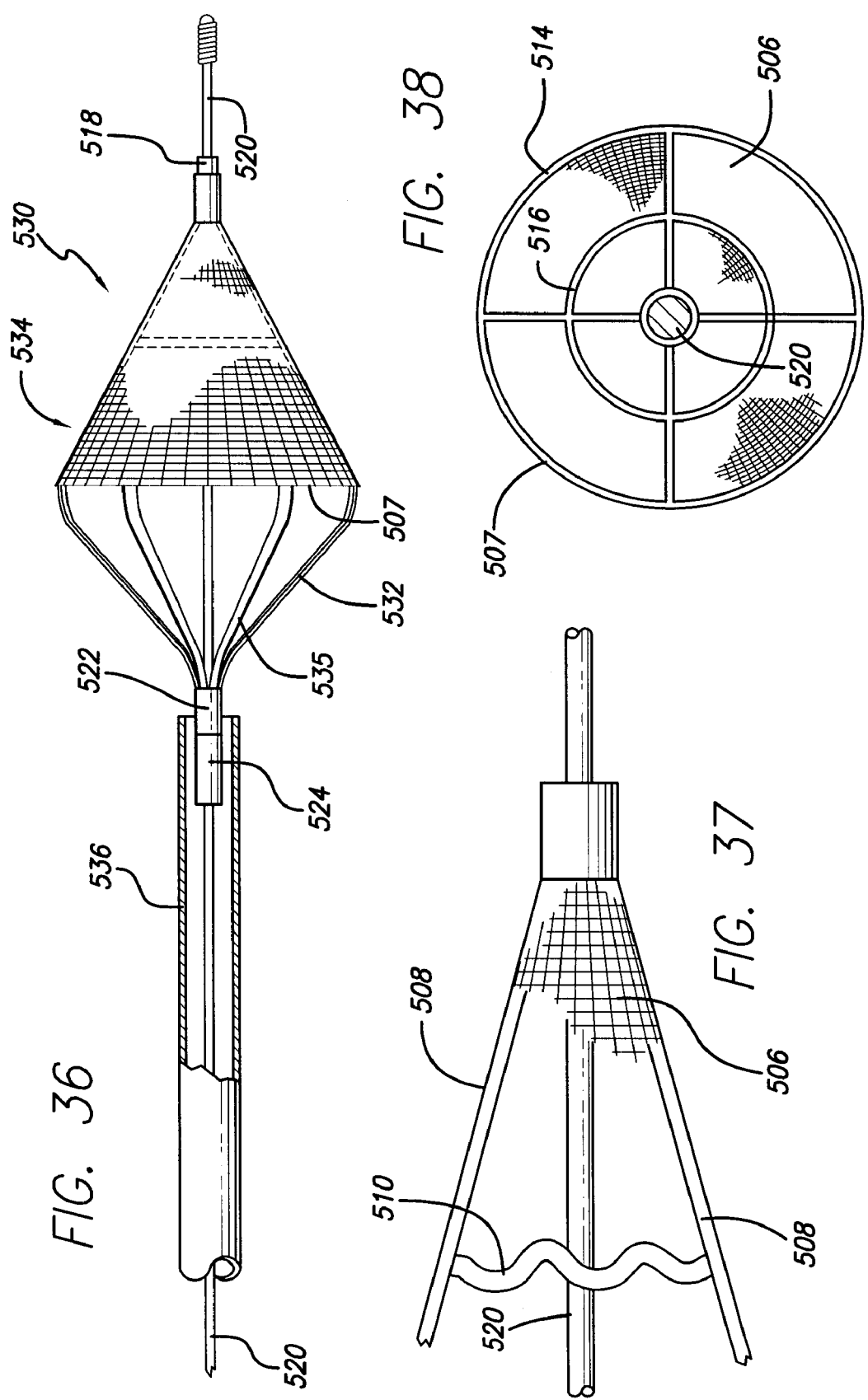

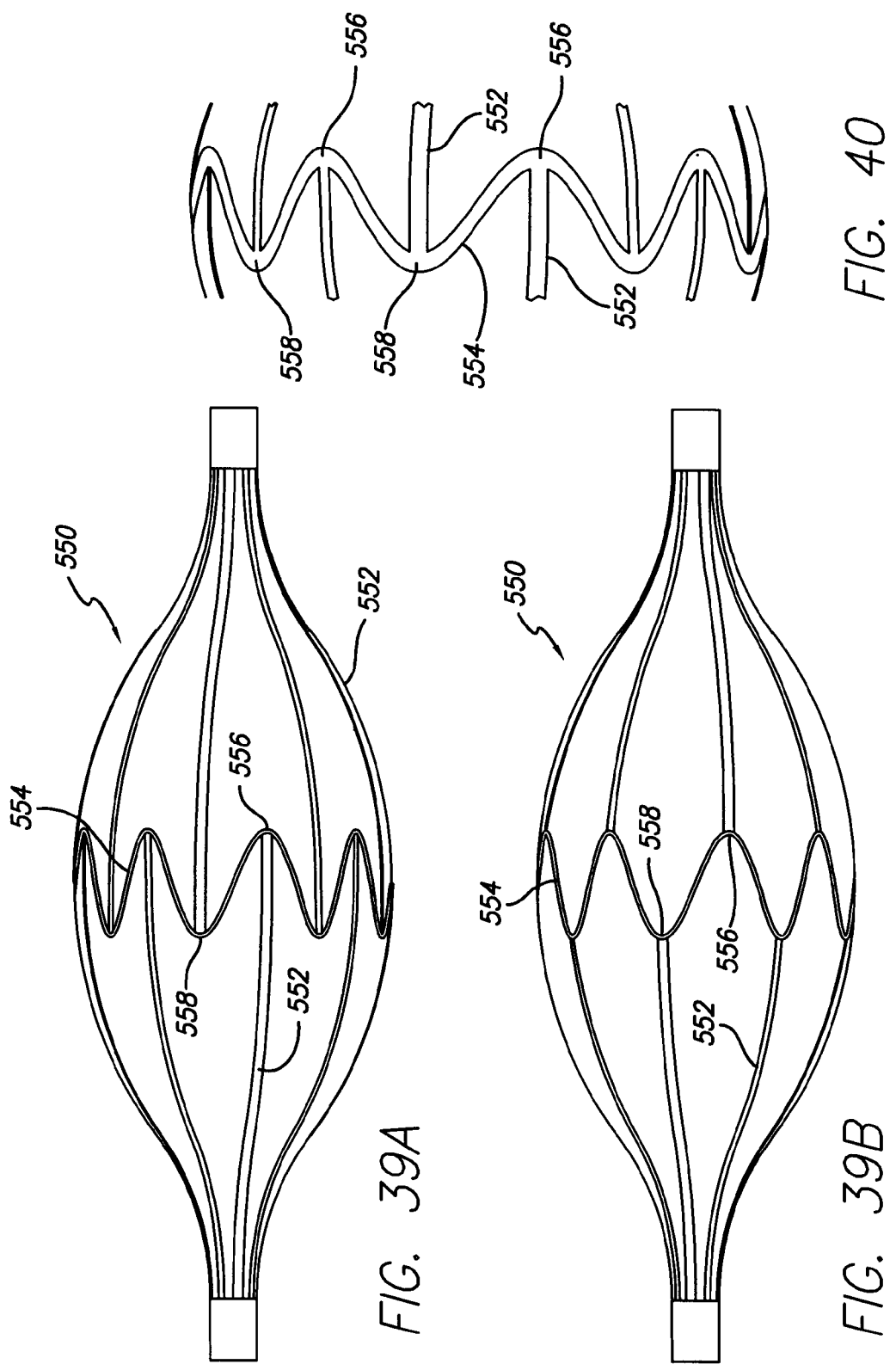

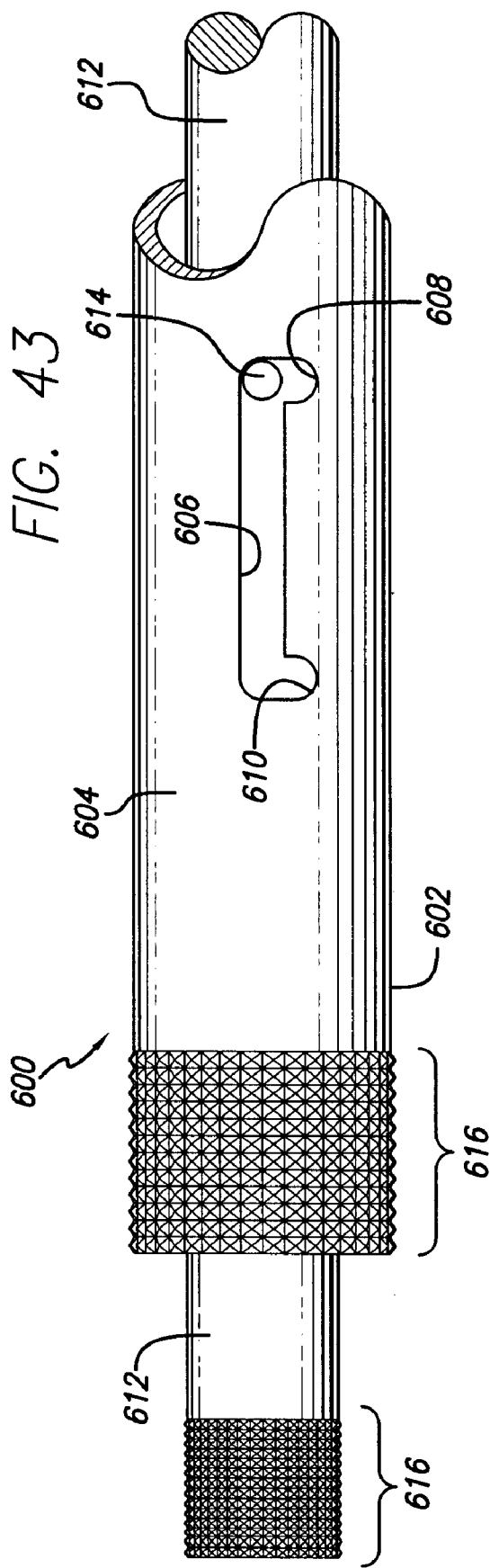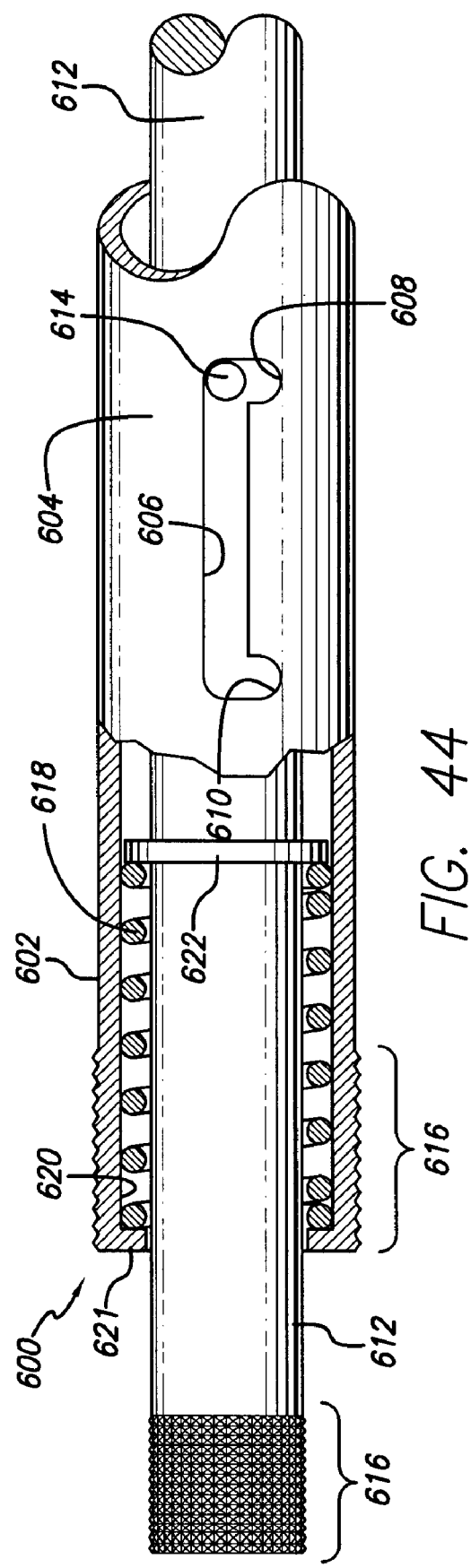

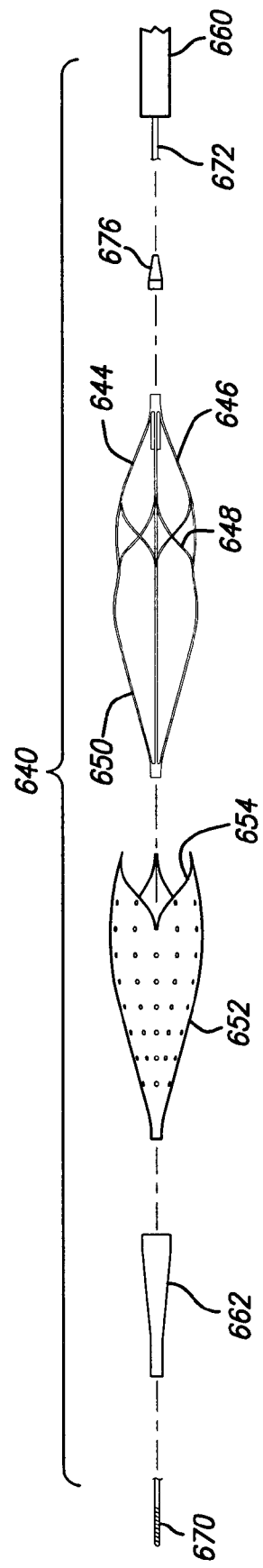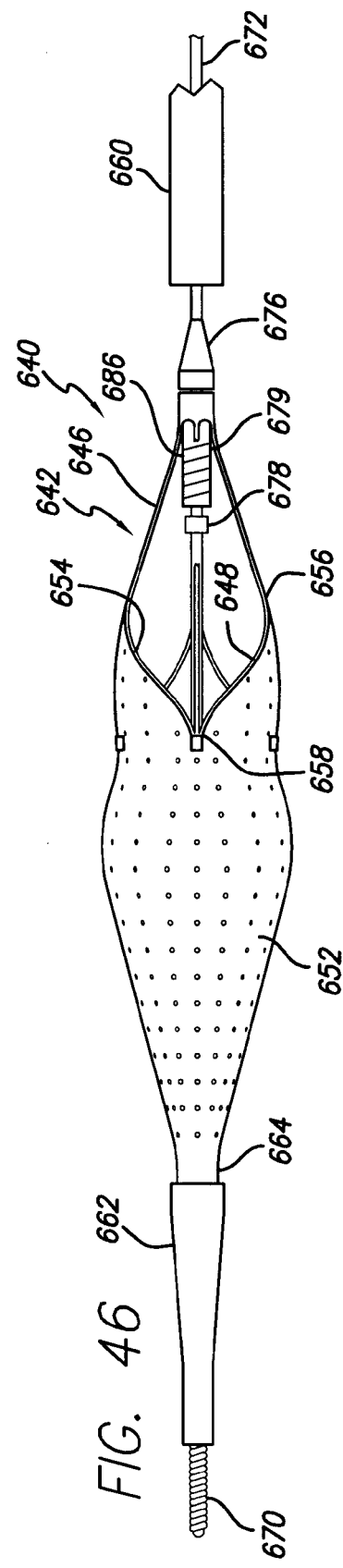
FIG. 45
FIG. 46
FIG. 47

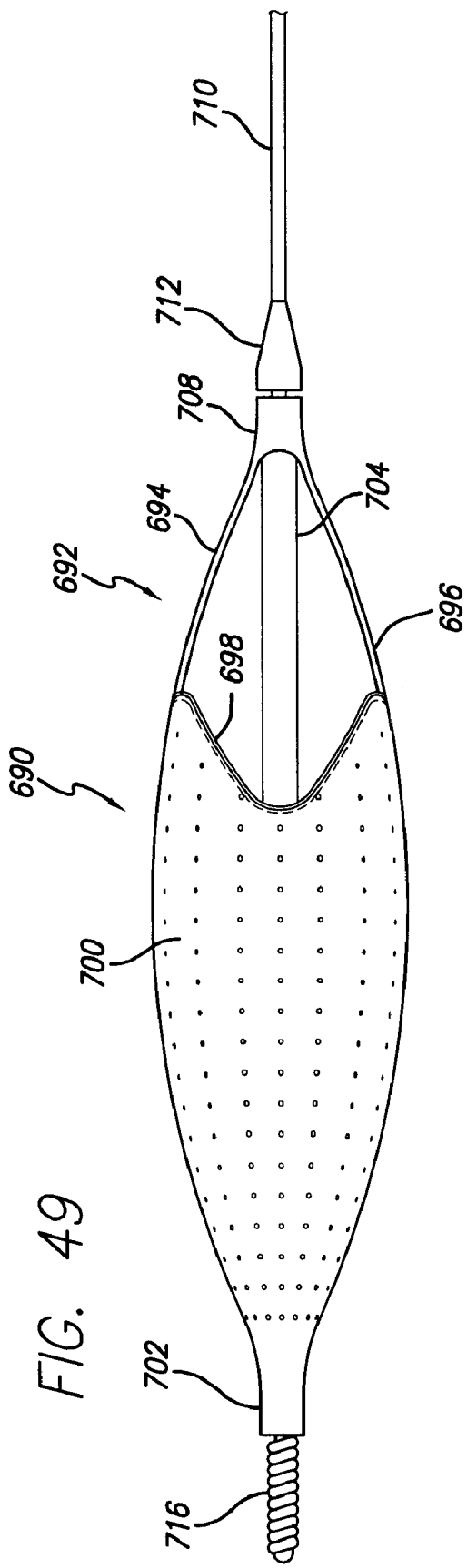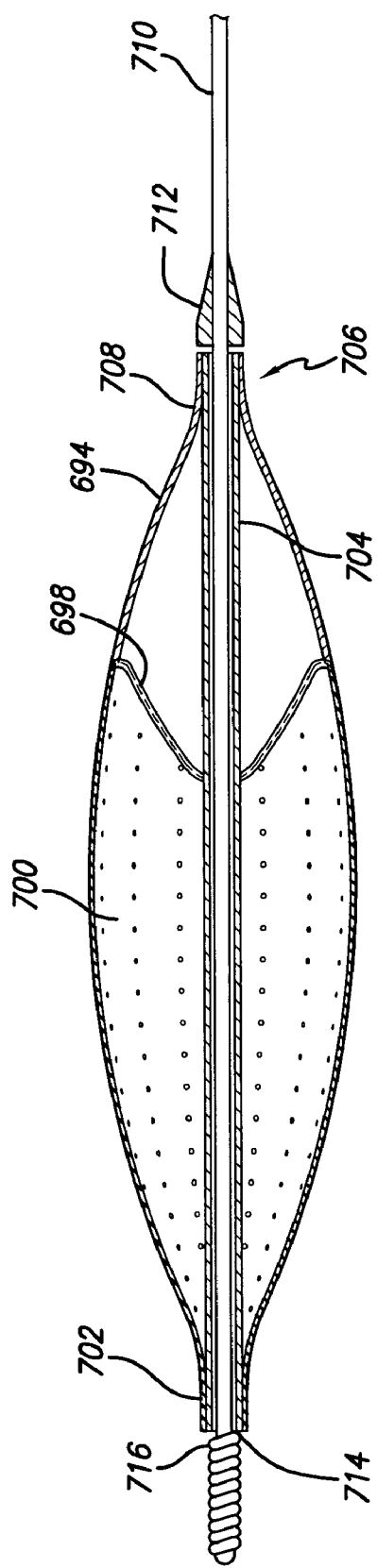

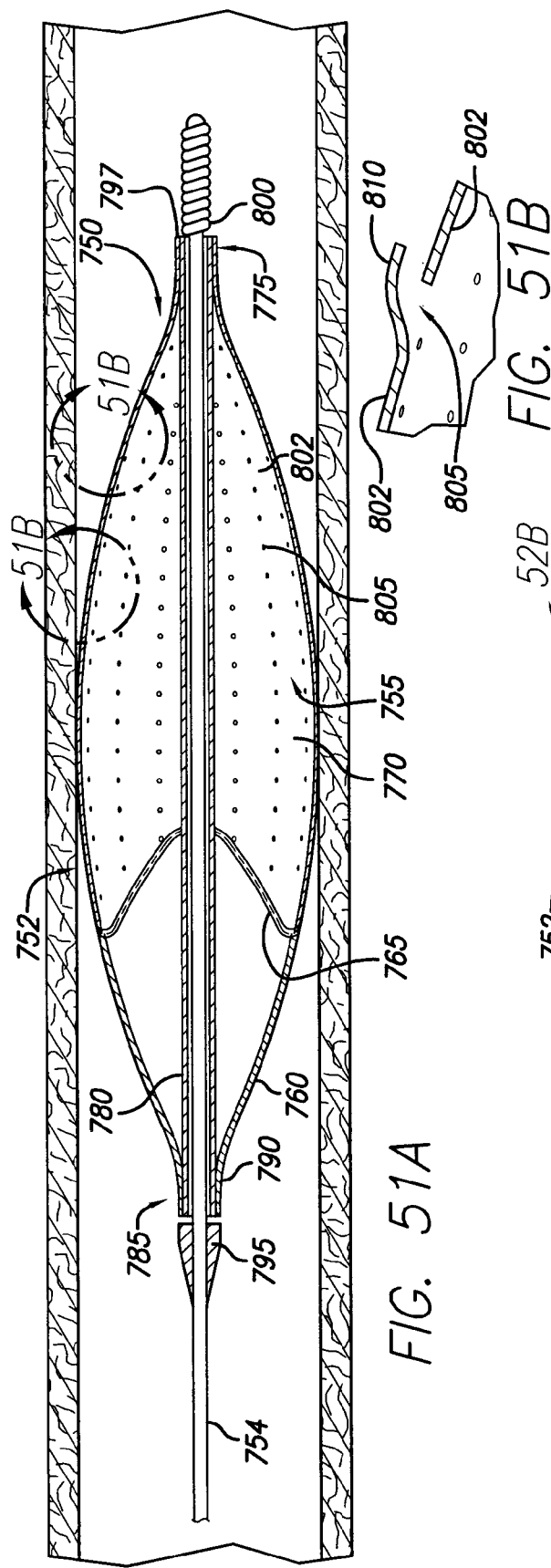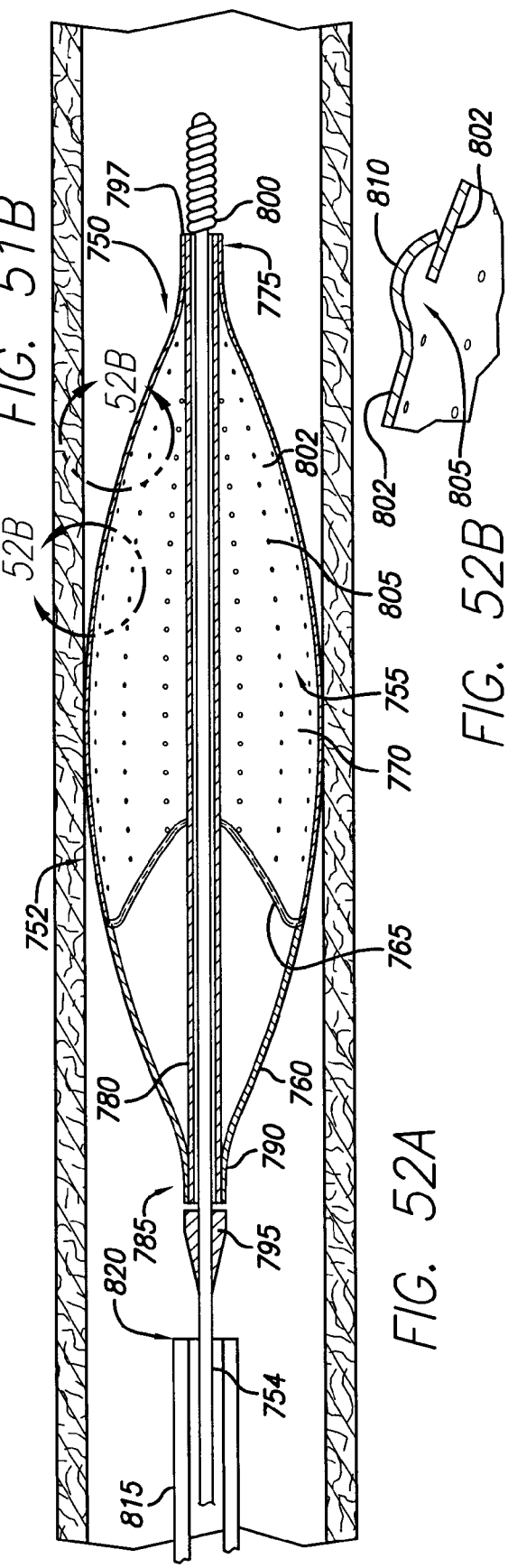

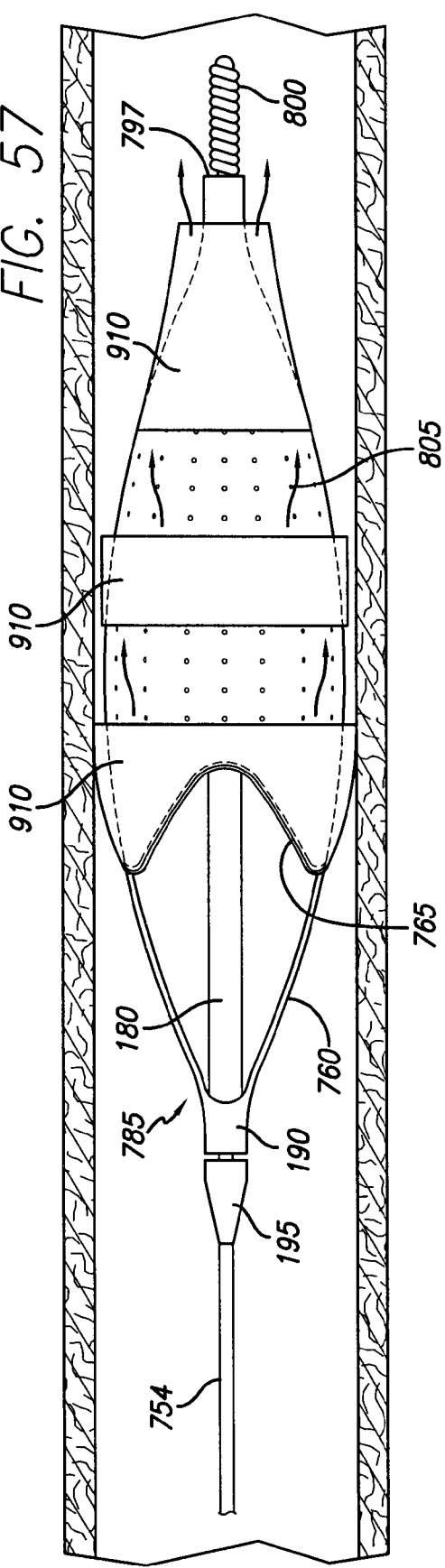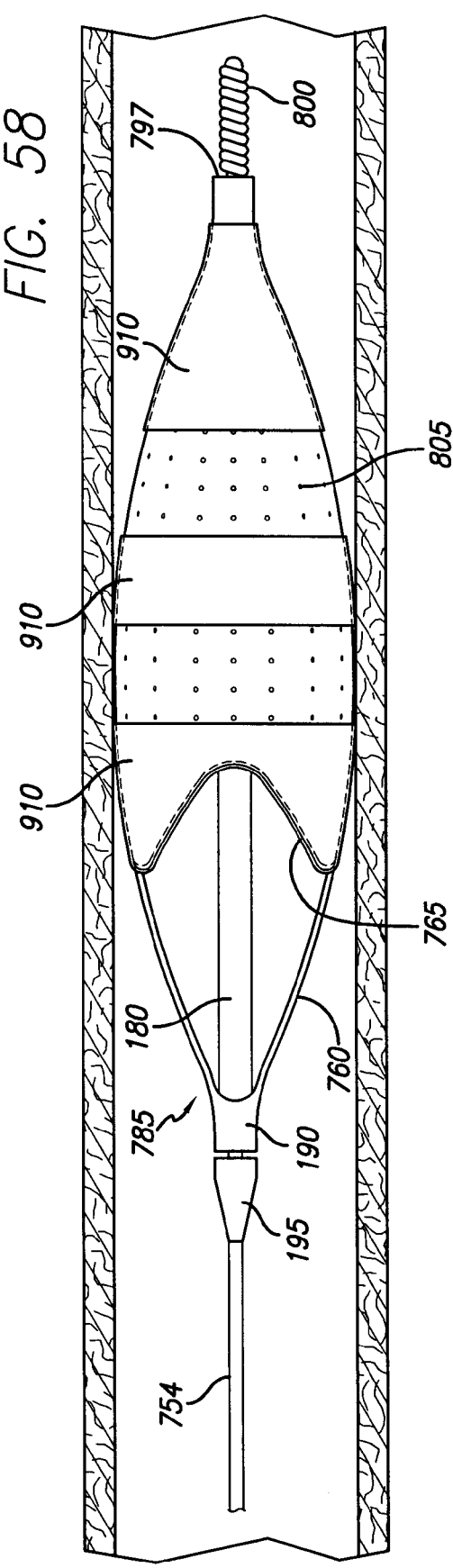

EMBOLIC PROTECTION DEVICES ONE WAY POROUS MEMBRANE

This application is related to application Ser. No. 09/490,319 filed Jan. 24, 2000, and application Ser. No. 09/476,159 filed Dec. 30, 1999, which are assigned to the same Assignee as the present application.

BACKGROUND OF THE INVENTION

The present invention relates generally to filtering devices and systems which can be used when an interventional procedure is being performed in a stenosed or occluded region of a blood vessel to capture embolic material that may be created and released into the bloodstream during the procedure. The embolic filtering devices and systems of the present invention are particularly useful when performing balloon angioplasty, stenting procedures, laser angioplasty or atherectomy in critical vessels, particularly in vessels such as the carotid arteries, where the release of embolic debris into the bloodstream can occlude the flow of oxygenated blood to the brain or other vital organs, which can cause devastating consequences to the patient. While the embolic protection devices and systems of the present invention are particularly useful in carotid procedures, the inventions can be used in conjunction with any vascular interventional procedure in which there is an embolic risk.

A variety of non-surgical interventional procedures have been developed over the years for opening stenosed or occluded blood vessels in a patient caused by the build up of plaque or other substances on the wall of the blood vessel. Such procedures usually involve the percutaneous introduction of the interventional device into the lumen of the artery, usually through a catheter. In typical carotid PTA procedures, a guiding catheter or sheath is percutaneously introduced into the cardiovascular system of a patient through the femoral artery and advanced through the vasculature until the distal end of the guiding catheter is in the common carotid artery. A guide wire and a dilatation catheter having a balloon on the distal end are introduced through the guiding catheter with the guide wire sliding within the dilatation catheter. The guide wire is first advanced out of the guiding catheter into the patient's carotid vasculature and is directed across the arterial lesion. The dilatation catheter is subsequently advanced over the previously advanced guide wire until the dilatation balloon is properly positioned across the arterial lesion. Once in position across the lesion, the expandable balloon is inflated to a predetermined size with a radiopaque liquid at relatively high pressures to radially compress the atherosclerotic plaque of the lesion against the inside of the artery wall and thereby dilate the lumen of the artery. The balloon is then deflated to a small profile so that the dilatation catheter can be withdrawn from the patient's vasculature and the blood flow resumed through the dilated artery. As should be appreciated by those skilled in the art, while the above-described procedure is typical, it is not the only method used in angioplasty.

Another procedure is laser angioplasty which utilizes a laser to ablate the stenosis by super heating and vaporizing the deposited plaque. Atherectomy is yet another method of treating a stenosed blood vessel in which cutting blades are rotated to shave the deposited plaque from the arterial wall. A vacuum catheter is usually used to capture the shaved plaque or thrombus from the blood stream during this procedure.

In the procedures of the kind referenced above, abrupt reclosure may occur, or restenosis of the artery may develop over time, which may require another angioplasty procedure, a surgical bypass operation, or some other method of repairing or strengthening the area. To reduce the likelihood of the occurrence of abrupt reclosure and to strengthen the area, a physician can implant an intravascular prosthesis for maintaining vascular patency, commonly known as a stent, inside the artery across the lesion. The stent is crimped tightly onto the balloon portion of the catheter and transported in its delivery diameter through the patient's vasculature. At the deployment site, the stent is expanded to a larger diameter, often by inflating the balloon portion of the catheter.

Prior art stents typically fall into two general categories of construction. The first type of stent is expandable upon application of a controlled force, as described above, through the inflation of the balloon portion of a dilatation catheter which, upon inflation of the balloon or other expansion means, expands the compressed stent to a larger diameter to be left in place within the artery at the target site. The second type of stent is a self-expanding stent formed from, for example, shape memory metals or super-elastic nickel-titanum (NiTi) alloys, which will automatically expand from a collapsed state when the stent is advanced out of the distal end of the delivery catheter into the body lumen. Such stents manufactured from expandable heat sensitive materials allow for phase transformations of the material to occur, resulting in the expansion and contraction of the stent.

The above non-surgical interventional procedures, when successful, avoid the necessity of major surgical operations. However, there is one common problem which can become associated with all of these non-surgical procedures, namely, the potential release of embolic debris into the bloodstream that can occlude distal vasculature and cause significant health problems to the patient. For example, during deployment of a stent, it is possible that the metal struts of the stent can cut into the stenosis and shear off pieces of plaque which become embolic debris that can travel downstream and lodge somewhere in the patient's vascular system. Pieces of plaque material can sometimes dislodge from the stenosis during a balloon angioplasty procedure and become released into the bloodstream. Additionally, while complete vaporization of plaque is the intended goal during a laser angioplasty procedure, quite often particles are not fully vaporized and thus enter the bloodstream. Likewise, not all of the emboli created during an atherectomy procedure may be drawn into the vacuum catheter and, as a result, enter the bloodstream as well.

When any of the above-described procedures are performed in the carotid arteries, the release of emboli into the circulatory system can be extremely dangerous and sometimes fatal to the patient. Debris that is carried by the bloodstream to distal vessels of the brain can cause these cerebral vessels to occlude, resulting in a stroke, and in some cases, death. Therefore, although cerebral percutaneous transluminal angioplasty has been performed in the past, the number of procedures performed has been limited due to the justifiable fear of causing an embolic stroke should embolic debris enter the bloodstream and block vital downstream blood passages.

Medical devices have been developed to attempt to deal with the problem created when debris or fragments enter the circulatory system following vessel treatment utilizing any one of the above-identified procedures. One approach which has been attempted is the cutting of any debris into minute sizes which pose little chance of becoming occluded in major vessels within the patient's vasculature. However, it is often difficult to control the size of the fragments which are formed, and the potential risk of vessel occlusion still exists, making such a procedure in the carotid arteries a high-risk proposition.

Other techniques which have been developed to address the problem of removing embolic debris include the use of catheters with a vacuum source which provides temporary suction to remove embolic debris from the bloodstream. However, as mentioned above, there have been complications with such systems since the vacuum catheter may not always remove all of the embolic material from the bloodstream, and a powerful suction could cause problems to the patient's vasculature. Other techniques which have had some limited success include the placement of a filter or trap downstream from the treatment site to capture embolic debris before it reaches the smaller blood vessels downstream. However, there have been problems associated with filtering systems, particularly during the expansion and collapsing of the filter within the body vessel. If the filtering device does not have a suitable mechanism for closing the filter, there is a possibility that trapped embolic debris can backflow through the inlet opening of the filter and enter the blood-stream as the filtering system is being collapsed and removed from the patient. In such a case, the act of collapsing the filter device may actually squeeze trapped embolic material through the opening of the filter and into the bloodstream.

Occasionally when using a filtering system to trap embolic material it may be necessary to remove trapped embolic material from the filter while the filter remains expanded an in place in the patient's vasculature. Typically, an aspiration catheter is placed on the guide wire and the distal end of the catheter is positioned adjacent the filter. A vacuum is applied to the proximal end of the aspiration catheter to draw the embolic material from the filter into the distal end of the aspiration catheter. One problem that occurs during this procedure is that the suction applied to the trapped embolic material by the distal end of the aspiration catheter may result in excessive back flow of blood through the filter, reducing the efficiency of the removal procedure and prolonging the time necessary to remove embolic material from the filter.

Many of the prior art filters which can be expanded within a blood vessel are attached to the distal end of a guide wire or guide wire-like tubing which allows the filtering device to be placed in the patient's vasculature when the guide wire is manipulated in place. Once the guide wire is in proper position in the vasculature, the embolic filter can be deployed within the vessel to capture embolic debris. The guide wire can then be used by the physician to deliver interventional devices, such as a balloon angioplasty dilatation catheter or a stent, into the area of treatment. When a combination of embolic filter and guide wire is utilized, the proximal end of a guide wire can be rotated by the physician, usually unintentionally, when the interventional device is being delivered over the guide wire in an over-the-wire fashion. If the embolic filter is rigidly affixed to the distal end of the guide wire, and the proximal end of the guide wire is twisted or rotated, that rotation will be translated along the length of the guide wire to the embolic filter, which can cause the filter to rotate or move within the vessel and possibly cause trauma to the vessel wall. Additionally, it is possible for the physician to accidentally collapse or displace the deployed filter should the guide wire twist when the interventional device is being delivered over the guide wire. Moreover, a shockwave (vibratory motion) caused by the exchange of the delivery catheter or interventional devices along the guide wire can jar the deployed filtering device and can possibly result in trauma to the blood vessel. These types of occurrences during the interventional procedure are undesirable since they can cause trauma to the vessel which is detrimental to the patient's health and/or cause the deployed filter to be displaced within the vessel which may result in some embolic debris flowing past the filter into the downstream vessels.

What has been needed is a reliable filtering device and system for use when treating stenosis in blood vessels which helps prevent the risk associated when embolic debris that can cause blockage in vessels at downstream locations is released into the bloodstream. The device should be capable of filtering any embolic debris which may be released into the bloodstream during the treatment and safely contain the debris until the filtering device is to be collapsed and removed from the patient's vasculature. The device should be relatively easy for a physician to use and should provide a failsafe filtering device which captures and removes any embolic debris from the bloodstream. The device should also be capable of providing for one way flow of blood through the device that allows blood to flow through the device during normal usage, but which prevents, in whole or in part, backwards flow through the filtering device when trapped embolic material is aspirated from the device when it is positioned within the patient's vasculature. Moreover, such a device should be relatively easy to deploy and remove from the patient's vasculature. The inventions disclosed herein satisfy these and other needs.

SUMMARY OF THE INVENTION

The present invention provides filtering devices and systems for capturing embolic debris in a blood vessel created during the performance of a therapeutic interventional procedure, such as a balloon angioplasty or stenting procedure, in order to prevent the embolic debris from blocking blood vessels downstream from the interventional site. The filtering devices of the present invention include a filter assembly providing for controlled back flow of blood through the device such that embolic material trapped within the filter assembly during usage may be aspirated from the filter using suction provided by an aspiration catheter that is positioned adjacent the filter assembly when it is positioned within a patient's vasculature. Thus the filtering device of the present invention may prevent back flow of blood through the device, or a controlled amount of back flow may be permitted.

The devices and systems of the present invention are particularly useful while performing an interventional procedure in critical arteries, such as the carotid arteries, in which vital downstream blood vessels can easily become blocked with embolic debris, including the main blood vessels leading to the brain. When used in carotid procedures, the present invention minimizes the potential for a stroke occurring during the procedure. As a result, the present invention provides the physician with a higher degree of confidence that embolic debris is being properly collected and removed from the patient's vasculature during the interventional procedure.

An embolic protection device and system made in accordance with the present invention includes an expandable filtering assembly which is affixed to the distal end of a tubular shaft member, such as a guide wire. The filtering assembly includes an expandable strut assembly made from a self-expanding material, such as nickel-titanium (NiTi) alloy or spring steel, and includes a number of outwardly extending struts which are capable of self-expanding from a contracted or collapsed position to an expanded or deployed position within the patient's vasculature. A filter element made from an embolic capturing media is attached to the expandable strut assembly and moves from the collapsed position to the expanded position via the movement of the expandable struts. This expandable strut assembly is affixed to the guide wire in such a manner that the entire filtering assembly rotates or "spins" freely on the guide wire to prevent the filtering assembly from being rotated after being deployed within the patient's vasculature. In this manner, any accidental or intentional rotation of the proximal end of the guide wire is not translated to the deployed filtering assembly, which will remain stationary within the patient's vasculature and, as such, the threat of trauma to the vessel wall and displacement of the filter caused by the rotation and/or manipulation of the guide wire can be virtually eliminated.

The expandable struts of the strut assembly can be biased to remain in their expanded position until an external force placed on the struts to collapse and maintain the struts in their contracted or collapsed position is removed. This is done through the use of a restraining sheath which is placed over the filtering assembly in a coaxial fashion to maintain the strut assembly in its collapsed position. The composite guide wire and filtering assembly, with the restraining sheath placed over the filtering assembly, can then be placed into the patient's vasculature. Once the physician properly manipulates the guide wire into the target area, the restraining sheath can be retracted off of the expandable strut assembly to deploy the struts into their expanded position. This can be easily performed by the physician by simply retracting the proximal end of the restraining sheath (which is located outside of the patient) along the guide wire. Once the restraining sheath is retracted, the self-expanding properties of the strut assembly cause the struts to move radially outward away from the guide wire to contact the wall of the blood vessel. Again, as the struts expand radially, so does the filter element which will now be in place to collect any embolic debris that may be released into the bloodstream as the physician performs the interventional procedure. The filter sub-assembly could be bonded to the core wire at both distal and proximal ends of the embolic protection device. The core wire could be made from stainless steel or shaped memory biocompatible materials. The guide wire with the embolic protection device could be loaded into a delivery sheath. The delivery sheath could be torqued, steering the device into the intended vessel site.

The filtering assembly can be rotatably affixed to the guide wire by rotatably attaching the proximal end of the filtering assembly to the guide wire. The distal end of the strut assembly can move longitudinally along the guide wire and is also rotatable on the guide wire as well. This allows the strut assembly to move between its collapsed and expanded positions while still allowing the entire filtering assembly to freely rotate or "spin" about the guide wire. This attachment of the proximal end of the strut assembly to the guide wire allows the restraining sheath to be retracted from the filtering assembly and permits a recovery sheath to be placed over the expanded strut assembly to move the strut assembly back to the collapsed position when the embolic protection device is to be removed from the patient's vasculature.

The filtering assembly also may include a dampening element or member which is utilized to absorb some of the shockwave (vibratory motion) that may be transmitted along the length of the guide wire during the handling of the guide wire by the physician. Since a sudden shock to the filtering assembly can cause the filter to scrape the wall of the blood vessel or become displaced in the vessel, the dampening member acts much like a "shock absorber" to absorb some of the shock and prevent the transmission of the shock force to the filtering assembly. This shock can be produced via a number of ways, for example, through the exchange of interventional devices along the guide wire. Also, when the restraining sheath is removed from the filtering assembly, a shockwave can be created if the self-expanding struts open too quickly. As a result of utilizing the dampening member, shock and trauma to the patient's vasculature are minimized and the chances of displacing the filter are virtually eliminated. In one particular embodiment of the dampening member, a helical spring is formed on the proximal end of the expandable strut assembly to provide dampening to the assembly. Other methods of obtaining dampening can be utilized, such as attaching a spring or elastomeric member to the strut assembly.

The expandable strut assembly made in accordance with the present invention may be made from a length of tubing (also known as a "hypotube") made from a shape memory alloy or other self-deploying material. Stainless steel or other biocompatible metals or polymers can be utilized to form the struts of the assembly. One preferable material is a shape memory alloy such as nickel-titanium (NiTi). The individual struts of the expandable strut assembly are formed on the length of hypotube by selectively removing material from the tubing to form the particular size and shape of the strut. For example, the wall of the hypotube can be laser cut with slots to form the individual struts. Small tabs can also be lazed into the tubing along the strut which can be used to hold the filter member in place. By selectively removing portions of the hypotube by a high precision laser, similar to lasers utilized in the manufacturer of stents, one can achieve a very precise and well defined strut shape and length. In one particular embodiment of the present invention, the pattern of the material to be removed from the hypotubing can be a repeating diamond-shaped which creates a strut pattern in the form of two inverted triangles meshed together. This particular strut pattern provides greater strength along the strut where it would have a tendency to break or become weakened. Such a strut pattern also provides for a more natural bending position for each strut, allowing the expandable strut assembly to open and close more uniformly. In one particular pattern, the strut pattern requires the removal of a repeating truncated diamond pattern by laser or other means to create the shape of the strut. In this particular pattern, each strut has a relatively straight center section formed between two inverted triangles, somewhat similar to the strut pattern described above. This particular strut pattern provides an expanded center section which allows the struts to expand to a greater volume, which helps in the capture of emboli by allowing a larger filter to be placed on the strut assembly. The center section located between the two inverted triangles also provides a sufficient working area to attach the filter element onto the strut assembly. These same features can be accomplished by curved sections which have a reduced width in the center section.

The embolic protection device may also include a filtering assembly with a strut assembly which is not self-expanding, but utilizes the application of a force on the proximal and distal ends of the strut assembly to deploy and collapse the assembly. In this particular form of the invention, the embolic protection device includes an inner shaft member and an outer tubular member which is coaxially disposed over the inner shaft member. The distal end of the expandable strut assembly can be attached to the inner shaft member with the proximal end of the strut assembly being attached to the distal end of the outer tubular member. When there is relative movement between the inner shaft member and outer tubular member, a force is created which is imparted to the expandable strut assembly to cause the struts to either contract or expand. For example, in the embodiment described above, when the outer tubular member and inner shaft member are moved relative to each other to produce an inward force acting on the proximal and distal ends of the strut assembly, the force causes the expandable struts to move from the collapsed position into the expanded position. Thereafter, when the strut assembly is to be collapsed, the outer tubular member and inner shaft member can be moved relative to each other to create an outward force acting on the proximal and distal end of the strut assembly to cause the expanded struts to move back to their collapsed position. A physician can easily manipulate the proximal ends of the inner shaft member and outer tubular member to deploy and collapse the filtering assembly as needed. The filtering assembly could be self-expanding with the movement of the inner and outer members providing the means for expanding and collapsing the assembly without the need for an outer sheath.

The inner shaft member can be a guide wire which can be utilized to move the filtering assembly directly into position downstream from the lesion for capturing any embolic debris which may be released into the bloodstream. The inner shaft member could also be a elongated tubular member which has an inner lumen that can track along a guide wire once the guide wire has been maneuvered into position into the patient's vasculature. The entire embolic protection device can then be delivered to the desired location over the guide wire using over-the-wire techniques.

The filtering element utilized in conjunction with the embolic protection device can take on many different forms as are disclosed herein. In one particular embodiment, the filter includes a proximal cone section which expands to the diameter of the artery in which the embolic protection device is to be deployed. This proximal cone section funnels blood flow and embolic debris into a main or central filter located distal to the proximal cone section. This proximal cone may or may not provide filtering itself. Its primary function is flow direction and its ability to collapse and expand with the expandable struts of the strut assembly. A main or central filter may comprise an elongated tubular shaped member is located distal to the proximal cone section. It is integral with the distal end of the proximal cone section and provides a large filtering area that acts as a storage reservoir for holding embolic material. Ideally, it is sized so that it receives any and all of the embolic material which it is to be filtered by the embolic protection device. It includes a number of perfusion openings which allow blood to pass through but retain embolic material. The central filter may not be collapsible or expandable, but rather may be made somewhat rigid and has an outer diameter large enough to provide a storage reservoir for holding embolic material yet can be withdrawn and delivered through the particular guiding catheter utilized to deploy the embolic protection device into the patient's vasculature. The central filter also could be made from collapsible material, but should have an outer diameter which is large enough to provide an adequate storage reservoir yet can be withdrawn through the guiding catheter as well. Although this central filter may have a substantially fixed diameter, it can also be tapered and should have an outer diameter small enough to fit through the inner diameter of the specific guiding catheter utilized to deploy the device.

The filtering element may also be formed to include flaps or other valve-like structures to provide for controlled back flow of blood through the filtering element. In one embodiment, the filtering element includes a plurality of openings or holes that allow blood to escape the interior of the filtering element leaving the embolic material trapped within the filtering element. One or more of the openings or holes may be occluded by a flexible flap such that when blood flows through the filter during normal usage, the flap does not seal the hole but instead allows for free flow of blood through the opening or hole. When a suction is applied to the interior of the filtering element to aspirate the trapped embolic material, however, the reduction of pressure within the interior of the filtering element due to the aspiration causes the flexible flap to close against the exterior of the filtering element, sealing the opening or hole and preventing backwards flow of blood through the opening or hole and into the interior of the filtering element. While in one embodiment, all of the openings or holes formed in the filtering element may be capable of being occluded by flexible flaps, in other embodiments only a portion of the openings or holes may be associated with flexible flaps, leaving a portion of the openings or holes that are not occluded by a flap during aspiration, thus providing for a predetermined, controlled amount of backwards flow into the interior of the filtering element during aspiration of trapped embolic material. The flap or flaps may be attached to the exterior surface of the filtering element or assembly using a suitable adhesive or other bonding means, such as ultrasonic welding, or the flap or flaps may be formed as an integral part of the filtering element.

In another embodiment, the filtering device may include a sheath or sleeve covering the exterior surface of the filtering element. The sheath or sleeve is secured to the filtering element in such a manner as to allow blood to flow through holes or other openings in the filtering element without obstruction during normal usage. Aspirating embolic material from the filtering device, however, results in the sheath or sleeve being drawn down onto the surface of the filtering device, blocking the holes or openings in the filtering device and thus preventing backwards flow of blood through the filtering device. The sheath or sleeve may be secured to the exterior surface of the filtering device using an appropriate adhesive or other bonding method, such as ultrasonic welding, or the sheath or sleeve may be formed as an integral part of the filtering element. Alternatively, the sheath or sleeve may be positioned on the filtering device such that the sheath or sleeve is capable of blocking all of the openings in the filtering device to prevent backwards flow of blood through the device, or the sheath or sleeve may be positioned on the filtering device in such a way as to block only a portion of the openings in the filtering device, thus allowing for a predetermined, controlled amount of backwards flow of blood into the device during aspiration of embolic material from the filtering device. In yet another embodiment, multiple sheaths or sleeves may be formed as a series of strips or flaps that are positioned on the exterior surface of the filtering device to occlude selected portions of the surface of the filtering device during aspiration of embolic material from the filtering device.

As with all of the filter elements made in accordance with the present invention, the material which can be utilized includes a variety of materials such as polymeric material which is foldable and recovers elastically to aid in the capture of the emboli trapped in the filter. Other suitable materials include braided or woven biocompatible material which can significantly filter the desired size of the embolic debris to be captured by the filter. The filter can be formed by blowing a suitable material into the proposed shape and then cutting off unwanted portions. The perfusion openings can be drilled into the material using a laser, such as an excimer laser, or by mechanically drilling and punching the openings to the desired size and shape. Laser drilling of the holes provides accuracy, quickness and the ability to drill complex hole shapes, circles, ovals and slots. Alternatively, the central filter can be made from the same or different material from the proximal cone portion and can be welded or bonded to create an integral unit.

In one particular filter made in accordance with the present invention, the proximal cone includes advantageous features which help prevent the filter from slipping off the expandable strut assembly. These features also help to prevent trapped embolic debris from being squeezed out of the filter as the filter is being collapsed for removal from the patient's vasculature. The filter may include, for example, a set of restraining straps designed to be attached to each of the proximal ends of the struts to help secure the filter onto the strut assembly. These straps can include tabs which can be wrapped around each of the struts and permanently affixed thereto utilizing a suitable adhesive. The proximal cone section of the filter may also include a number of indented flaps which cooperate to close off the inlet opening of the central filter. These indented flaps are formed on the proximal cone and move into position to cover the opening of the central filter when the proximal cone section is collapsed by the strut assembly. Therefore, the possibility that any embolic debris trapped within the deep reservoir of the central filter will be discharged through the inlet opening is greatly diminished since the opening will be closed off by these indented flaps. Likewise, the proximal cone section of the filter can also include inwardly inverting flaps located near the inlet opening of the proximal cone section which cooperate to close off the large inlet opening of the proximal cone section whenever the strut assembly is collapsed. These elements help to prevent accidental leakage of trapped embolic debris whenever the filtering assembly is collapsed for removal from the patient.

These and other advantages of the present invention will become more apparent from the following detailed description of the invention, when taken in conjunction with the accompanying exemplary drawings.

BRIEF DESCRIPTION OF THE DRAWINGS

FIG. 1 is an elevational view, partially in cross section, of an embolic protection device embodying features of the present invention showing the expandable filtering assembly in its collapsed position within a restraining sheath and disposed within a vessel.

FIG. 2 is an elevational view, partially in cross section, similar to that shown in FIG. 1, wherein the expandable filtering assembly is in its expanded position within the vessel.

FIG. 3 is a perspective view of the strut assembly which forms part of the filtering assembly of the present invention as shown in its collapsed position.

FIG. 4 is a plan view of a flattened section of the expandable strut assembly shown in FIG. 3 which illustrates one particular strut pattern for the expandable strut assembly.

FIG. 7 is an elevational view, partially in cross section, of the proximal end of the expandable strut assembly of FIG. 2 as it is rotatably attached to the guide wire.

FIG. 8 is an elevational view, partially in section and fragmented, showing the distal end of the filtering assembly of FIG. 2 as it is slidably mounted on the guide wire.

FIG. 10 is a elevational view of the various components making up the embolic protection device of FIG. 9.

FIG. 11 is an elevational view of the embolic protection device of FIG. 9 in its expanded position.

FIG. 12 is an end view of the filter element of the embolic protective device of FIG. 11 taken along lines 12—12.

FIG. 13 is an end view of the filtering element of FIG. 12 which shows the retaining tabs of the filter prior to being wrapped around the struts of the expandable strut assembly to help retain the filer element on the strut assembly.

FIG. 19 is a perspective view of an embolic protection device made in accordance with the present invention which includes inverted flaps which help close the inlet opening of the proximal cone section of the filter element when the device is collapsed.

FIG. 20 is an elevational view, partially in cross-section and fragmented, of the embolic protection device of FIG. 19 showing the proximal cone section and inverted flaps in an expanded position.

FIG. 21 is an elevational view, partially in cross-section and fragmented, of the embolic protection device of FIG. 19 wherein the proximal cone section is collapsed which causes the inverted flaps to close off the inlet opening of the proximal cone section of the filter element.

FIG. 22 is a perspective view of an alternative embodiment of a filter element made in accordance with the present invention.

FIG. 23 is an elevational view of the various components which make up another embodiment of an embolic protection device made in accordance with the present invention.

FIG. 24 is an elevational view depicting the embolic protection device of FIG. 23 in the expanded position.

FIG. 25 is an elevational view of the various components which make up another embodiment of an embolic protection device made in accordance with the present invention.

FIG. 26 is an elevated view depicting the embolic protection device of FIG. 25 in the expanded position.

FIG. 27 is an elevational view, partially in section, depicting the embolic protection device of FIG. 25 in a collapsed position and disposed within a vessel.

FIG. 28 is an elevational view, partially in section, similar to that shown in FIG. 27, wherein the embolic protection device is expanded within the vessel.

FIG. 29 is another embodiment of an embolic protection device made in accordance with the present invention.

FIG. 30 is an elevational view, partially in section, of the embolic protection device of FIG. 29 in its expanded condition within a vessel.

FIG. 31 is another embodiment of an embolic filtering device made in accordance with the present invention.

FIG. 32 is an elevational view, partially in section, of the embolic filtering device of FIG. 31 in its expanded condition and disposed within a vessel.

FIG. 33 is an elevational view of the various components making up another embodiment of an embolic protection device made in accordance with the present invention.

FIG. 34 is an elevational view depicting the embolic protection device of FIG. 33 in its expanded position.

FIG. 35 is an elevational view depicting the embolic protection device of FIG. 34 in its collapsed position.

FIG. 36 is an elevational view, partially in section, of an alternative embodiment of an embolic protection device similar to that shown in FIG. 34.

FIG. 37 is an elevational view of two deployment members which move the struts of the strut assembly into the expanded or collapsed positions.

FIG. 38 is an end view of the filtering assembly of FIG. 34 taken along lines 38—38.

FIG. 39A is an elevational view depicting an alternative strut assembly made in accordance with the present invention which allows the assembly to be collapsed to a lower profile.

FIG. 39B is an elevational view depicting an alternative strut assembly made in accordance with the present invention which allows the assembly to be collapsed to a lower profile.

FIG. 40 is an expanded side view showing the arrangement of struts on the strut assembly of FIG. 39A.

FIG. 43 is an elevational view of a proximal locking mechanism which can be utilized in accordance with embodiments of the embolic protection device made in accordance with the present invention.

FIG. 44 is an elevational view, partially in section, showing the biasing spring of the locking mechanism of FIG. 39 which can maintain the embolic protection device either in the collapsed or expanded position.

FIG. 45 is an elevational view of the various components making up another embodiment of an embolic protection device made in accordance with the present invention.

FIG. 46 is an elevational view depicting the embolic protection device of FIG. 45 in its expanded position.

FIG. 47 is an elevation view depicting the embolic protection device of FIG. 46 as it is being moved into its collapsed position.

FIG. 49 is an elevational view of another embodiment of the embolic protection device made in accordance with the present invention.

FIG. 50 is a cross-sectional view depicting the embolic protection device of FIG. 49 in its expanded position.

FIG. 51A is a cross-sectional view of another embodiment of an embolic protection device made in accordance with the present invention incorporating a flexible flap to provide for controlled backwards flow of blood through the device during aspiration of embolic material trapped in the device.

FIG. 51B is an enlarged view of a portion of the device of FIG. 51A showing the position of the flexible flap during normal usage of the embolic protection device.

FIG. 52A is a cross-sectional view of the device of FIG. 51A showing placement of an aspiration catheter to remove embolic material trapped in the device.

FIG. 52B is an enlarged view of a portion of the device of FIG. 52A showing the position of the flexible flap during aspiration of embolic material trapped in the embolic protection device.

FIG. 57 is a cross-section view of another embodiment of an embolic protection device made in accordance with the present invention incorporating a plurality of sheaths (sleeves) to provide for controlled backwards flow of blood through the device during aspiration of embolic material trapped in the device, showing the sheaths in an open position.

FIG. 58 is a cross-sectional view of the device of FIG. 57 showing the sheaths in a closed position during aspiration of embolic material trapped within the embolic protection device.

DETAILED DESCRIPTION OF THE PREFERRED EMBODIMENTS

Figure 5:
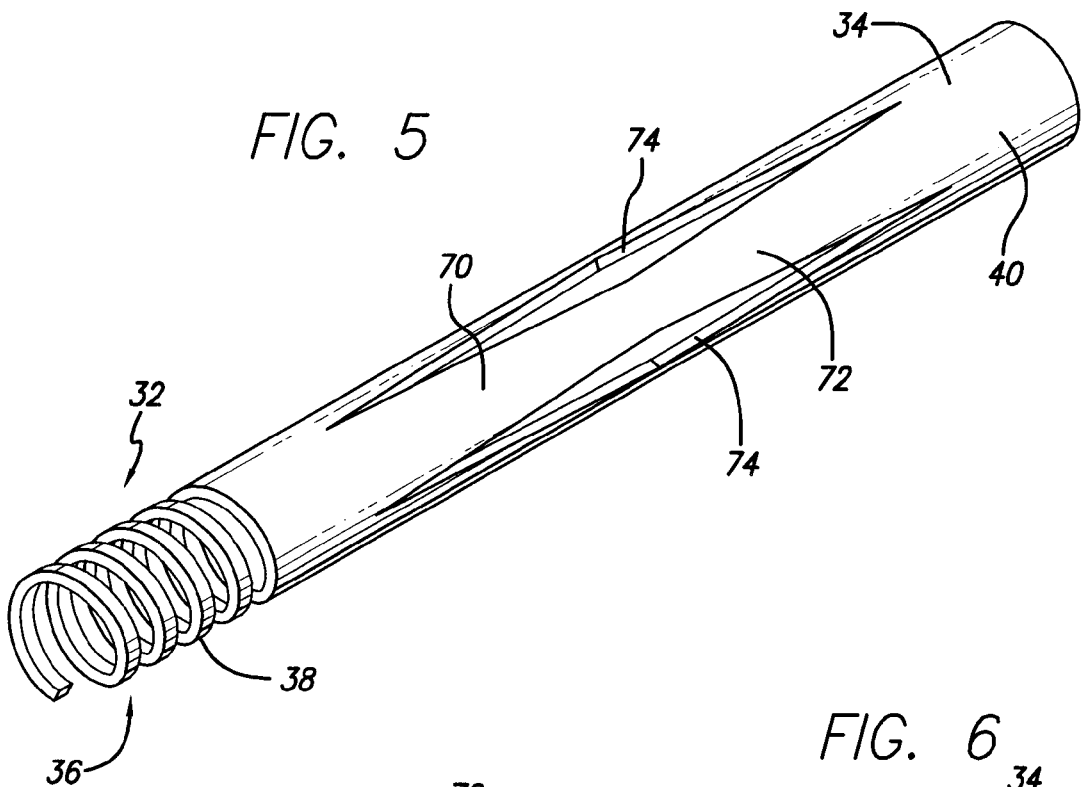
FIG. 5 is a perspective view of another embodiment of an expandable strut assembly which forms part of the filtering assembly of the present invention in its collapsed position.

Turning now to the drawings, in which like reference numerals represent like or corresponding elements in the drawings, FIGS. 1 and 2 illustrate an embolic protection device 10 incorporating features of the present invention. In the particular embodiment shown in FIGS. 1 and 2, the embolic protection device 10 comprises a filter assembly 12 which includes an expandable strut assembly 14 and a filter element 16. The filter assembly 12 is rotatably mounted on the distal end of an elongated tubular shaft, such as a guide wire 18. Additional details regarding particular structure and shape of the various elements making up the filter assembly 12 are provided below.

The embolic protection device 10 is shown as it is placed within an artery 20 or other blood vessel of the patient. This portion of the artery 20 has an area of treatment 22 in which atherosclerotic plaque 24 has built up against the inside wall 26 of the artery 20. The filter assembly 12 is placed distal to, and downstream from, the area of treatment 22 as is shown in FIGS. 1 and 2. Although not shown, a balloon angioplasty catheter can be introduced within the patient's vasculature in a conventional SELDINGER technique through a guiding catheter (not shown). The guide wire 18 is disposed through the area of treatment and the dilatation catheter can be advanced over the guide wire 18 within the artery 20 until the balloon portion is directly in the area of treatment. The balloon of the dilatation catheter can be expanded, expanding the plaque 24 against the inside wall 26 of the artery 20 to expand the artery and reduce the blockage in the vessel at the position of the plaque 24. After the dilatation catheter is removed from the patient's vasculature, a stent 25 (shown in FIG. 2) could also be delivered to the area of treatment 22 using over-the-wire techniques to help hold and maintain this portion of the artery 20 and help prevent restenosis from occurring in the area of treatment. Any embolic debris 27 which is created during the interventional procedure will be released into the bloodstream and will enter the filtering assembly 12 located downstream from the area of treatment 22. Once the procedure is completed, the filtering assembly 12 is collapsed and removed from the patient's vasculature, taking with it all embolic debris trapped within the filter element 16.

One particular form of the expandable strut assembly 14 is shown in FIGS. 1–4. As can be seen in these figures, the expandable strut assembly 14 includes a plurality of radially expandable struts 28 which can move from a compressed or collapsed position as shown in FIG. 1 to an expanded or deployed position shown in FIG. 2. FIG. 3 shows a length of tubing 30 which can be utilized to form this expandable strut assembly 14.

The expandable strut assembly 14 includes a proximal end 32 which is rotatably attached to the guide wire 18 and a distal end 34 which is free to slide longitudinally along the guide wire 18 and also can rotate thereabout. The distal end 34 moves longitudinally along the guide wire whenever the struts move between the expanded and contrasted positions. The proximal end 32 includes a short tubular segment or sleeve 36 which has a coil spring formed therein which acts as a dampening member or element 38. The function of this dampening element 38 will be explained below. The distal end 34 of the tubing 30 also includes a short segment or sleeve 40 which is slidably and rotatably disposed on the guide wire 18.

Referring now to FIGS. 1, 2 and 7, the proximal end 32 of the expandable strut assembly 14 is mounted between a tapered fitting 42 located proximal to the dampening element 38 and a radiopaque marker band 44 located distal to the proximal end 32. The tapered end fitting 42 and marker band 44 fix the proximal end 32 onto the guide wire 18 to prevent any longitudinal motion of the proximal end along the guide wire but allow for rotation of the proximal end 32 and the filtering assembly 12. This particular construction allows the expandable strut assembly to rotate or "spin" freely about the guide wire. In this manner, the filtering assembly 12 will remain stationary should the guide wire 18 be rotated at its proximal end after the embolic detection device 10 has been deployed within the patient's vasculature. This is just one way of affixing the expandable strut assembly 14 onto the guide wire 18 to allow it to spin or rotate on the guide wire 18. Other ways of performing this same function can be employed with the present invention.

The benefits of mounting the proximal end 32 of the expandable strut assembly 14 to the guide wire 18 include the ability to precisely deploy the filtering assembly 12 within the artery once the guide wire 18 has been positioned in the patient's vasculature. Since the proximal end 32 cannot move longitudinally along the guide wire, the physician can be sure that the filtering element 12 will be placed exactly where he/she places it once the restraining sheath 46 is retracted to allow the expandable struts to move into their expanded position. Additionally, since the proximal end 32 is affixed to the guide wire, any movement of the filtering element as the restraining sheath 46 is retracted should not occur. Since the expandable struts 28 can be made from self-expanding materials, there may be some stored energy in the filtering assembly 12 as it is held in its collapsed position by the restraining sheath 46. As that restraining sheath 46 is retracted, there can be a frictional build-up which can cause the strut assembly 14 to move outward if the proximal end 32 were not affixed to the guide wire 18. As a result, if the ends of the strut assembly 14 were not somehow fixed onto the guide wire, there could be a tendency of the filtering element 12 to spring out of the restraining sheath 46 as it is being retracted. As a result, the placement of the filtering element 12 will not be as accurate since the physician will not be able to pre-determine if and how much the filtering assembly 12 would move as the restraining sheath 46 is retracted.

The dampening element 38, which in this particular embodiment of the invention is shown as a helical coil formed on the proximal end 32 of the strut assembly 14, helps to dampen any shockwaves (vibratory motion) which may be transmitted along the guide wire 18, for example, when interventional devices are being delivered or exchanged over the guide wire in an over-the-wire fashion. Similarly, this dampening element 38 also helps dampen any shock forces which may result as the restraining sheath 46 is retracted to allow the radial expandable struts to move into their expanded position as shown in FIG. 2. The helical coil can also act as an attachment method which helps retain guide wire flexibility. The dampening element 38 should somewhat also dampen shock which may be created as the recovery sheath 48 (FIG. 2) contacts the struts to collapse the filter assembly 12 when the embolic protection device is to be removed from the patient's vasculature. As a result, this dampening element 38 will absorb and dissipate forces which would otherwise act on the expanded filtering assembly 12 and could cause the assembly 12 to scrape the inside wall 26 of the artery 20 or otherwise cause trauma to the vessel. This dampening element 38 also helps prevent displacement or misalignment of the filter element within the artery which may result from a sudden shock transmitted along the guide wire 18.

The filter element 16 utilized in conjunction with this preferred embodiment of the invention includes a tapered or cone shaped section 50 which has a plurality of openings 52 which allow the blood to flow through the filter 16 but captures emboli within the inside of the cone shaped section. The filter element 16 includes a short proximal section 52 which is integral with the cone shaped section 50 and expands to a substantially cylindrical shape when the struts 28 of the strut assembly 14 are deployed. The inlet opening 51 allows any embolic debris 27 to enter the filter element 16 for capture. This short cylindrical section 52 also serves as a suitable location where the filter element 16 can be adhesively or otherwise affixed to each strut 28 of the strut assembly 14. The filter element 18 includes a short distal cylindrical section 54 which is integral with the remaining sections of the filter and is attached to the sleeve segment 40 which forms the distal end 34 of the expandable strut assembly 14. This distal cylindrical section 54 can be attached to the sleeve 40 using adhesives or other bonding techniques.

Referring again to FIG. 1, the filter assembly 12 is maintained in its collapsed or compressed position through the use of a restraining sheath 46 which contacts the struts 28 and filter elements 16 to maintain the filtering assembly 12 collapsed. Although not shown, the guide wire and restraining sheath 46 have proximal ends which extend outside the patient. The struts 28 can be manipulated into the expanded position by retracting the restraining sheath 46 (via its proximal end) to expose the struts 28. Since the struts 28 are self expanding, the removal of the restraining sheath 46 allows the struts 28 and filter element 16 to move to the expanded position within the artery 20.

The guide wire 18 includes a small sphere 56 affixed thereto which is beneficial during the delivery of the embolic protection device 10 into the patient's vasculature. This sphere 56 is approximately as large as the inner diameter of the restraining sheath 46 and is utilized as a "nosecone" to prevent possible "snow plowing" of the embolic protection device as it is being delivered through the patient's arteries. The sphere 56 is atraumatic and has a smooth surface to help the embolic protection device travel through the patient's vasculature and cross lesions without causing the distal end of the restraining sheath 46 to "dig" or "snow plow" into the wall of the arteries. When the embolic protection device 10 is to be removed from the patient's vasculature, a recovery catheter 48 is utilized to collapse and recover the filter assembly 12. (FIG. 2). Generally, this recovery sheath 48 has a slightly larger inner diameter than the restraining sheath 46 since the struts 28 are now deployed and may require some increased hoop strength at the distal end 47 of the recovery sheath 48 to properly move the strut assembly 14 back into its collapsed position. The collapse of the expandable strut assembly 14 can be accomplished by holding the guide wire 18 and moving the proximal end (not shown) of the recovery sheath 48 forward which will move the distal end 47 of the sheath 48 over the struts 28. Alternatively, the recovery sheath 48 can be held stationary while the proximal end of the guide wire is retracted back to pull the entire filter assembly 12 into the sheath 48. Upon collapse of the filter assembly 12, any embolic debris generated and entering the bloodstream during the interventional procedure will remain trapped inside the filter element 16 and will be withdrawn from the bloodstream when the embolic protection device 10 is removed from the patient's vasculature.

A radiopaque marker 58 located approximately at the longitudinal center of the expandable strut assembly 14 is also affixed to the guide wire 18 to provide the physician with a reference marker when positioning the device within the patient's artery 20.

The number of struts 28 formed on the expandable strut assembly 14 can be any number which will provide sufficient expandability within the artery to properly deploy and maintain the filter element 16 in place. In the embodiment shown in FIGS. 1 and 2, the expandable strut assembly has four self-expanding struts 28. Likewise, the particular size and shape of each strut 28 can be varied without departing from the spirit and scope of the present invention. In this preferred embodiment, the strut pattern includes a first portion 60 having an inverted triangular shape, a substantially straight center section 62, and a second inverted triangular shaped section 64 which completes the strut. This particular strut pattern is preferred since the design provides greater strength in regions of the strut where there would be a tendency for the strut to break or become weakened. These regions include the very proximal and distal ends of each strut which are designed with a wider base. This particular design also allows the composite strut assembly to open and close more uniformly which is beneficial especially when collapsing the struts for removal from the patient. Additionally, the center section 62 allows the struts 28 to expand to a greater volume, which allows a larger filter element to be placed on the strut assembly 14, if needed.

Referring now specifically to FIG. 4, a plan view of a rolled out flat sheet of the tubing 30 utilized to form the struts 28 is shown. As can be seen from FIG. 5, a particular design pattern is cut into wall of the tubing 30 in order to form each strut 28. In the case of the embodiment shown in FIG. 3, that pattern consists of a truncated diamond shape 65 which helps form the first section 60, the center section 62 and the second section 64. By selectively removing portions of the tubing 30 through laser cutting or other suitable means, each particular strut 28 can be made to a precise shape, width and length. This truncated diamond pattern 68 repeats as can be seen in FIG. 4 to provide uniform size to each of the struts 28 formed therein.

Figure 6:
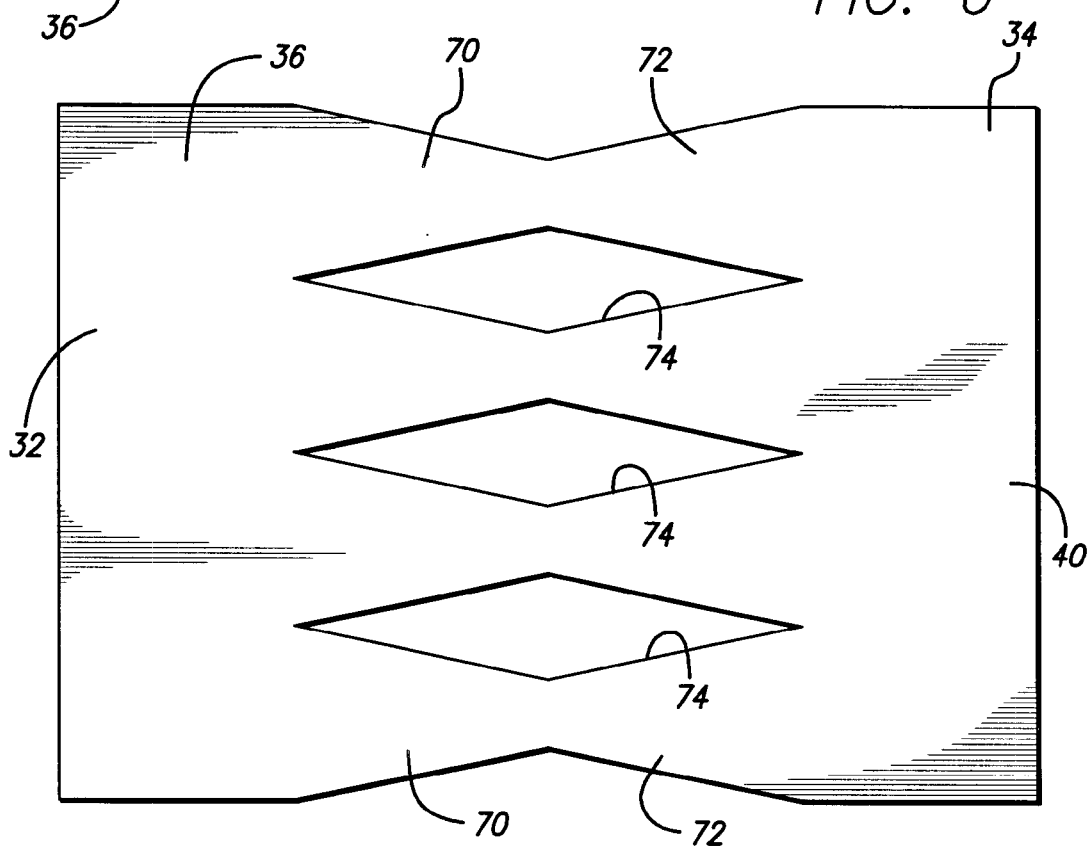
FIG. 6 is a plan view of a flattened section of the expandable strut assembly of FIG. 5 which shows an alternative strut pattern for the expandable strut assembly.

An alternative preferred embodiment of the expandable strut assembly 14 is shown in FIGS. 5 and 6. This particular strut assembly 14 is similar to the one shown in FIGS. 3 and 4 except that there is no center section. The struts 68 shown in FIGS. 5 and 6 consist of a pair of inverted triangles which form a first section 70 and a second section 72. The plan view of the flat sheet of the tubing 30 used to form the strut assembly 14, as shown in FIG. 6, shows a repeating diamond pattern 74 which is cut into the tubing to create each individual strut 28. Again, this particular pattern is preferred since greater strength is provided near the proximal and distal ends of each strut where there would be a tendency for breakage or a weakness of the strut. When the particular pattern is cut into the tubing, whether it be the pattern shown in FIGS. 3–4 or 5–6 or some other pattern the sleeve 36 which forms the proximal end 32 of the strut assembly 14 can thereafter be similarly cut to create the helical coil which forms the damping element 38 on the strut assembly 14.

Figure 9:
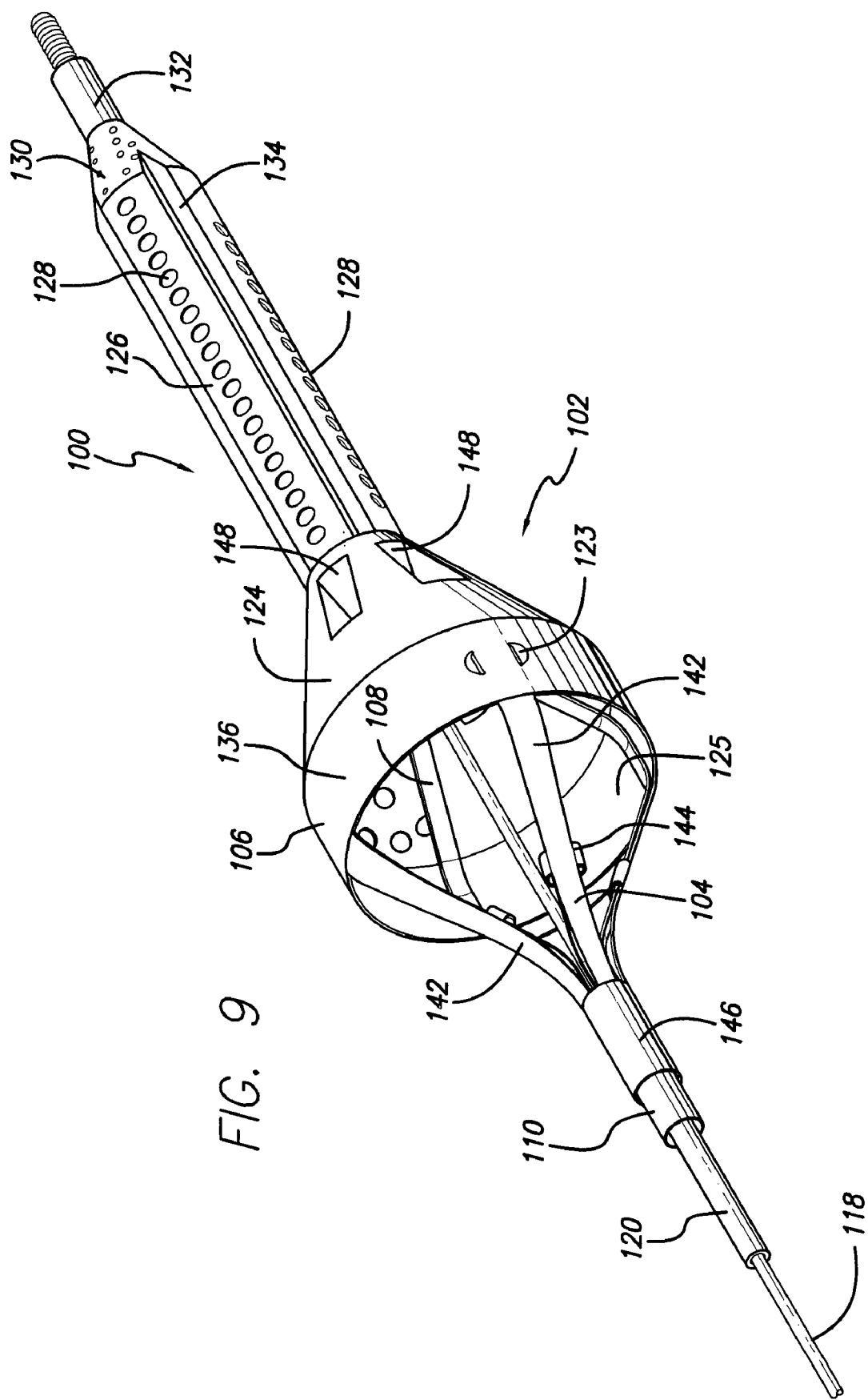
FIG. 9 is a perspective view of another embodiment of an embolic protection device made in accordance with the present invention.

Another embodiment of the present invention is shown in FIGS. 9–11. As can be seen in FIG. 9, the embolic protection device 100 includes a filter assembly 102 having an expandable strut assembly 104 and a unique filter element 106. The particular strut assembly 104 utilized with this embolic protection device 100 is similar to the structure of the expandable strut assembly 14 shown in the previous embodiment. The filter element 106, which will be described in greater detail below, is utilized in its expanded position to collect any embolic debris for removal from the blood stream of the patient.

The various elements making up this particular embodiment of the embolic protection device 100 are shown in FIG. 10. In this particular embodiment, the strut assembly 104 does not necessarily have to be made from a self-expanding material, as the strut assembly 14 disclosed in the previous embodiment. Rather, it could be made from stainless steel or other materials which require the application of external axial force on the proximal end 110 and distal end 112 of the strut assembly 104 to move the struts 108 between the contracted and expanded positions. As is shown in FIGS. 10 and 11, the proximal end 110 of the assembly 104 includes a short tubular or sleeve-like segment 114 and a similar distal segment 116. The struts 108 are moved from a contracted to a deployed position by imparting an inward axial force on the proximal end 110 and distal end 112 of the strut assembly 104. This can be accomplished by first attaching the distal end 112 of the assembly 104 directly to the guide wire 118. The proximal end 110 of the strut assembly 104, can then, in turn, be attached to an outer tubular member 120 which, along with the guide wire 118, has a proximal end which extends outside of the patient. The proximal ends (not shown) of both the outer tubular member 120 and the guide wire 118 can be manipulated by the physician to either impart an inward axial force on the two ends 110 and 112 of the strut assembly 104 to move the struts 108 to the deploy position or can be moved to impart an outward axial force on both ends 110 and 112 to collapse the struts 108 back to their collapsed position.

The struts 108 of the strut assembly 104 can be made from a piece of tubing (hypotube) in which select portions of the tubing are removed to form the particular size and shape of each strut. The strut assembly 104 could also be made from a self-expanding material such as nickel-titanium (NiTi) if desired. The struts 108 would then be biased into either the collapsed or expanded position with the outer tubular member 120 being used to move the proximal end 110 in order to expand or contract the strut assembly 104, depending upon, of course, the manner in which the expandable struts 108 are biased. Again, in the embodiment shown in FIG. 10, the struts 108 have a similar shape as the struts 28 shown in the embodiment of FIGS. 1–4. This particular embodiment of an embolic protection device thus eliminates the need to utilize both a restraining sheath and recovery sheath which would be otherwise needed in order to deploy and contract the embolic protection device. This particular design, however, does not allow for the filter assembly 102 to rotate as freely along the guide wire 118 as does the previous embodiments, although there can be some rotation. However, the outer tubular member 120 and guide wire 118 are utilized in a similar fashion by allowing interventional devices to be delivered over the outer tubular member in an over-the-wire fashion after the embolic protection device 110 is in place within the patient's vasculature.

It should be appreciated that the strut assembly 104 could also be made from a self-expanding material which maintains the struts 108 biased in their expanded position. The outer tubular member 120 would still be utilized in order to move the expanded struts 108 back into their collapsed position. The proximal ends of the outer tubular member 120 and guide wire 118 can be attached to a simple locking mechanism 600 (shown in FIGS. 39 and 40) which can be utilized to move the outer tubular member relative to the guide wire for maintaining the strut assembly 104 in its collapsed position until ready to be deployed within the patient's vasculature. It should further be appreciated that the particular embolic protection device 100 can also be modified to eliminate the outer tubular member 120 and be a self-expanding assembly like the one shown in FIGS. 1–2. In such a case, the proximal end 110 of the strut assembly 104 can be rotatably attached to the guide wire 118 with the distal end 112 being slidably mounted on the guide wire to allow for longitudinal motion and rotational motion about the guide wire 118.

The filter element 106 utilized in conjunction with this particular embodiment, or which can be utilized with any of the other embodiments disclosed herein, has a unique shape to provide a large reservoir to collect and maintain any embolic debris which may be trapped within the filter 106.

Referring now to FIGS. 9–12, the various sections of the filter element 106 will be described in greater detail. It should be noted that the filter element 122 of FIG. 22 incorporates many of the same filter sections as the filter element 106 shown in FIGS. 10–12. Therefore, corresponding sections of these filters will be described simultaneously in order to better understand the principles underlying these unique filter elements. Both filter elements include a proximal cone section 124 which expands to fit within the diameter of the artery. This particular proximal cone section 124 blocks or funnels blood flow and embolic debris into the main or central filter 126. In both of the filter elements shown in FIGS. 9 and 22, the proximal cone section 124 includes a plurality of openings 128 which are utilized in filtering the embolic debris. However, it is possible to eliminate the openings 128 on the proximal cone section 124 to allow it to primarily direct blood flow and embolic debris directly into the central filter 126. This central filter 126 is integral with the proximal cone section 124 and includes a number of openings 128 utilized to permit blood flow through this section of the filter but to retain any embolic debris which is larger than the size of the openings 128. The openings 128 can be laser cut or otherwise punched into this central filter 126. This central filter 126 has a substantially cylindrical shape and acts as a large reservoir for holding the embolic debris. Ideally, it is sized such that when it is completely full of embolic material, it does not collapse to a smaller profile. However, it should be able to be withdrawn into the guiding catheter (not shown) when in its fully expanded condition with embolic debris trapped therein. Thus, the maximum outer expanded diameter of this central filter 126 should be smaller than the inner diameter of the guiding or sheath utilized in deploying the embolic protection device 100 in the patient's vasculature. The central filter can be made from a stiffer polymeric material which will maintain the shape and outer diameter to prevent the filter from collapsing after use. The resulting stiffer central filter cannot be squeezed during the collapse and removal of the filtering assembly from the artery which should prevent any trapped embolic debris from being squeezed out of the reservoir portion of the central filter.

Both filters 106 and 122 include a distal tapered region 130 which tapers down to the shaft of the guide wire 118. The taper of this particular region of the filter elements 106 and 122 facilitates the delivery of the embolic protection device 100 and helps prevent the "snow plow" effect when being delivered through the patient's vasculature. There is a small distal section 132 which also forms a part of the filter element and is utilized to attach the distal end of the filter directly onto the guide wire. This distal section 132 can be fastened utilizing well-known adhesives or other bonding techniques to permanently affix it to the guide wire 118 and prevent any embolic debris from escaping through the distal opening of this distal section 132.

Figure 16:
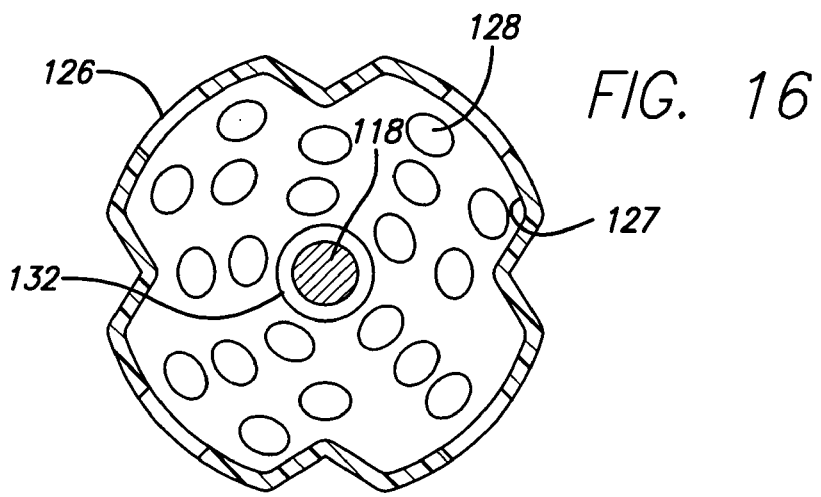
FIG. 16 is a cross sectional view of the central filter of the filtering device of FIG. 11 taken along lines 16—16.

The primary benefit of utilizing a large central filter with a proximal cone section is that there is a large filtering area provided by the central filter 126 which is less likely to squeeze out trapped embolic debris when the embolic protection device 100 is being removed from the patient's vasculature. As can be seen in FIG. 22, the central filter 126 has a general cylindrical shape while the central filter 126 of FIG. 9 can be a generally cylindrically shaped but can also include side creases 134 which produce a unique-looking design. The particular cross-sectional view of the central filter 126 of filter element 106 is shown in FIG. 16 and shows just one of a number of different shapes that can be used to create the central filter 126. In use, the filter element 122 of FIG. 22 would be attached to the strut assembly 104 and guide wire 118 utilizing adhesives or other bonding techniques.

The filter element 106 of FIG. 9 also incorporates some unique features which are not shown in the more basic filter design shown in FIG. 22. These advantages include the unique cross-sectional shape of the central filter 126 shown in FIG. 16, along with other features which help maintain the filter element 106 securely attached to the struts 108 of the strut assembly 104. Referring again to FIGS. 10–12, the filter element 106 includes a short outer rim 136 which is proximal to the end of the cone section 124 and has a large inlet opening 125 for receiving the blood flow and any embolic debris released into the bloodstream. This proximal outer rim 136 is ring-shaped and can be utilized to help attach the filter onto the struts 108 of the assembly 104. As can be seen in FIG. 10, this proximal outer ring is attached to the middle section 138 of each strut 108 and includes a tab 123 which can be wrapped around and attached to the strut 108. This proximal outer ring 136 also helps maintain the circular inlet opening 125 which must be expanded and maintained within the artery of the patient. Attached to the front of the outer rim 136 are restraining straps 142 which are likewise utilized to help hold the filter onto the struts 108 of the assembly 104. Each restraining strap 142 includes tab-like projections 144 which can wrap around each individual strut and be affixed thereto utilizing a bonding agent such as adhesive. These elements allow the restraining straps 142 to hold the filter element 106 onto the strut assembly 104. It should be appreciated that any number of different tab-like projections 144 can be utilized in conjunction with these restraining straps 142 to help secure the filter onto the assembly 104. The proximal end of each restraining strap 144 is attached to a sleeve 146 which also can be adhesively fixed to the tubular segment 114 formed at the proximal end 110 of the strut assembly 104. These various sections of the filter 106 can be made as one composite unit and can be formed by cutting a pattern into a pre-formed filter blank. Thereafter, the openings 128 along the length of the filter element 106 can be placed accordingly.

Figure 17:
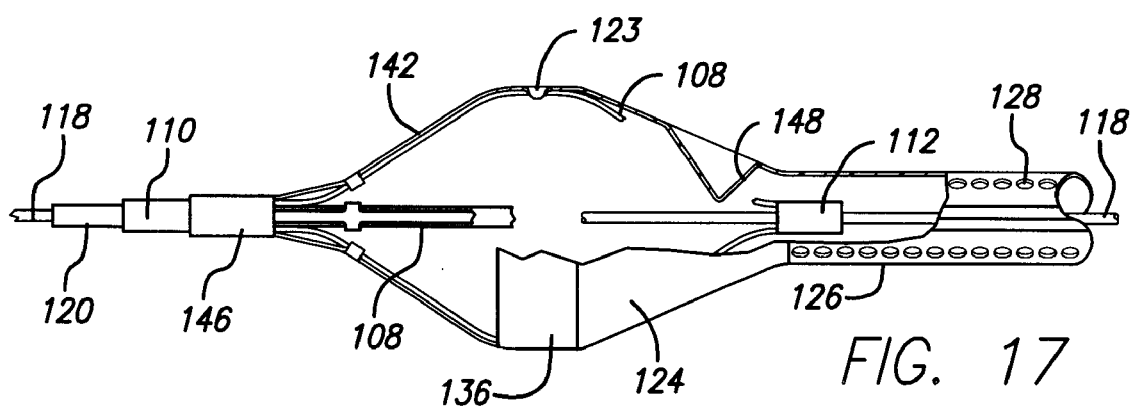
FIG. 17 is an elevational view, partially in cross-section and fragmented, of the embolic protection device of FIG. 11 showing the indented flaps of the proximal cone section in the expanded position.
Figure 18:
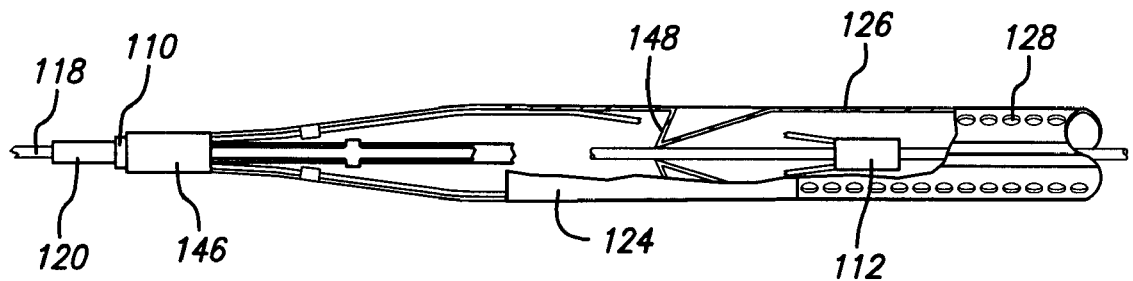
FIG. 18 is an elevational view, partially in cross-section and fragmented, showing the indented flaps of the proximal cone section in the collapsed position which causes the indented flaps to close the inlet opening of the central filter of the device.

The proximal cone section 126 of the filter element 106 shown in FIG. 9 includes a plurality of indented flaps 148 which are utilized to help close the opening of the central filter 126 when the proximal cone 124 is in its collapsed position. Each of these indented flaps 148, as shown in FIGS. 11, 17 and 18, are created such that as the proximal cone section 124 is being closed, the flaps join together and cooperate to form a barrier which prevents embolic debris from being released through the inlet opening 127 of the central filter 126. In the particular embodiment shown in FIG. 9, four such indented flaps can be utilized (only two of which are shown in FIGS. 11, 17 and 18) in order to create the barrier necessary to close the opening to the central filter 126. However, the number of indented flaps 148 and the size and shape of each flap 148 can be varied accordingly in order to create a protective barrier which helps prevent trapped embolic debris from escaping from the central filter 126 as the device 100 is being collapsed for removal from the patient.

Referring now to the FIGS. 19, 20 and 21, a variation of the indented flaps 148 is shown in the proximal cone section 124 of the filter element 106. As can be seen in these figures, there are a pair of flap portions 150 which are located within the proximal cone section 124 and are utilized as a mechanism for closing the inlet opening 127 of the filter element 106 when the filter assembly is collapsed. These flap portions 150 act much like the indented flaps 148 in that as the proximal cone section 124 is being collapsed, these flap portions 150 extend across the inlet opening 127 of the filter element 106 to create a barrier which helps prevent trapped embolic debris from being released back into the bloodstream. These flap portions 150 can be small appropriately shaped pieces which extend across the inlet opening when the filter is expanded but do not interfere with the flow of blood going into the filter element 106. Blood simply travels around the flap portions 150, along with any embolic debris, to the center filter 126 where the embolic debris will be trapped in the debris reservoir. This feature provides a preventive measure to diminish the possible release of trapped embolic debris when the embolic protection device 100 is being collapsed and removed from the patient's vasculature.

Figure 15:
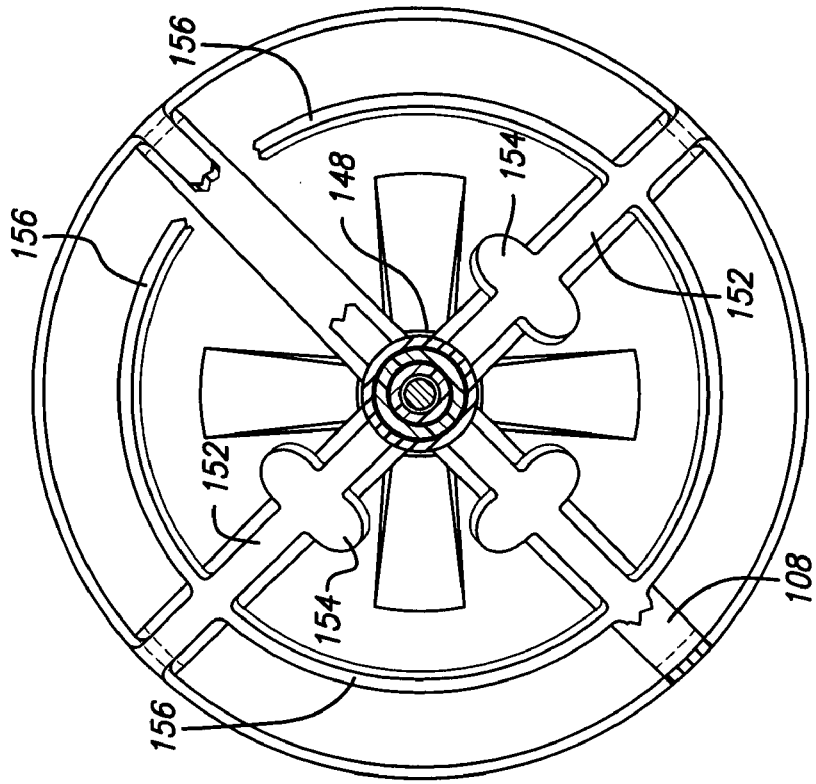
FIG. 15 is an end view of the filter element of FIG. 14, showing the retaining tabs of the filter element prior to being wrapped around the struts of the expandable strut assembly to help retain the filter element on the strut assembly.
Figure 14:
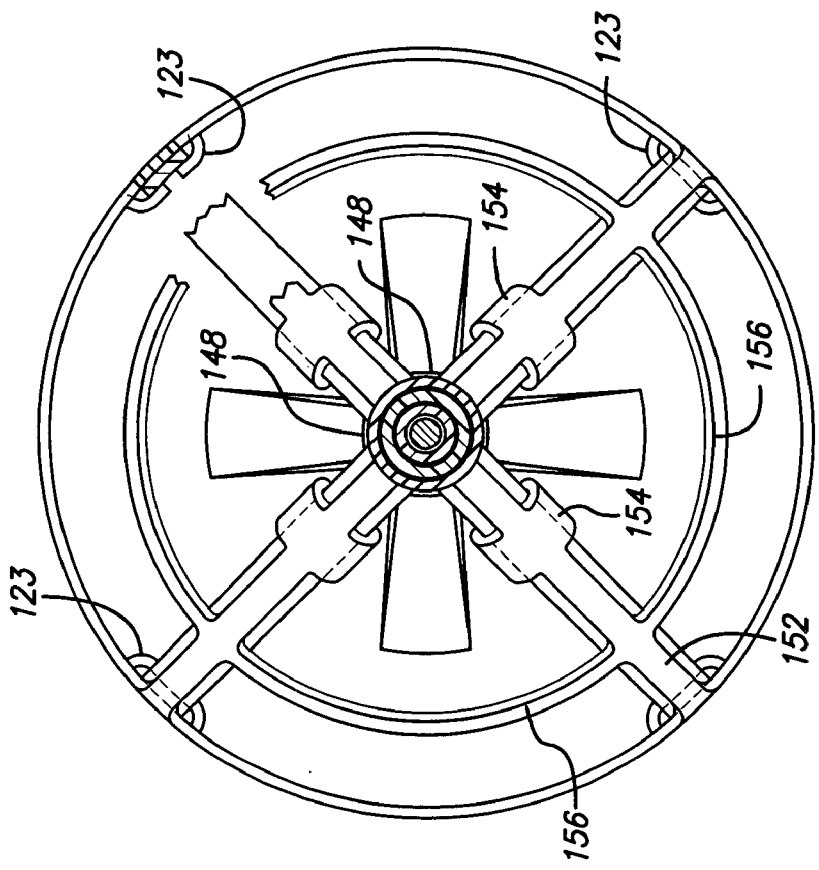
FIG. 14 is an end view, similar to that shown in FIG. 12, of another embodiment of the filter element of the embolic protection device which shows an alternative embodiment of retaining tabs and structural elements that can be used to help retain the filter element on the strut assembly.

Referring now to FIGS. 14 and 15, an alternative form of the restraining straps and tabs which are utilized to affix the filter element 106 is shown. In these particular figures, the restraining strap 152 extends along each strut 108 and a tab like projection 154 is utilized to affix the restraining strap to each individual strut 108. Additional lateral strapping members 156 which extend laterally from each restraining strap 152 can also be utilized to help prevent the filter element 106 from moving off the strut assembly 104 during usage. These various designs shows alternative ways of affixing the filter element 106 onto the strut assembly 104. It should be appreciated that still other forms of attaching the filter element 106 to the strut assembly 104 can be utilized without departing from the spirit and scope of the present invention.

Another embodiment of the present invention is shown in FIGS. 23 and 24. In this particular embodiment, the embolic protection device 200 includes a filter assembly 202 having a strut assembly 204 and a filter element 206. The strut assembly 204 is similar to the strut assembly shown in FIGS. 1–4. It includes self-expanding struts 208 which are expandable from a collapsed position to a fully expanded position. This strut assembly 204 includes a proximal end 210 and a distal end 212. This strut assembly 204 can be made from a piece of tubing in which the struts are created by selectively removing portions of the tubing. In this particular embodiment, the tubing can be hypotubing made from a shape memory material such as nickel-titanium (NiTi). The resulting strut assembly 204 is normally biased to remain in the expanded position and require the applications of force on the ends 210 and 212 to deploy the struts 208 back to their collapsed position.

The proximal end 210 includes a segment of tubing 214 and the distal end 212 includes a similar segment of tubing 216 as well. The distal end 212 is permanently attached to the guide wire 218 near the distal coil 220 of the guide wire. The distal end 212 can be bonded using adhesives or welded, brazed or soldered to the guide wire 218. Likewise, the proximal end 210 of the strut assembly 204 can be bonded, welded, brazed or soldered to an elongated outer tubular member 222 which has a proximal end which extends outside of the patient. The proximal ends of the elongated tubular member 222 and the guide wire 218 can be manipulated by the physician to either open or close the filter assembly 202. A suitable locking mechanism 600 for maintaining the strut assembly 204 in its collapsed or closed position is disclosed in FIGS. 43 and 44 and is described in greater detail below.

The filter element 206 comprises of a cone shape portion 224 which is attached to the center section 226 of each strut 208. A plurality of openings 228 are laser cut or otherwise formed in the filter 206 which allows blood to flow through the filter but captures embolic debris which is larger than the size of the openings. This is another more example of a variation of the embolic protection device which can be made in accordance with the present invention.

Another embodiment of the present invention is shown as a embolic protection device 300 in FIGS. 25–28. Like the other embodiments, this device 300 includes a filtering assembly 302 which has an expandable strut assembly 304 and a filter element 306 attached to the strut assembly 304. Individual struts 308 are formed on the strut assembly 304 for moving the filtering element 306 into an expanded position within the patient's vasculature. The strut assembly 304 is some what similar similar to the previous embodiments disclosed above in that an outer elongated tubular member 310 is utilized in conjunction with a guide wire 312 to collapse and deploy the strut assembly 304. Although not shown in FIGS. 25 and 26, the outer tubular member 310 has a proximal end which extends with the proximal end of the guide wire outside of the patient to allow the physician to move the proximal ends to deploy or collapse the filtering assembly 302. The strut assembly 304 can be formed by selectively removing material from the outer tubular member 310 near its distal end to create the individual struts 308. The struts will open upon application of an inward force on ends of the individual struts 308. Alternatively, the strut assembly 304 can be made from a piece of hypotubing which can be affixed to the outer tubular member 310 as is shown in some of the previous embodiments of the invention. The entire outer tubular member 310 with the strut assembly 304 is free to slide along the length of the guide wire 312 which allows the filtering assembly 302 to be positioned within the patient's vasculature in an over-the-wire fashion.

As can be seen in FIGS. 25–28, a stop element 320 is located near the distal coil 322 of the guide wire 312. This distal stop element 320 is utilized in conjunction with the outer tubular member 310 to produce the force necessary to expand the struts 308 into the expanded position. The embolic protection device 300 can be utilized in the following matter. First, the physician maneuvers the guide wire 312 into position past the lesion or area of treatment. Thereafter, the outer tubular member 310 with the strut assembly 304 is advanced over the guide wire 312 in an over-the-wire technique. The embolic protection device 300 remains in its collapsed position while being delivered over the guide wire 312 to the distal end 313 of the guide wire, as is shown in FIG. 27. Thereafter, the physician allows the distal sleeve 312 of the outer tubular member 310 to contact the stop element 320 located on the guide wire 312. By applying additional force at the proximal end of the elongated tubular member 310, the physician will cause the struts 308 to expand radially outward for deployment within the artery. The resulting expansion of the struts 308 thereby opens up the filter element 306 within the artery. The physician can then deliver interventional debris into the area of treatment and perform the procedure on the lesion. Any embolic debris which may be created during the interventional procedure will be collected within the interior of the filter 306.

A simple locking mechanism 600 device located at the proximal end of the outer tubular member and guide wire, as is shown in FIGS. 43 and 44, can be utilized to move and maintain the strut assembly 304 in the expanded condition. Thereafter, once the embolic protection device 300 is desired to be removed from the vasculature, the physician merely retracts the proximal end of the outer tubular member 310 to remove the force on the strut assembly 304 allowing the struts 308 to move back to the collapsed position. Thereafter, the embolic protection device 300 and guide wire 312 can be removed from the patient's vasculature.

The filter element 306 takes on a some what different shape from the previous filter element in that the main portion of the filter element 306 has a shape of a half of a dilatation balloon utilized in angioplasty procedures. Perfusion openings 315 are located on the filter elements 306 for allowing blood perfusion while capturing embolic debris. The proximal end of the filter element 306 includes a plurality of restraining straps 314 which extend to a proximal sleeve 316 which is affixed to the outer tubular member 310 proximal of the struts 308. The distal end 318 of the filter element 306 is also attached to the distal sleeve 321 which is formed on the outer tubular member 310 when the struts 308 are formed.

FIGS. 29 and 30 show another embodiment of a embolic protection device 400 made in accordance with the present invention. This particular embodiment is somewhat similar to the previous embodiments in that an external force is generated on the ends of the struts of the strut assembly to facilitate the outward expansion and inward contraction of the struts. Referring specifically now to FIG. 29, the embolic protection device 400 includes a filter assembly 402 having a strut assembly 404 which has a filter element 406 attached thereto. The individual struts 408 are formed on an outer tubular member 410 which has a distal end 412 attached to the distal end 413 of an inner tubular member 414. Both the inner member 414 and the outer member 410 have proximal ends which are located outside of the patient's vasculature. The struts 408 are radially expanded by moving the outer tubular member 410 relative to the inner tubular member 414 to apply the necessary axial force to cause the struts to deploy outward. An opposite axial force is necessary to cause the struts 408 to move back to the collapsed position when the device is to be removed from the patient's vasculature. In this embodiment, more than four struts 408 are used to expand the filter element 406 within the artery 420. Again, the number, size and shape of the struts 408 can be varied without departing from the spirit and scope of the present invention.

The filter element 406 also has the shape of one half of a dilatation balloon utilized in angioplasty procedures and includes openings 416 which allows blood to flow through the filter but captures the desired size of the embolic debris. The proximal end of the filter element 406 which includes an inlet opening 417 is attached to each of the center sections 418 of the struts 408. The distal end 420 of the filter 406 is attached to the distal end 412 of the strut assembly 404.

The lumen 422 of the inner tubular member 414 can be utilized for a number of purposes, such as blood perfusion past the deployed filter assembly 402 when placed in the artery. Therefore, should the openings 416 of the filter element 406 become clogged with debris which prevents blood from flowing through the filter, oxygenated blood can be perfused to downstream vessels via the inner lumen of the inner tubular member 414. This lumen can also be utilized for delivering the embolic protection device 404 over a guide wire in an over-the-wire fashion.

FIGS. 31 and 32 show a variation of the previous filter element which can be utilized in conjunction with the present invention. The filter embolic protection device 400 is basically the same device shown in FIGS. 29 and 30 except that the filter element 430 has a different design. As can be seen in FIG. 31, the filter element 430 includes a proximal cone shape portion 431 which extends in front of the inlet opening 432 of the filter element 430. This type of filter 430 has advantages in that it may be easier to attach to the strut assembly 404. Additionally, the wall of the artery is insulated from the struts 408 by restraining straps 434. This device also has the benefits of being low profile and allows the use of any guide wire, as well as allowing for guide wire exchanges. This particular embodiment, like the previous embodiments, allows for the exchange of the interventional device in an over-the-wire procedure.

Referring now to FIGS. 33–38, two different embodiments of the present invention are shown which utilize a different mechanism for deploying the struts of the strut assembly. In FIG. 33, an embolic protection device 500 is shown as including a filter assembly 502 having an expandable strut assembly 504 and a filter element 506. As with the other embodiments, the strut assembly 504 includes a plurality of radially expandable struts 508 which are utilized to place the filter element 506 into an expanded position within the patient's vasculature. The mechanism for deploying the radially expandable struts 508 utilizes a number of self-expanding deployment members 510 which are attached to each of the struts 508 making up the expandable strut assembly 504. The self-expanding deployment members 510 are made from self-expanding materials, such as nickel-titanium alloy, which can be compressed to a very small profile and expanded to a rather large expanded position which moves the struts 508 and filter 506 to the fully expanded position. As is seen in FIGS. 33 and 34, there are a number of deployment members 510 which are located along the length of each of the struts 508. There is a proximal set 512 of deployment members 510 located along the proximal region of each strut 508. There is a center set 514 of deployment members 510 located at the center section of each stent 508. As can be seen in FIG. 34, the coverage of the filter element 506 begins at this center set 514. A third or distal set 516 of deployment members 510 is located on the struts in the region where the filter element 506 is placed to enhance the deployment of each strut.

As can be seen in FIG. 37, each deployment member 510 is basically a collapsible piece of self-expanding material which will expand to a final size when fully deployed. FIG. 38 shows an end view of the center set 514 and distal set 516 of the deployment members as they are located along the struts 508. Each of the sets of deployment members 510 will fully expand to a quarter-circle segment which cooperate to form a "ring" when the sets of the deployment members are fully expanded. As a result of using this particular construction, the filter element 506 will fully deploy and maintain a circular-shaped opening 507 which will contact the wall of the artery when the embolic protection device 500 is deployed within the patient's vasculature.

In the first embodiment of this particular embolic protection device 500, the distal end 518 of the expandable strut assembly 504 is permanently attached to the guide wire 520. The proximal end 522 of the strut assembly 504 is, in turn, attached to an elongated outer tubular member 524 which has a proximal end (not shown) which extends outside of the patient's vasculature along with the proximal end of the guide wire. The embolic protection device 500 can be moved into its collapsed position as shown in FIG. 35 by simply retracting the proximal end of the outer tubular member 524 to impart an outward force on the ends of the strut assembly 504. The force which will be imparted on the ends of the strut assembly 504 should be sufficient to collapse each deployment members 510 which will, in turn, cause each of the struts 508 to move back to the collapsed position. As with the other embodiments, once the struts 508 are placed in its collapsed position, the filter element 506 will likewise collapse and will trap and encapsulate any embolic debris which may have been trapped within the filter element 506.

Referring now to FIG. 36, an alternative embodiment of an embolic protection device similar to the one shown in FIG. 33 is disclosed. This particular embolic protection device 530 utilized the same filter assembly 502 and strut assembly 504 as shown in the previous embodiment. The differences between the strut assembly 532 of the embolic protection device 530 includes the elimination of the proximal set 512 of deployment members 510 from this strut assembly 532. Otherwise, the filter assembly 534 is virtually the same as the filter assembly 502 of the previous device 500.

The distal end 518 of the strut assembly 534 is also permanently affixed to the guide wire 520 in this particular embodiment. The proximal end of this particular strut assembly 534 is free to move longitudinally along the length of the guide wire when being moved from a deployed to a contracted position and visa versa. The mechanism for deploying the filter assembly 532 is restraining sheath 536 which places a force on the and deployment members 510 which prevent them from expanding until the restraining sheath 536 is retracted. Once the embolic protection device 530 is properly in place within the patient's vasculature, the proximal end (not shown) of the restraining sheath 536 is retracted to allow the deployment members 510 to open the struts 508 and filter element 506 to the fully expanded position within the artery. When the device is to be removed from the patient's vasculature, the restraining sheath 536 is placed against the proximal region 535 of the struts 508 and is retracted over the struts to force the deployment members 510 back into their collapsed position. Thereafter, any embolic debris which may be trapped within the filter element 506 is retained and safely removed from the patient's vasculature. A proximal set of deployment members 510 may not have to be used with this particular embodiment since there may be a need to reduce the amount of expansive force applied to the struts in this proximal region 535. However, it is still possible to place a first set of deployment members at this proximal region 535 provided that the sheath has sufficient strength to collapse the struts in this region.

The filter element 506 shown in FIGS. 33–38 is made from a mesh material which allows blood to perfuse therethrough but captures embolic material. The mesh material can be made from any interwoven fabric which contains small size openings which will trap the desired size of emboli. Alternatively, the filter 506 can be made from a polymeric material with perfusion openings found therein.

Referring now to FIGS. 39A, 39B and 40, an alternative strut assembly 550 which could be utilized in conjunction with any of the filtering assemblies made in accordance with the present invention is shown. The strut assembly 550 includes struts 552 and a deployment member 554 which is used to expand the struts 552 into the deployed expanded position. This deployment member 554 acts in the same manner as the previously described deployment members in that the deployment member 554 can be made from a self-expanding material which will expand to a final size once fully deployed. The deployment member 554 also could be collapsed to an unexpanded position when an external force is placed on the assembly to maintain the deployment member 554 in its collapsed position. As can be seen in FIGS. 39A, 39B and 40, the deployment member 554 has a serpentine pattern made of peaks 556 and valleys 558 which are accordingly attached to the struts 552 of the assembly 550. In these particular embodiment of the invention, the deployment member 554 has a sinusoidal wave pattern which includes the peaks 556 and valleys 558 that are attached to the ends of the struts 552. This particular pattern allows the struts to be offset or staggered from one another to allow the assembly 550 to be collapsed to a lower profile which enhances the assembly's ability to reach tighter lesions and to be maneuvered into even distal anatomy. The staggered strut design also increases the assembly's flexibility which enhances the ability to move the assembly within the patient's anatomy. A filter element could be likewise placed over or within the struts 552 to create a composite filter assembly. The deployment member 554 provides complete vessel wall opposition, forcing a seal of the filter edge to the wall of the vessel. The deployment member 554 can have multiple geometries without departing from the spirit and scope of the present invention. This particular strut assembly 550 also could be created from a lazed hypotube which incorporates the staggered strut design. The number of struts can be varied along with the particular lengths of the struts. Alternatively, the deployment member 554 could be made from a separate piece of material from the struts and could be attached using methods such as soldering, brazing or bonding, using suitable adhesives. As can be seen from FIGS. 39A and 39B, the attachment of the struts 552 to the peaks 556 and valleys 558 of the deployment 554 can be varied as shown. Both of these particular designs allow the strut assembly to be collapsed to a low profile.

Figure 41:
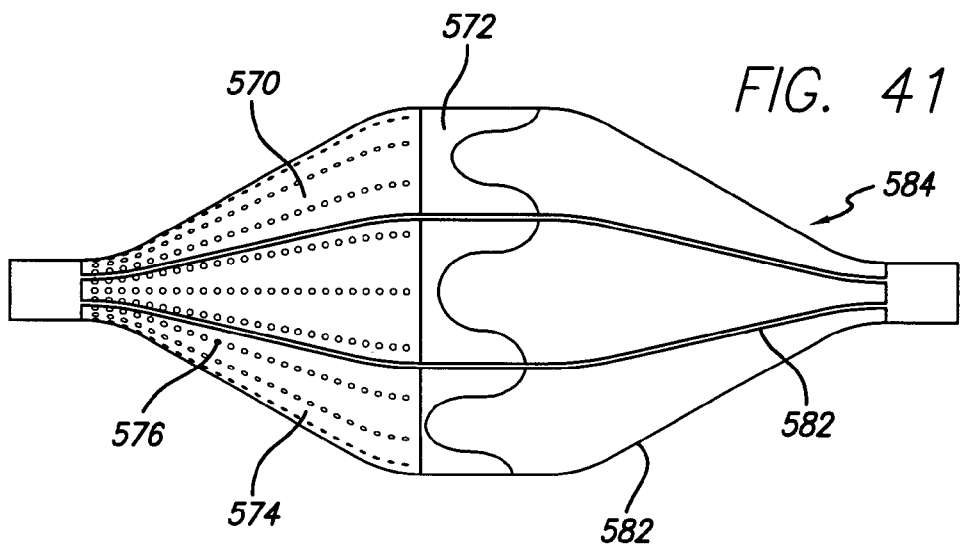
FIG. 41 is an alternative embodiment of a filter assembly with an alternative filter element made in accordance with the present invention.
Figure 42:
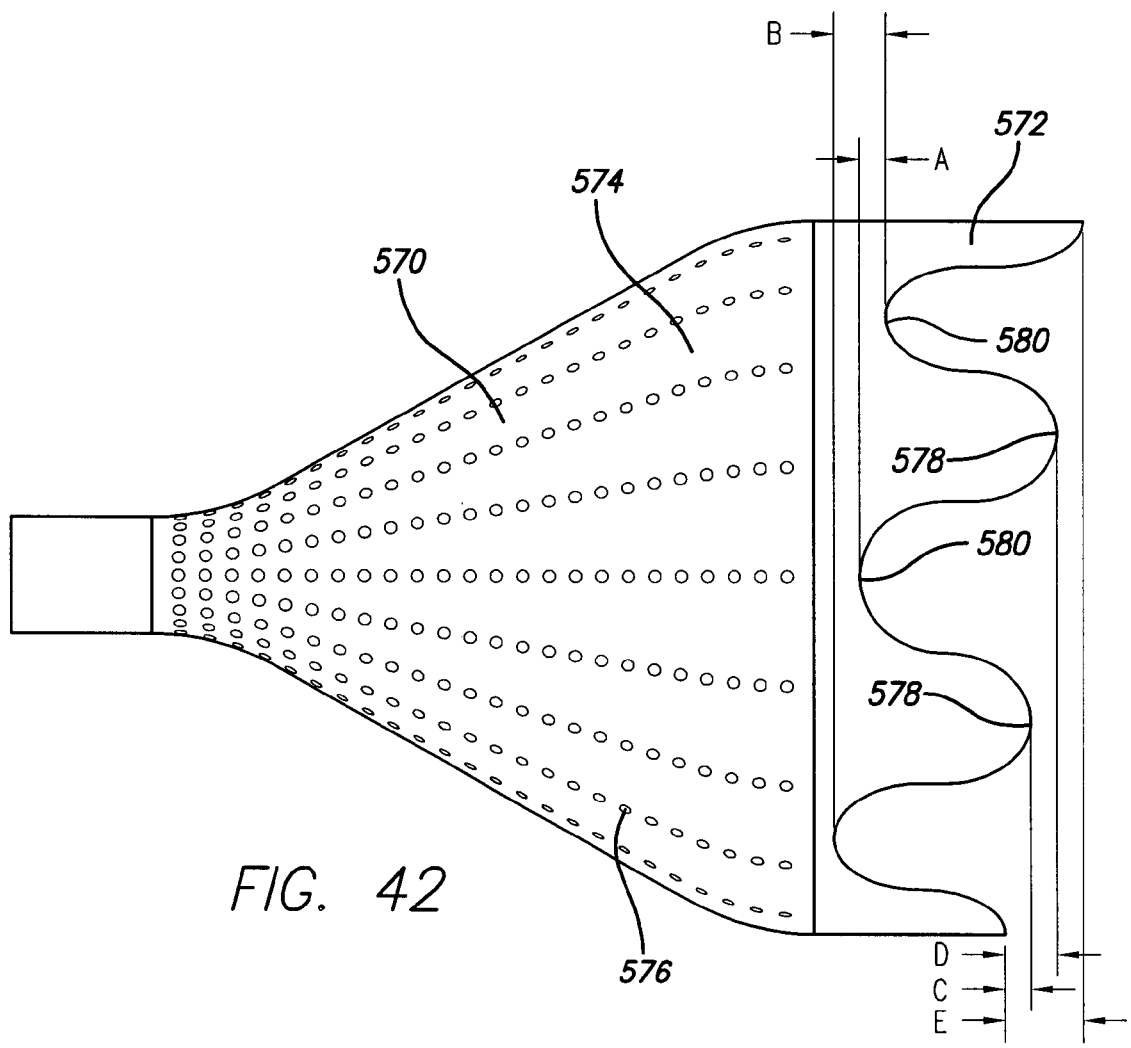
FIG. 42 is an enlarged side view of the filter element of the filtering assembly of FIG. 41.

Referring now to FIGS. 41 and 42, an alternative filter element 570 with an angulated filter edge 572 is shown which is used to help in the loading and retrieval of the embolic protection device into a restraining sheath. The filter element 570 is similar to the filters previously described in that the filter element 570 includes a central section 574 which has a plurality of openings 576 that are utilized in filtering the embolic debris. The filter element 570 includes an edge 572 which is configured similar to a crown, with pointed peaks 578 and valleys 580. This configuration of the filter edge 572 allows the filter to be incrementally introduced into the restraining sheath, thus preventing the material from entering the sheath all at once. As can be seen in FIGS. 41 and 42, the edge 572 has a somewhat sinusoidal configuration which would reduce the stress concentration in the valley regions 580 of the filter. The peaks 578 of the filtering element 570 would be matched up with the struts 582 of the strut assembly 584. The number of peaks 578 could vary with the number of struts 582 on the strut assembly 584. In this particular embodiment, the filtering element 570 could be placed within the inside of the strut assembly 584, or, alternatively, the filter could be placed on the outside of the assembly 584. It should be appreciated that other filter elements described herein also could either replace on the inside or outside of the strut assembly used in connection with a particular filtering assembly. As the strut assembly 584 is being loaded or retrieved, the peaks 578 of the filter element 570 would enter the restraining sheath first. This prevents all of the filtering material from entering the sheath at once, causing a gradual and incremental loading of the filter element 570 into the sheath. Additionally, dimensions A and B shown in FIG. 42 show the difference in the valley depths in the sinusoidal pattern of the filter edge 572. This allows for a variety of configurations. One possible configuration is A=B=0. Additionally, B≧A≧0 so that the loading of the filter into the sheath will be in a smooth operation. This particular configuration eliminates or virtually eliminates all of the valley portions 580 from entering the sheath at the same time. The filter edge 572 may or may not have openings 576. The peaks 578 can also have varying heights. Dimensions C, D and E shown in FIG. 42 shows a difference in the peak heights on the sinusoidal pattern of the filter edge 572. This particular pattern also allows for a variety of configurations. One possible configuration is C=D=E=0. Additionally, E≧D≧C≧0 to correspond, or alternatively, not to correspond with the depths of the valleys 580.

Referring now to FIGS. 45–48, an alternative embodiment of an embolic protection device 640 is disclosed. This particular embolic protection device 640 utilizes a filter assembly 642 and strut assembly 644 which is somewhat similar to the strut assembly 550 shown in FIG. 39B. The particular strut assembly 644 includes a set of proximal struts 646 attached to a deployment member 648 which moves between an unexpanded or collapsed position and an expanded position in the same manner as the previously described deployment members. This deployment member 648 can be made from a self-expanding material which will expand to a final diameter once fully deployed. This deployment member 648 is collapsible when a sheath or sleeve is placed over the assembly. A set of distal struts 650 are attached to the deployment member 648 and also are expandable and collapsible with the deployment member 648. The deployment member 648 has a substantial V-shaped wave pattern which permits the strut assembly to more easily collapse to a low profile. A filter element 652 is attached to the strut assembly 644 and has a shape much like the filter element 570 shown in FIGS. 41 and 42. The filter element 652 includes an edge portion 654 which is configured with alternating peaks 656 and valleys 658. This configuration of the filter edge portion 654 also allows the filter to be incrementally introduced into the restraining sheath 660, thus preventing the filtering material from entering the sheath 660 all at once. As can be seen in FIGS. 45 and 46, the filter element of 652 has a somewhat tulip-like shape due to the construction of the peaks 656 and valleys 658. As is shown in FIG. 46, the peaks 656 of the filter element 652 are matched up with the wave pattern of the deployment member 648 and are attached thereto using adhesives or other bonding techniques. The filter can extend along and outside the struts with the edge portion 654 adhesively attached to the inside edge of the deployment member 648.

The filter element 652 can be made from a mesh material which allows blood to profuse therethrough but captures embolic material. The mesh material can be made from interwoven fabric which contains small size openings which would trap the desired size of emboli. Alternatively, the filter elements 652 can be made from a polymeric material with profusion openings formed therein.

In this particular embodiment of the embolic protection device 640, an obturator 662 is located at the distal end 664 of the filter assembly 642 and is utilized for obtaining smooth deployment through the patient's vasculature. This particular obturator 662 acts much like the sphere 56 shown in FIGS. 1 and 2 which prevents "snow plowing" of the embolic protection device as it is being delivered through the patient's arteries. This obturator 662 also has a smooth surface which tapers from a smaller diameter distally to a larger diameter that corresponds to the outer diameter of the restraining sheath 660. A smooth outer surface is created when the obturator 662 and restraining sheath 660 are placed adjacent to each other. This obturator can be made from a material such as PEBAX 40D, or other polymeric materials or alloys which are capable of performing the desired function.

Figure 48:
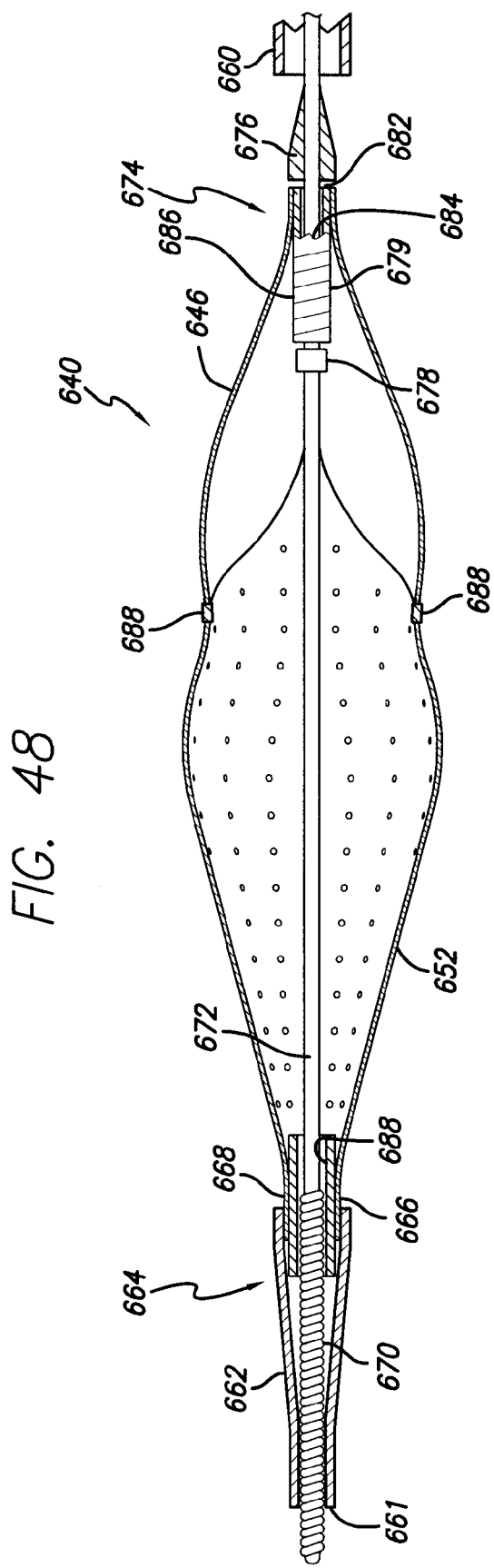
FIG. 48 is a cross-sectional view of the embolic protection device of FIG. 46.

As is shown in the cross-sectional view of the device in FIG. 48, the obturator 660 is attached (via adhesive or other bonding material) to a tubular member 666, which is made from a material such as polyimid tubing. This tubular member 666 is adhesively or otherwise attached to the distal ends 668 of the distal struts 650. The tubular member 666 is not, however, adhesively attached to the guide wire 672, but rather, is allowed to rotate free around the coils 670. The obturator 662 also extends over a portion of the coils 670 of the guide wire 672 and is free to rotate about the coils 670. The proximal end 674 of the filter assembly 642 is attached to the guide wire 672 in such a manner to allow it to rotate freely about or "spin" on the guide wire 672 as well. The filter assembly 642 is attached to the guide wire 672 much like the embodiment shown in FIGS. 1 and 2. As can be seen in FIGS. 46 and 48, a stop fitting 676 is attached to the guide wire 672 to prevent the proximal end 674 from moving past that particular fitting. A second stop fitting 678, located within the filter assembly 642, helps prevent the filter assembly 642 from moving axially any substantial distance along the guide wire 672.

The proximal ends 680 of the proximal struts 646 are attached to a pair of tubular segments 682 and 684 which are in a coaxial relationship. A marker band (not shown) can be partially sandwiched between these two tubular segments 682 and 684 to provide the physician with a reference when placing the embolic protection device 640 in the patient's vasculature. The tubular segments 682 and 684 are adhesively affixed to each other and the marker band to form a composite tubular extension member 686. This composite tubular extension member 686 extends between the two stop fittings 676 and 678. The extension member 686 may include a dampening element 679 which is formed on a portion of the segment to help dampen some of the vibratory motion which may be transmitted along the guide wire 672. It can be cut into the extension member 686 much like the dampening element 38 is cut on the embodiment shown in FIGS. 1–3. It should be appreciated that this extension member 686 can be formed from a single piece of tubing and need not be two separately formed segments glued together. This extension member 686 also helps to increase the torque response of the embolic protection device 640 on the guide wire and allows more room for the filter assembly to rotate, if needed.

Additional marker bands 688 can be placed on the strut assembly 644 to provide additional reference sources for the physician to rely on when maneuvering the device in the patient's arteries. Like the previously described filter assemblies, this particular filter assembly 642 will remain in place within the patient's vasculature, once deployed therein, and will remain stationary even if the guide wire 672 is rotated by the physician during an exchange of interventional devices along the guide wire. As a result, there is less chance of trauma to the patient's artery at the location where the filter assembly 642 contacts the wall of the artery.

The particular configuration of the filter assembly 640 and its attachment to the guide wire 672 allows the physician to eliminate any air bubbles which may be trapped within the restraining sheath 660 as it covers the filter assembly 642 in its collapsed state. The present design allows the physician to flush a solution, such as saline, through the lumen of the restraining sheath 660 out to its distal end to cause any trapped air bubbles to be vented through the distal opening 661 of the obturator 662. As a result, the possibility that an air bubble possibly could be released into the patient's artery can be virtually eliminated by thoroughly flushing saline through the restraining sheath 660 to eliminate any trapped air bubbles. The tubular member 666 acts as a conduit for the saline to flow out of the obturator 662. Fluid is allowed to flow through the restraining sheath 660 through the inner lumen 688 of the tubular member 666 and out the distal opening 661 of the obturator 662.

Referring now to FIGS. 49 and 50, another alternative embodiment of a embolic protection device 690 is shown. In this particular embodiment, the filter assembly 692 includes a strut assembly 694 which includes only a proximal set of struts 696 that are attached to a deployment member 698. This particular filter assembly 692 is somewhat similar to the assembly shown in FIGS. 45–48, except that a distal set of struts are not utilized. The filter element 700 is attached directly to the deployment member 698 and has a distal end 702 which is attached to a segment of tubing 704. This tubing 704 extends from the proximal end 706 of the filter assembly 692 to the distal end 702 of the filter 700 and is rotatable on the guide wire 710.

In this particular embodiment, the proximal end 706 of the filter assembly 692 is attached directly to a tubing member 704. The proximal 706 of the filter assembly 692 terminates in a collar 708 as is shown in FIGS. 49 and 50. It is attached to the tubing 704 using adhesives or other bonding techniques. This entire filter assembly 692, which includes the tubing member 704, is rotatable upon the guide wire 710 to allow the device to remain stationary within the patient's artery even if the guide wire is rotated by the physician during a device exchange. A stop fitting 712 located on the guide wire 710 acts to prevent the filter assembly 692 from moving axially along the length of the guide wire 710. The distal end 714 of tubing member 704 abuts against the most proximal end of coil 716 formed on the guide wire 710. In this manner, the coil 716 acts as a stop fitting to prevent axial movement of the tubing member 704 along the guide wire 710.

The distal end 702 of the filter 700 is attached to the tubing member 704 using adhesives or other bonding agents. The distal end 702 of the filter does not have to be movable axially along the guide wire, as with the previous embodiments, since the filter 700 itself is pliable and will move as the strut assembly 694 moves between its expanded and collapsed positions. When the strut assembly 694 is moved from its unexpanded to expanded position, the filter 700 will "stretch" somewhat as the deployment member 698 and struts 696 move outward and somewhat away from the distal end 702 of the filter 700. As with the previous embodiments, a restraining sheath (now shown) is utilized to move the filter assembly 692 between its expanded and unexpanded positions.

Referring now to FIGS. 51A, 51B, 52A and 53B, an embodiment of an embolic protection device of the present invention including a structure intended to prevent back flow of blood through the embolic protection device is shown incorporated into the structure of the embodiment of the embolic protection devices depicted in FIGS. 49–50. It should be understood that while this embodiment providing for one way flow of blood through the filter is described with reference to the filter embodiment depicted and described with reference to FIGS. 49–50, the embodiment may be incorporated into any of the filter assemblies described herein, and its use is limited only by the design requirements of a particular embodiment of filter assembly.

The filter element 770 of filter assembly 755 is attached directly to the deployment member 765 and has a distal end 775 which is attached to a segment of tubing 780. This tubing 780 extends from the proximal end 785 of the filter assembly 755 to the distal end 775 of the filter 770 and is rotatable on the guide wire 754.

In this embodiment, the proximal end 785 of the filter assembly 755 is attached directly to the tubing member 780. The proximal end 785 of the filter assembly 752 terminates in a collar 790. Collar 790 is attached to the tubing 780 using adhesives or other bonding techniques. This entire filter assembly 755, which includes the tubing member 780, is rotatable upon the guide wire 754 to allow the device to remain stationary within the patient's artery even if the guide wire is rotated by the physician during a device exchange. A stop fitting 795 located on the guide wire 754 acts to prevent the filter assembly 755 from moving axially along the length of the guide wire 754. The distal end 797 of tubing member 780 abuts against the most proximal end of coil 800 formed on the guide wire 754. In this manner, the coil 800 acts as a stop fitting to prevent axial movement of the tubing member 780 along the guide wire 754.

The distal end 775 of the filter 770 is attached to the tubing member 780 using adhesives or other bonding agents. The distal end 775 of the filter does not have to be movable axially along the guide wire, as with the several of the other embodiments described previously, since the filter 770 itself is pliable and will move as the strut assembly 760 moves between its expanded and collapsed positions. When the strut assembly 760 is moved from its unexpanded to expanded position, the filter 770 will "stretch" somewhat as the deployment member 765 and struts 760 move outward and somewhat away from the distal end 785 of the filter 770. As with the previous embodiments, a restraining sheath (not shown) may be utilized to move the filter assembly 755 between its expanded and unexpanded positions.

Referring now to FIGS. 51B and 52B, one embodiment of a flow control structure providing for one way flow of blood through the filter 770 is described. Filter 770 comprises a flexible body member 802 perforated by one or more openings or holes 805 that extend through the thickness of body member 802. The openings or holes 805 are sized to capture embolic material while allowing blood to flow through the filter. Body member 802 further includes a flexible flap 810 that extends over one or more of the openings or holes 805 in the body member 802. As depicted in FIG. 51B, when the filter 750 is expanded within a vessel 752, blood flows from the distal end 785 of the filter assembly 755 towards the proximal end 775 of the filter assembly 755. In general, because the filter is expanded across the lumen of the vessel 752, any embolic material contained within the blood will be trapped within the filter 770 and the blood will flow through openings or holes 805 to continue on through the vessel 752.

For a variety of reasons, it may be necessary to remove trapped embolic material from the filter 770 while the filter assembly 755 is expanded within the vessel 752, such as prior to collapse and removal of the filter assembly 755 from the vessel after completion of a surgical procedure. As depicted in FIGS. 52A and 52B, removal of such embolic material from the filter 770 may be accomplished by introducing an aspiration catheter 815 onto the guidewire 754 and positioning the distal end 820 of the aspiration catheter suitably close to the filter 770 so that suction from the distal end 820 of the catheter may vacuum the trapped embolic material from the filter 770. As shown in FIG. 52B, application of suction to the embolic material causes a decrease in pressure within the filter 770, which causes the flexible flap 810 to close down upon the outer surface of the body member 802, acting as a one-way valve. When flexible flap 810 closes down upon opening or hole 805, the opening or 805 is sealed by flap 810 to prevent blood flow from the exterior of the filter assembly 755 through opening or hole 805 into the interior of the filter 770. In this manner, the efficiency of the aspiration of embolic material is improved, resulting in faster removal of the trapped embolic material from the filter 770.

While it is anticipated that all of the openings or holes 805 perforating the body member 802 of filter 770 may associated with flexible flaps 810 to provide for sealing of the openings or holes 805, it is also contemplated that only a portion of the openings or holes 805 formed within body member 802 may have flexible flaps 810 associated therewith. In this manner, more or less of the openings or holes 805 may be sealable upon introduction of an aspiration catheter to provide for a predetermined amount of blood flow through a portion of holes 805 to facilitate suction of embolic material from filter 770 without collapsing filter 770.

Figure 53:
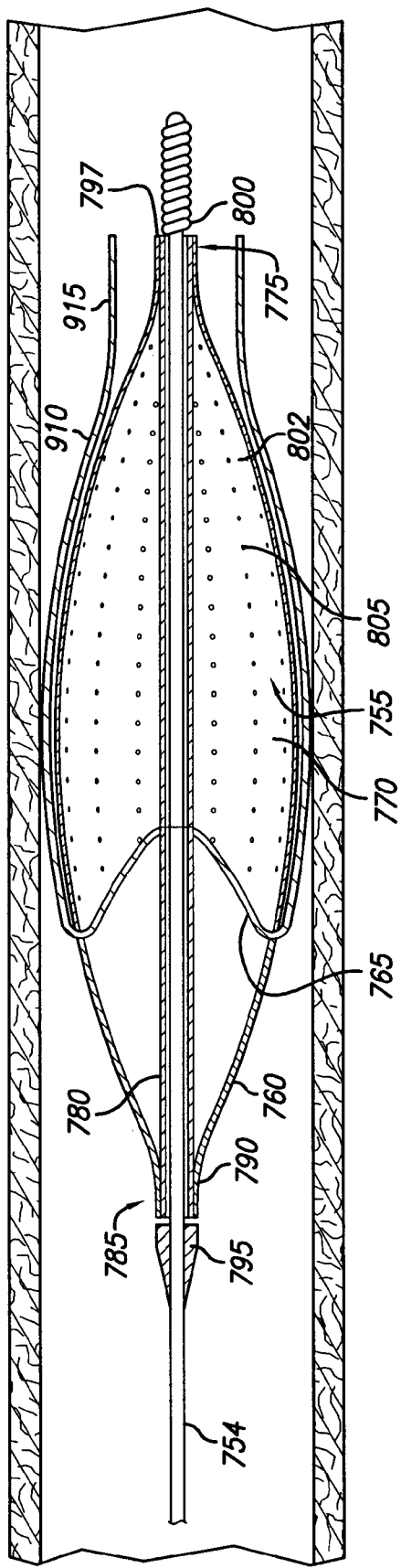
FIG. 53 is a cross-section view of another embodiment of an embolic protection device made in accordance with the present invention incorporating a sheath to provide for controlled backwards flow of blood through the device during aspiration of embolic material trapped in the device, showing the sheath in an open position.
Figure 54:
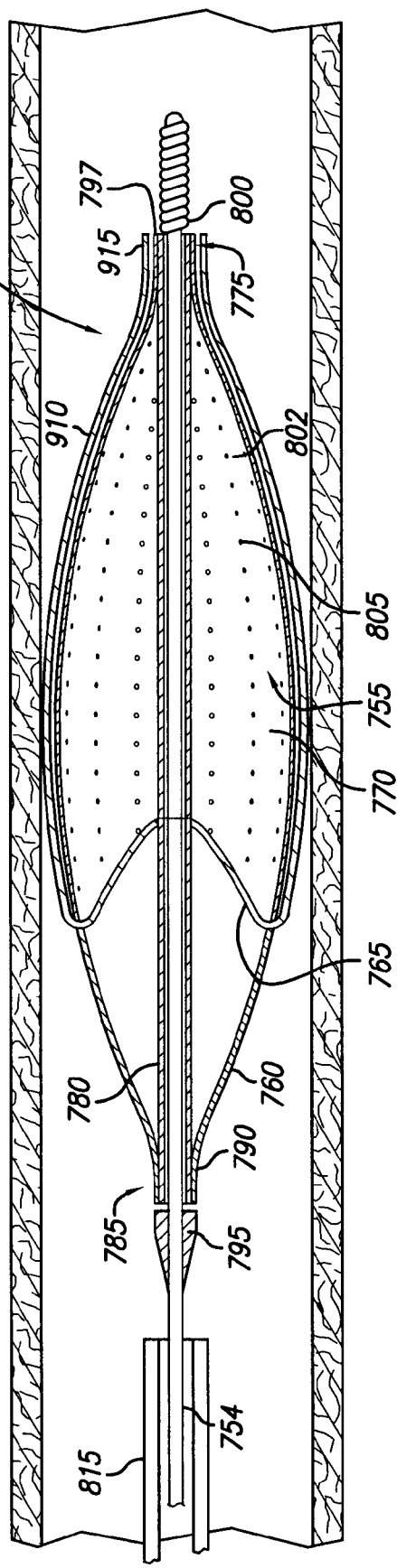
FIG. 54 is a cross-sectional view of the device of FIG. 53 showing the sheath in a closed position during aspiration of embolic material trapped within the embolic protection device.

Referring now to FIGS. 53 and 54, another embodiment of a structure intended to control the back flow of blood through the embolic protection device of the present invention is shown incorporated into the structure of the embodiment depicted in FIGS. 49–50. It should be understood that while this embodiment providing for one way flow of blood through the filter is described with reference to the filter embodiment depicted and described with reference to FIGS. 49–50, the embodiment may be incorporated into any of the filter assemblies described herein, and its use is limited only by the design requirements of a particular embodiment of filter assembly.

Figure 55:
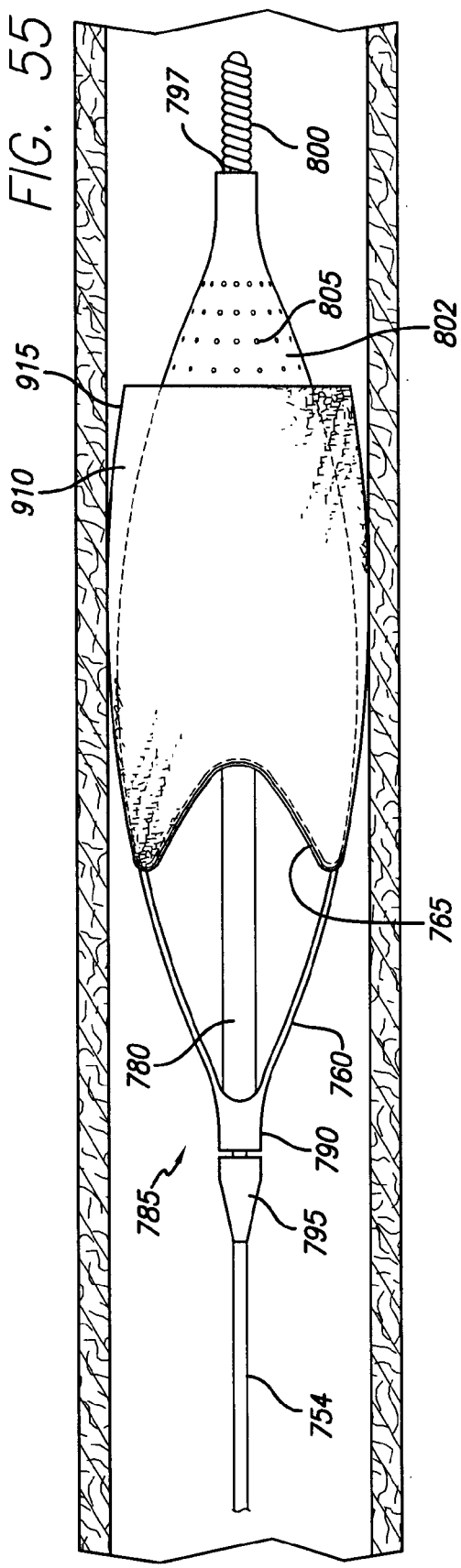
FIG. 55 is a cross-section view of another embodiment of an embolic protection device made in accordance with the present invention incorporating a sheath to provide for controlled backwards flow of blood through the device during aspiration of embolic material trapped in the device, showing the sheath in an open position.
Figure 56:
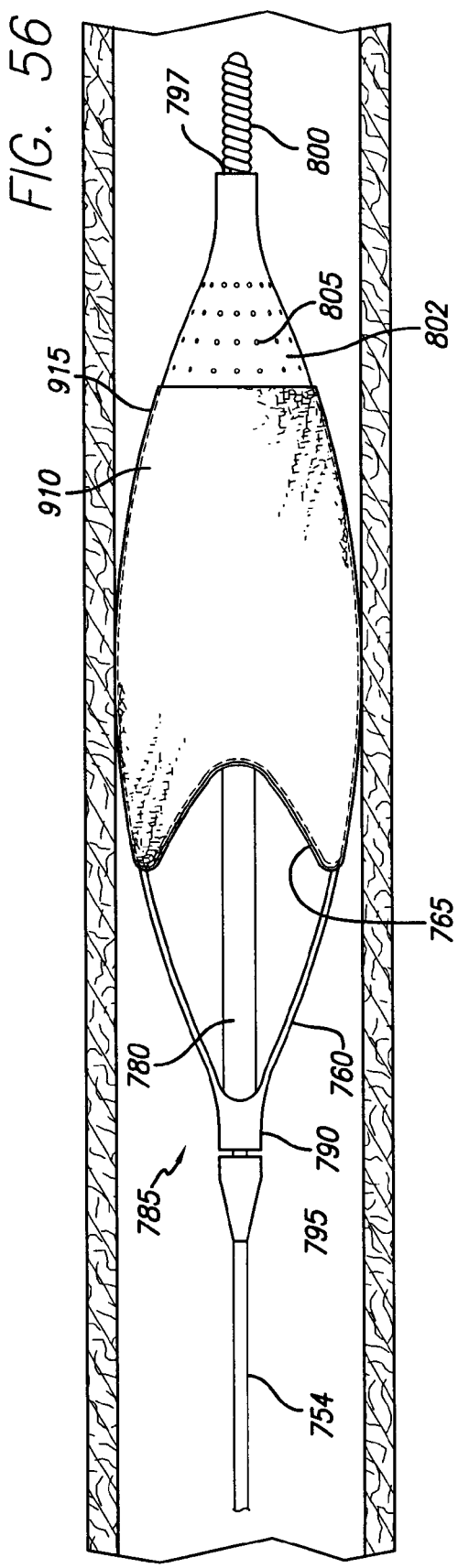
FIG. 56 is a cross-sectional view of the device of FIG. 55 showing the sheath in a closed position during aspiration of embolic material trapped within the embolic protection device.

In this embodiment of an embolic protection device 850, a sheath or sleeve 910 having a proximal end 912 and a distal end 915 is mounted to the external surface of the body member 802 of the filter 770 by bonding the proximal end 912 of the sheath or sleeve 910 to the external surface of body member 802 using a suitable adhesive. Alternatively, the sheath or sleeve 910 and the body member 802 may be formed in such a manner that the proximal end 912 of sheath or sleeve 910 may be considered an extension of body member 802, similar to the flexible flap 810 depicted in FIGS. 51B and 52B, the difference being that flap 810 is formed to seal a single opening or hole 805, while the sheath or sleeve 910 may cover and seal multiple openings or holes 805. While the sheath 910 is depicted in FIGS. 53 and 54 as covering all of the openings or holes 805 in the body member 802 of filter 870, it is contemplated that sheath or sleeve 910 may be formed or mounted on the filter 770 in such a manner so that only a portion of the openings or holes 805 in the body member 802 are covered and sealed by the sheath or sleeve 910. Such an embodiment is shown in FIGS. 55 and 56. As can be seen in these figures, the sheath 910 does not extend past distal openings 805 created on the filter 870.

As shown in FIG. 53, during typical use of the embolic protection device 850 when it is expanded within the vessel 752, blood carrying embolic material flows into the filter assembly 755 where the embolic material is trapped within the filter 770 and the blood flows through holes 805 and continues on its passage through vessel 852. When suction is applied to filter 770 using an aspiration catheter 815, as depicted in FIG. 54, the suction reduces the pressure within filter 770, causing the sheath or sleeve 910 to be drawn onto the surface of body member 802 by the differential in pressure between the interior of the filter 770 and the exterior of the filter 770. When the sheath or sleeve 910 is drawn onto the exterior surface of the body member 802, the sheath or sleeve 910 occludes one or more of the openings or holes 805 in the body member 802, thus reducing or eliminating, depending on the design of the sheath, backwards flow of blood in the filter 770. Referring now to the embodiment of FIGS. 55 and 56, the sheath 910 operates as described above to occlude one or more openings 805 in the body member 802, except that a controlled amount of backflow will be developed through the distal most openings 805 which will not be covered by the sheath 910 when suction is applied to the filter. It should be appreciated that the amount of backflow which can be developed can be varied, as needed, by varying, for example, the length of the sheath and the number of openings to be occluded by the sheath as well as the number of openings which are not covered by the sheath.

As shown in FIGS. 53 and 54, the distal end 915 of the sheath or sleeve 910 may extend across the distal end 775 of the filter assembly 755 to effectuate a seal. Alternatively, the distal end 915 of the sheath or sleeve 910 may extend only a portion of the way towards the distal end 775 of the filter assembly 755, as shown in the embodiment of FIGS. 55 and 56 thus allowing some of the openings or holes 805 to remain uncovered during aspiration, providing for a predetermined amount of back flow of blood into the filter 770 to prevent collapse of the filter 770 during aspiration. It will be understood that the same effect may be obtained by locating the proximal end 912 of the sheath or sleeve 910 at a position on the external surface of the body member 802 so that a portion of the openings or holes 805 adjacent to the proximal end of the filter 770 are left uncovered. Alternatively, the sheath or sleeve 910 of the present invention is not required to extend completely around the filter 770. It is contemplated that various embodiments, such as an embodiment where the multiple sheaths or sleeves in the form of strips or flaps extending along the longitudinal axis of the filter 770 and covering zones or groups of openings or holes 805, while leaving other zones or groups of openings or holes 805 uncovered will achieve the desired effect of improving removal of embolic material while allowing a predetermined amount of back flow of blood into the filter during suction to prevent collapse of the filter. Such an embodiment is shown in FIGS. 57 and 58. As can be seen in FIGS. 57 and 58, several sheaths or sleeves 910 are located along the length of the filter 770 creating zones that are covered by the sheaths or sleeves 910 and zones of openings that remain uncovered.

Referring now to FIGS. 43 and 44, a simple locking mechanism 600 for expanding and collapsing the filter assembly described herein are shown. These particular mechanisms are useful whenever the embolic protection device utilizes an inner shaft member and outer tubular member for moving the strut assemblies into the expanded or collapsed position. Referring first to FIG. 43, the proximal end 602 of the outer tubular member 604 is shown with a locking mechanism 600 which can be utilized to lock the embolic protection device in either an expanded or unexpanded position. The locking mechanism 600 includes an elongated slot 606 which is cut into the wall of the outer tubular member 604 and includes a first locking position 608 and a second locking position 610. The inner shaft member 612, which can be either a solid shaft such as a guide wire or a hollow tubular shaft, has a raised dimple 614 which moves within this elongated slot 606. This raised dimple 614 can be moved into either the first locking position 608 or second locking position 610 to either maintain the filter assembly in an expanded or unexpanded position. It should be appreciated that only two locking positions are shown on this particular embodiment, however, it is possible to use a number of different locking positions if the user desires to have several expanded positions. If the filter assembly is self-expanding, then a removable handle that pushes and pulls the inner and outer members could be used. The handle would push/pull the inner and outer members to hold the assembly closed, then be removed so that other interventional devices could be passed over the inner tubular member. Thereafter, the handle could be placed back onto the proximal ends of the inner and outer members to collapse and remove the filter assembly.

The proximal end 602 of the outer tubular member includes a small section of knurling 616, as does the inner shaft member 612, which provides the physician with a surface to grip when holding and maneuvering the proximal ends of these devices. The locking mechanism 600 can also include a biasing spring 618 located within the inner lumen 620 of the outer tubular member 604 for biasing the inner shaft member 612 with an outward force which maintain the raised dimple 614 near the first locking position 608. This biasing mechanism includes a shoulder region 621 located at the proximal end of the outer tubular member and a collar 622 located on the inner shaft member 612. The force of the spring 618 again helps to maintain the dimple 614 at or near the first locking position 608. Such a mechanism is preferable when the device is designed to be maintained in an unexpanded position until it is ready to be deployed. It may be beneficial to keep the filter assembly in its unexpanded position until ready for use since it is possible to cause damage to the filter assembly if left in an expanded position. When the filter assembly is desired to be placed into the deployed or expanded position, the physician merely grasps the proximal end of the inner shaft member and pulls it back until the dimple 614 is placed into the second locking position 610. When the strut assembly is made from elements which are self-expanding, then there may not be a need to have a biasing spring 618 since the struts on the strut assembly will act somewhat like a biasing spring to maintain the filter assembly in an expanded position.

The strut assemblies of the present invention can be made in many ways. However, the preferred method of making the strut assembly is to cut a thin-walled tubular member, such as nickel-titanium hypotube, to remove portions of the tubing in the desired pattern for each strut, leaving relatively untouched the portions of the tubing which are to form each strut. It is preferred to cut the tubing in the desired pattern by means of a machine-controlled laser.

The tubing used to make the strut assembly may be made of suitable biocompatible material such as stainless steel. The stainless steel tube may be alloy-type: 316L SS, Special Chemistry per ASTM F138-92 or ASTM F139-92 grade 2. Special Chemistry of type 316L per ASTM F138-92 or ASTM F139-92 Stainless Steel for Surgical Implants in weight percent.

The strut size is usually very small, so the tubing from which it is made must necessarily also have a small diameter. Typically, the tubing has an outer diameter on the order of about 0.020–0.040 inches in the unexpanded condition. The wall thickness of the tubing is about 0.076 mm (0.003–0.006 inches). For strut assemblies implanted in body lumens, such as PTA applications, the dimensions of the tubing maybe correspondingly larger. While it is preferred that the strut assembly be made from laser cut tubing, those skilled in the art will realize that the strut assembly can be laser cut from a flat sheet and then rolled up in a cylindrical configuration with the longitudinal edges welded to form a cylindrical member.

Generally, the hypotube is put in a rotatable collet fixture of a machine-controlled apparatus for positioning the tubing relative to a laser. According to machine-encoded instructions, the tubing is then rotated and moved longitudinally relative to the laser which is also machine-controlled. The laser selectively removes the material from the tubing by ablation and a pattern is cut into the tube. The tube is therefore cut into the discrete pattern of the finished struts. The strut assembly can thus be laser cut much like a stent is laser cut. Details on how the tubing can be cut by a laser are found in U.S. Pat. Nos. 5,759,192 (Saunders) and 5,780,807 (Saunders), which have been assigned to Advanced Cardiovascular Systems, Inc.

The process of cutting a pattern for the strut assembly into the tubing generally is automated except for loading and unloading the length of tubing. For example, a pattern can be cut in tubing using a CNC-opposing collet fixture for axial rotation of the length of tubing, in conjunction with CNC X/Y table to move the length of tubing axially relative to a machine-controlled laser as described. The entire space between collets can be patterned using the $CO_2$ or Nd:YAG laser set-up. The program for control of the apparatus is dependent on the particular configuration used and the pattern to be ablated in the coding.

A suitable composition of nickel-titanium which can be used to manufacture the strut assembly of the present invention is approximately 55% nickel and 45% titanium (by weight) with trace amounts of other elements making up about 0.5% of the composition. The austenite transformation temperature is between about −15° C. and 0° C. in order to achieve superelastecity. The austenite temperature is measured by the bend and free recovery tangent method. The upper plateau strength is about a minimum of 60,000 psi with an ultimate tensile strength of a minimum of about 155,000 psi. The permanent set (after applying 8% strain and unloading), is approximately 0.5%. The breaking elongation is a minimum of 10%. It should be appreciated that other compositions of nickel-titanium can be utilized, as can other self-expanding alloys, to obtain the same features of a self-expanding stent made in accordance with the present invention.

The strut assembly of the present invention can be laser cut from a tube of super-elastic (sometimes called pseudo-elastic) nickel-titanium (Nitinol) whose transformation temperature is below body temperature. After the strut pattern is cut into the hypotube, the tubing is expanded and heat treated to be stable at the desired final diameter. The heat treatment also controls the transformation temperature of the strut assembly such that it is super elastic at body temperature. The transformation temperature is at or below body temperature so that the stent is superelastic at body temperature. The strut assembly is usually implanted into the target vessel which is smaller than the diameter if the strut assembly in the expanded position so that the struts apply a force to the vessel wall to maintain the filter element in the expanded position.

The piece of tubular hypotube which can be utilized in accordance with the present invention to form the strut assemblies can be one continuous piece which forms both the outer tubular member and the strut assembly as well. In some of the embodiments disclosed herein, the strut assembly is shown as being made from a short segment of hypotube which is selectively cut to form the strut patterns. Thereafter, the proximal end of the strut assembly is bonded to, either by adhesives, welding, brazing or soldering to the distal end of the outer tubular member. However, these two separate pieces can be formed from a piece of single tubing in a preferred embodiment of the invention.

The dampening element which is shown in one of the embodiments of the present invention could also be used with any of the other embodiments disclosed herein. The dampening element could either be cut into the proximal end of the strut assemblies, as is shown in FIGS. 1 and 2, or an alternative dampening element could be attached to the strut assembly. For example, a separate spring made from a different material or similar material could be welded, brazed or soldered to the end of the strut assembly. Also, other dampening materials could be used besides a helical spring in order to achieve dampening. For example, segment of elastomeric material could be bonded to the strut assembly as well to act as a "shock absorber" for the system.

The outer tubular member could be made from various materials such as stainless steel, nickel-titanium alloy or materials which have memory. As discussed above, when using a separate outer member attached to the strut assembly, the distal end can be easily affixed to the strut assembly by known bonding methods. The inner diameter of the outer tubular member must of course be comparable to the outer diameter of the inner shaft member to allow the outer tubular member to slide in a coaxial arrangement. The inner shaft member can also be made from stainless steel, nickel-titanium alloys or shape-memory materials. In one embodiment, the inner shaft member is shown as a tubular member which has an inner lumen which allows the device to slide over a guide wire in an over-the-wire fashion. Other embodiments show the inner shaft member as a guide wire or guide wire-like shaft. Generally, when the inner shaft member is utilized as a guide wire, it should include an atraumatic guide wire coil tip to prevent injury to the vessel as the guide wire is being maneuvered through the patient's vasculature. It should be appreciated that the coil tip does not have to be placed directly next to the filtering assembly in those embodiments which utilize a guide wire as the inner shaft member. The filtering assembly could be placed much more proximal to the coil tip to create a short, distal segment of guide wire which may be pre-bent by the physician to aid in steering through the patient's vasculature.

Again, the tubing or hypotube which could be utilized to create the strut assembly can be a nickel-titanium alloy, such as Nitinol, or other shape-memory materials. It is also possible to utilize stainless steel to form the strut assembly as well. The strut assembly could also be made from a self-expanding material even in embodiments in which the outer tubular member and inner shaft member are utilized to provide the axial forces necessary to expand or contract the device during use. Additionally, the strut assembly could be either biased to remain in its collapsed position or expanded position as may be desired. It should be appreciated that the stent assembly can be made from either pseudo elastic NiTi stressed induced martensite or shape memory NiTi.

The polymeric material which can be utilized to create the filtering element include, but is not limited to, polyurethane and Gortex, a commercially available material. Other possible suitable materials include ePTFE. The material can be elastic or non-elastic. The wall thickness of the filtering element can be about 0.001–0.005 inches. The wall thickness may vary depending on the particular material selected. The material can be made into a cone or similarly sized shape utilizing blow-mold technology. The perfusion openings can be any different shape or size. A laser, a heated rod or other process can be utilized to create to perfusion openings in the filter material. The holes, would of course be properly sized to catch the particular size of embolic debris of interest. Holes can be lazed in a spinal pattern with some similar pattern which will aid in the re-wrapping of the media during closure of the vice. Additionally, the filter material can have a "set" put in it much like the "set" used in dilatation balloons to make the filter element re-wrap more easily when placed in the collapsed position.

The materials which can be utilized for the restraining sheath and recovery sheath can be made from similar polymeric material such as cross-linked HDPE. It can alternatively be made from a material such as polyolifin which has sufficient strength to hold the compressed strut assembly and has relatively low frictional characteristics to minimize any friction between the filtering assembly and the sheath. Friction can be further reduced by applying a coat of silicone lubricant, such as Microglide®, to the inside surface of the restraining sheath before the sheaths are placed over the filtering assembly.

In view of the foregoing, it is apparent that the system and device of the present invention substantially enhance the safety of performing certain interventional procedures by significantly reducing the risks associated with embolic material being created and released into the patient's bloodstream. Further modifications and improvements may additionally be made to the system and method disclosed herein without departing from the scope of the present invention. Accordingly, it is not intended that the invention be limited, except as by the appended claims.

What is claimed:

1. An embolic protection device for capturing embolic debris contained within a fluid flowing through a lumen of a vessel of a patient, comprising:
   a filtering assembly having a filter element having a wall defining an interior volume of the filter element and an exterior of the filter element, the wall of the filter element being capable of capturing embolic material while allowing fluid to flow from the interior volume to the exterior of the filter element; and
   a flow control device mounted on the filter assembly in cooperation with the filter element, the flow control device configured to allow fluid to flow from the interior volume of the filter element through the filter element wall in a forward direction, but occluding the filter element wall to prevent flow in a backwards direction.

2. An embolic protection device for capturing embolic debris contained within a fluid flowing through a lumen of a vessel of a patient, comprising:
   a filtering assembly having a filter element having a wall defining an interior volume of the filter element and an exterior of the filter element, the wall of the filter element being capable of capturing embolic material while allowing fluid to flow from the interior volume to the exterior of the filter element; and
   a flow control device mounted on the filtering assembly in cooperation with the filter element, the flow control device configured to allow fluid to flow from the interior volume of the filter element through the filter element wall in a forward direction, but preventing flow through the filter element wall in a backwards direction, wherein the filter element further includes an opening in the wall providing fluid communication between the interior volume of the filter element and the exterior of the filter element, and the flow control device comprises a one-way valve configured to occlude the opening to prevent flow through the filter element in a backwards direction.

3. The embolic protection device of claim 2, wherein the one-way valve is a flexible flap attached to the filter element adjacent the opening such that the flexible flap has an open position when fluid flows through the opening from the interior of the filter element and has a closed position when aspiration is applied to the interior of the filter element.

4. The embolic protection device of claim 2, wherein the one-way valve is a sheath attached to the filter element in such a manner so as to occlude the opening and prevent fluid flow through the opening when aspiration is applied to the interior of the filter element.

5. The embolic protection device of claim 4, wherein the filter element includes a plurality of openings and the sheath is configured to occlude at least a portion of the plurality of openings.

6. The embolic protection device of claim 2, wherein the one-way valve is formed as part of the filter element.

7. The embolic protection device of claim 1, wherein the filter element further includes a plurality of openings and the flow control device comprises a plurality of sheaths attached to the exterior of the filter element and configured to occlude at least portion of the plurality of openings.

8. The embolic protection device of claim 7, wherein the plurality of sheaths are integrally formed of the filter element.

9. The embolic protection device of claim 1, wherein the filter element includes a plurality of openings and the flow control device comprises at least one sheath configured to occlude at least one of the plurality of openings.

10. The embolic protection device of claim 1, wherein the flow control device is a flap configured to cooperate with the wall to allow fluid to flow through the wall from the interior of the filter element in a forward direction and to prevent flow through the wall in a backwards direction.

11. An embolic protection device for capturing embolic debris released into a body vessel of a patient, comprising:
    a shaft member having distal and proximal ends;
    a filtering assembly rotatably mounted on the shaft member, the filtering assembly including
       an expandable strut assembly and a filter element attached to the strut assembly for capturing embolic debris, the expandable strut assembly having a set of expandable struts, each strut having a first and second end, and
       a deployment member movable between a collapsed position and an expanded position, wherein the first ends of the set of struts each are attached to the deployment member at different locations along the deployment member and the set of expandable struts are movable between a collapsed position and an expanded position, the filter element being movable with the struts to the expanded position so that at least a portion thereof contacts the wall of the vessel to capture embolic debris released into the body vessel; and
    a flow control device mounted on the filter assembly in cooperation with the filter element, the flow control device configured to allow fluid to flow through the filter element but occluding the filter element to prevent flow in a backwards direction.

12. The embolic protection device of claim 11, wherein the filter element includes a central region having an inlet opening and defining a storage reservoir for capturing embolic debris, the central region having a plurality of openings adapted to allow blood to flow therethrough to an exterior of the filter element but capture embolic debris larger than the size of the openings and contain the debris within the reservoir and the flow control device is configured to prevent blood flow from the exterior of the filter element through at least a portion of the plurality of openings into the central region.

13. The embolic protection device of claim 12, wherein the flow control device comprises at least one flexible flap mounted on the filter element adjacent at least one of the plurality of openings such that the flexible flap has an open position when fluid flows through the at least one of the plurality of openings from the central region of the filter element and has a closed position when aspiration is applied to the central region of the filter element.

14. The embolic protection device of claim 12, wherein the flow control device is at least one sleeve attached to the filter element in such a manner so that the at least one sleeve occludes at least one of the plurality of openings and prevents fluid flow through the at least one opening when aspiration is applied to the central region of the filter element.

15. The embolic protection device of claim 11, wherein the flow control device is formed as part of the filter element.

16. An embolic protection device for capturing embolic debris contained within a fluid flowing through a lumen of a vessel of a patient, comprising:

a filtering assembly having a filter element having a filter element wall defining an interior volume of the filter element and an exterior of the filter element, the filter element wall having at least one opening sized to capture embolic material while allowing fluid to flow from the interior volume of the filter element to the exterior of the filter element; and a flow control device mounted on the filter assembly in cooperation with the filter element, the flow control device configured to allow fluid to flow from the interior volume of the filter element through the at least one opening in a forward direction, but occluding the at least one opening to prevent flow in a backwards direction.

17. The embolic protection device of claim 16, wherein the flow control device comprises a one-way valve configured to occlude the at least one opening to prevent flow through the at least one opening in a backwards direction.

18. The embolic protection device of claim 17, wherein the one-way valve is a flexible flap joined to the filter element adjacent the at least one opening such that the flexible flap has an open position when fluid flows through the at least one opening from the interior of the filter element and has a closed position when aspiration is applied to the interior of the filter element.

19. The embolic protection device of claim 17, wherein the one-way valve is a sleeve attached to the filter element in such a manner so as to occlude the at least one opening and prevent fluid flow through the at least one opening when aspiration is applied to the interior of the filter element.

20. The embolic protection device of claim 19, wherein in the filter element includes a plurality of openings and the sleeve is configured to occlude at least a portion of the plurality openings.

21. The embolic protection device of claim 17, wherein the one-way valve is formed as part of the filter element.

22. The embolic protection device of claim 17, wherein the filter element further includes a plurality of openings and wherein the flow control device comprises a plurality of sleeves attached to the exterior of the filter element and configured to occlude at least portion of the plurality of openings.

23. The embolic protection device of claim 22, wherein the plurality of sleeves are integrally formed of the filter element.

24. An embolic protection device for capturing embolic debris contained within a fluid flowing through a lumen of a vessel of a patient, comprising:

a filtering assembly having a filter element having a wall defining an interior volume of the filter element and an exterior of the filter element, the wall allowing fluid to flow from the interior volume to the exterior of the filter element while capturing embolic material contained within the fluid; and a one-way valve mounted on the filter assembly in cooperation with the filter element, the one-way valve configured to allow fluid to flow from the interior volume of the filter element through the wall in a forward direction, but to occlude the wall to prevent fluid flow in a backwards direction.

25. An embolic protection device for capturing embolic debris contained within a fluid flowing through a lumen of a vessel of a patient, comprising:

a filtering assembly having a filter element having a wall defining an interior volume of the filter element and an exterior of the filter element the wall allowing fluid to flow from the interior volume to the exterior of the filter element while capturing embolic material contained within the fluid; and at least one flexible flap configured to cooperate with the wall to allow fluid to flow from the interior volume of the filter element through the wall in a forward direction and to occlude the wall to prevent flow in a backwards direction.

26. The embolic protection device of claim 25, wherein the wall has at least one opening and the at least one flexible flap is mounted to the filter element adjacent the at least one opening such that the at least one flexible flap has an open position to allow fluid to flow through the at least one opening from the interior volume of the filter element and has a closed position to prevent fluid flow from the exterior of the filter element through the at least one opening into the interior volume of the filter element.

27. The embolic protection device of claim 25, wherein the filter element includes a plurality of openings and a plurality of flexible flaps configured to cooperate with a portion of the plurality of openings.

28. An embolic protection device for capturing embolic debris contained within a fluid flowing through a lumen of a vessel of a patient, comprising:

a filtering assembly having a filter element having a wall defining an interior volume of the filter element and an exterior of the filter element, the wall allowing fluid to flow from the interior volume to the exterior of the filter element while capturing embolic material contained within the fluid; and at least one sleeve configured to cooperate with the wall to allow fluid to flow from the interior volume of the filter element through the wall in a forward direction and to occlude the wall to prevent flow in a backwards direction.

29. The embolic protection device of claim 28, wherein the wall has at least one opening providing fluid communication between the interior volume of the filter element and the exterior of the filter element, the at least one sleeve being configured to allow fluid to flow through the at least one opening from the interior volume of the filter element to the exterior of the filter element and to prevent fluid flow from the exterior of the filter element through the at least one opening into the interior volume of the filter element.

30. The embolic protection device of claim 28, wherein the filter element includes a plurality of openings and the at least one sleeve is configured to allow fluid to flow through at least a portion of the plurality of openings from the interior volume of the filter element to the exterior of the filter element and to prevent fluid flow from the exterior of the filter element through the at least portion of the plurality of openings into the interior volume of the filter element.

31. The embolic protection device of claim 30, wherein the at least one sleeve includes a plurality of sleeves, each sleeve of the plurality of sleeves configured to cooperate with a portion of the plurality of openings to allow fluid to flow through the portion of the plurality of openings from the interior volume of the filter element to the exterior of the filter element and to prevent fluid flow from the exterior of the filter element through the portion of the plurality of openings into the interior volume of the filter element.

32. The embolic protection device of claim 31, wherein a portion of the plurality of openings do not cooperate with any of the plurality of sleeves.

33. An embolic protection device for capturing embolic debris contained within a fluid flowing through a lumen of a vessel of a patient, comprising:

a filtering assembly having a filter element having a wall defining an interior volume of the filter element and an exterior of the filter element, the wall of the filter element having a capability to capture embolic material while allowing fluid to flow from the interior volume to the exterior of the filter element; and means mounted on the filtering assembly in cooperation with the wall for allowing fluid to flow from the interior volume of the filter element through the wall in a forward direction and for occluding flow through the wall in a backwards direction.

34. An embolic protection device for capturing embolic debris contained within a fluid flowing through a lumen of a vessel of a patient, comprising:

a filtering assembly having a filter element having a wall defining an interior volume of the filter element an exterior of the filter element, the wall of the filter element having a capability to capture embolic material while allowing fluid to flow from the interior volume to the exterior of the filter element; and means mounted on the filtering assembly in cooperation with the wall for allowing fluid to flow from the interior volume of the filter element through the wall in a forward direction and for allowing some limited flow through the wall in a backwards direction.

* * * * *

UNITED STATES PATENT AND TRADEMARK OFFICE
CERTIFICATE OF CORRECTION

PATENT NO. : 6,656,351 B2
DATED : December 2, 2003
INVENTOR(S) : William J. Boyle It is certified that error appears in the above-identified patent and that said Letters Patent is hereby corrected as shown below:

Column 24,
Line 24, delete "and".

Column 30,
Delete lines 21 through 32.

Column 33,
Line 53, delete "if", and insert -- of --.

Column 34,
Line 11, after "example," insert -- a --.

Column 38,
Line 18, after "element" insert -- , -- .

Signed and Sealed this

Twenty-fourth Day of August, 2004

JON W. DUDAS
*Director of the United States Patent and Trademark Office*